US010196668B2

(12) United States Patent
Gelb et al.

(10) Patent No.: US 10,196,668 B2
(45) Date of Patent: Feb. 5, 2019

(54) REAGENTS AND METHODS FOR SCREENING MPS I, II, IIIA, IIIB, IVA, VI, AND VII

(71) Applicant: University of Washington through its Center for Commercialization, Seattle, WA (US)

(72) Inventors: Michael H. Gelb, Seattle, WA (US); Arun Babu Kumar, Seattle, WA (US); Frances Hocutt, Seattle, WA (US); Zdenek Spacil, Seattle, WA (US); Mariana Natali Barcenas Rodriguez, Seattle, WA (US); Frantisek Turecek, Seattle, WA (US); C. Ronald Scott, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 347 days.

(21) Appl. No.: 14/916,526

(22) PCT Filed: Sep. 5, 2014

(86) PCT No.: PCT/US2014/054398
§ 371 (c)(1),
(2) Date: Mar. 3, 2016

(87) PCT Pub. No.: WO2015/035239
PCT Pub. Date: Mar. 12, 2015

(65) Prior Publication Data
US 2016/0298166 A1    Oct. 13, 2016

Related U.S. Application Data

(60) Provisional application No. 62/012,020, filed on Jun. 13, 2014, provisional application No. 61/968,021, filed on Mar. 20, 2014, provisional application No. 61/949,970, filed on Mar. 7, 2014, provisional application No. 61/960,113, filed on Sep. 9, 2013, provisional application No. 61/960,102, filed on Sep. 9, 2013, provisional application No. 61/874,331, filed on Sep. 5, 2013, provisional application No. 61/874,293, filed on Sep. 5, 2013.

(51) Int. Cl.
*C12Q 1/34* (2006.01)
*C07H 15/203* (2006.01)

(52) U.S. Cl.
CPC ............. *C12Q 1/34* (2013.01); *C07H 15/203* (2013.01); *G01N 2333/916* (2013.01); *G01N 2333/924* (2013.01)

(58) Field of Classification Search
None
See application file for complete search history.

(56) References Cited

U.S. PATENT DOCUMENTS

| 2007/0072243 A1 | 3/2007 | Miekle et al. |
| 2008/0145836 A1* | 6/2008 | Zhang ................. A61K 31/164 435/4 |
| 2010/0209951 A1* | 8/2010 | Gelb ................... C07D 311/16 435/18 |
| 2012/0164670 A1 | 6/2012 | Hubbard et al. |

FOREIGN PATENT DOCUMENTS

| WO | 2009/131698 A2 | 10/2009 |
| WO | 2013/070953 A1 | 5/2013 |

OTHER PUBLICATIONS

Li ("Direct Mulitplex Assay of Lysosomal Enzymes in Dried Blood Spots for Newborn Screening" Clinical Chemistry, 2004, 50:10, 1785-1796). (Year: 2004).*
Blanchard ("Tandem Mass Spectrometry for the Direct Assay of Lysosomal Enzymes in Dried Blood spots: Application to Screening Newborns for Mucopolysaccharidosis I", Clinical Chemistry, 2008, 54:12, 2067-2070) (Year: 2008).*
Spacil ("High-throughput Assay of 9 Lysosomal Enzymes for Newborn Screening", Clinical Chemistry, 2013, 502-511). (Year: 2013).*
Extended European Search Report dated May 22, 2017, issued in corresponding European Application No. 14842380.9, filed Sep. 5, 2014, 11 pages.
Communication Pursuant to Article 94(3) EPC, dated Jan. 24, 2018, issued in European Application No. 14842380.9, filed Sep. 5, 2014, 7 pages.
International Search Report and Written Opinion dated Feb. 4, 2015, issued in corresponding International Application No. PCT/US2014/054398, filed Sep. 5, 2014, 12 pages.
Chennamaneni, N.K., et al., "Improved Reagents for Newborn Screening of Mucopolysaccharidosis Types I, II, and VI by Tandem Mass Spectrometry," Analytical Chemistry 86(9):4508-4514, May 2014.
Partial Supplementary European Search Report dated Feb. 16, 2017, issued in corresponding European Application No. 14 842 380.9, filed Sep. 5, 2014, 7 pages.

(Continued)

*Primary Examiner* — Robert J Yamasaki
*Assistant Examiner* — Charles Zoltan Constantine
(74) *Attorney, Agent, or Firm* — Christensen O'Connor Johnson Kindness PLLC

(57) ABSTRACT

Reagents, methods, and kits for assaying enzymes associated with lysosomal storage diseases MPS-I, MPS-II, MPS-IIIA, MPS-IIIB, MPS-IV A, MPS-VI, and MPS VII. In one aspect, the invention provides methods for assaying one or more enzymes associated with a lysosomal storage disease. In a first embodiment, the method includes: (a) contacting a sample with a first solution to provide a solution comprising one or more lysosomal enzymes; (b) contacting the one or more lysosomal enzymes in solution with an enzyme substrate for each lysosomal enzyme to be analyzed and incubating the substrates with the enzymes for a time sufficient to provide a solution comprising an enzyme product for each lysosomal enzyme present in the sample.

4 Claims, 5 Drawing Sheets

(56) References Cited

OTHER PUBLICATIONS

Spáčil, Z., et al., "Comparative Triplex Tandem Mass Spectrometry Assays of Lysosomal Enzyme Activities in Dried Blood Spots Using Fast Liquid Chromatography: Application to Newborn Screening of Pompe, Fabry, and Hurler Diseases," Analytical Chemistry 83(12):4822-4828, Jun. 2011; with supporting information: Scheme S1, Tables S1-S8, Figures S1-S9 (Feb. 2011), 19 pages.

Spáčil, Z., et al., "Protonation Sites and Dissociation Mechanisms of T-Butylcarbamates in Tandem Mass Spectrometric Assays for Newborn Screening," Journal of Mass Spectrometry 46(10):1089-1098, Oct. 2011.

Communication Pursuant to Article 94(3) EPC dated Oct. 22, 2018, issued in corresponding European Application No. 14842380.9, filed Sep. 5, 2014, 4 pages.

First Office Action dated Sep. 11, 2018, issued in corresponding Japanese Application No. 2016-540440, filed Sep. 5, 2014, 10 pages.

* cited by examiner

REAGENTS AND METHODS FOR SCREENING MPS I, II, IIIA, IIIB, IVA, VI, AND VII

CROSS-REFERENCE TO RELATED APPLICATIONS

This application claims the benefit of U.S. Provisional Application No. 61/874,293, filed Sep. 5, 2013; U.S. Provisional Application No. 61/874,331, filed Sep. 5, 2013; U.S. Provisional Application No. 61/960,102, filed Sep. 9, 2013; U.S. Provisional Application No. 61/960,113, filed Sep. 9, 2013; U.S. Provisional Application No. 61/949,970, filed Mar. 7, 2014; U.S. Provisional Application No. 61/968,021, filed Mar. 20, 2014; and U.S. Provisional Application No. 62/012,020, filed Jun. 13, 2014; each expressly incorporated herein by reference in its entirety.

STATEMENT OF GOVERNMENT LICENSE RIGHTS

This invention was made with Government support under Grant No. DK067859 awarded by National Institutes of Health. The Government has certain rights in the invention.

FIELD OF THE INVENTION

The present invention relates to reagents, methods, and kits for screening MPS I, II, IIIA, IIIB, IVA, VI, and VII.

BACKGROUND OF THE INVENTION

Treatments for a subset of lysosomal storage disorders (LSDs) have become available, and in many cases, early initiation of therapy leads to a clinical improvement. These encouraging results have spawned widespread interest in newborn screening of LSDs.

Newborn screening programs have been established to quantify the level of metabolites associated with these treatable diseases. New York State now provides Krabbe disease screening and recent legislation for LSD expanded newborn screening has passed in several other states, and newborn screening for Pompe and Fabry diseases is carried out in Taiwan.

The MPS (MPS I to VII) are a group of metabolic diseases/syndromes caused by a deficiency of one of the lysosomal enzymes degrading the glycosaminoglycans (including heparan, dermatan, keratan, or chondroitin sulfate). The pertinent enzymes include five sulfatases, four exoglycosidases, and one non-hydrolytic acetyl-N-transferase. These syndromes result in non-degraded or partially-degraded glycosaminoglycans amassing in the lysosome resulting in irreversible multi-systemic organ damage.

Although treatments have recently become available for some of the MPS syndromes, optimal benefits from these treatments would require commencement of treatment prior to the onset of the irreversible symptoms. Early detection of MPS syndromes maximizes the potential benefit of treatment, and thus there is the need to develop tests that are appropriate for early diagnosis. Likewise, there is a need for developing a fast, inexpensive, and reliable diagnostic procedure that uses dried blood spots (DBS) as a sample source, such as those submitted to newborn screening laboratories.

Accordingly, a need exists for methods and reagents for newborn screening of the activity of lysosomal enzymes, particularly methods and reagents that allow for improved screening of MPS I, II, IIIA, IIIB, IVA, VI, and VII. The present invention fulfills this need and provides further related advantages.

SUMMARY OF THE INVENTION

The present invention provides reagents for screening MPS I, II, IIIA, IIIB, IVA, VI, and VII, methods for screening for MPS I, II, IIIA, IIIB, IVA, VI, and VII , and kits that include the reagents.

In one aspect, the invention provides methods for assaying one or more enzymes associated with a lysosomal storage disease.

In a first embodiment, the method includes:

(a) contacting a sample with a first solution to provide a solution comprising one or more lysosomal enzymes;

(b) contacting the one or more lysosomal enzymes in solution with an enzyme substrate for each lysosomal enzyme to be analyzed and incubating the substrates with the enzymes for a time sufficient to provide a solution comprising an enzyme product for each lysosomal enzyme present in the sample, wherein the enzyme substrate for each lysosomal enzyme is a compound having a carbohydrate moiety and an aglycone moiety and having the formula:

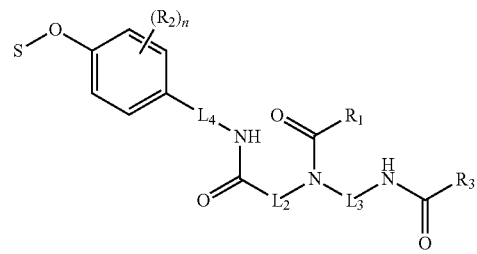

wherein S is the carbohydrate moiety that when covalently coupled to the aglycone moiety provides a substrate for an enzyme selected from the group consisting of:

(i) alpha-L-iduronidase;
(ii) iduronate 2-sulfatase;
(iii) heparan N-sulfatase;
(iv) N-acetyl-alpha-D-glucosaminidase;
(v) N-acetylgalactosamine 6-sulfate-sulfatase;
(vi) N-acetylgalactosamine 4-sulfate-sulfatase; and
(vii) beta-glucuronidase;

$L_2$ is a linker comprising 1-20 carbon atoms in which one or more carbon atoms may be replaced with a heteroatom selected from N, O, and S, and/or one or more of carbon atoms may be substituted with a $C_1$-$C_6$ alkyl group or halogen;

$L_3$ is a linker comprising 1-20 carbon atoms in which one or more carbon atoms may be replaced with a heteroatom selected from N, O, or S, and/or one or more of carbon atoms may be substituted with a $C_1$-$C_6$ alkyl group or halogen;

$L_4$ is optional and when present is a linker comprising 1-20 carbon atoms in which one or more carbon atoms may be replaced with a heteroatom selected from N, O, or S), and/or one or more of carbon atoms may be substituted with a $C_1$-$C_6$ alkyl group or halogen;

$R_1$ is a $C_1$-$C_{10}$ alkyl group or a $C_1$-$C_{10}$ alkoxy group;

$R_2$ at each occurrence is independently selected from a $C_1$-$C_{10}$ alkyl group, a $C_1$-$C_{10}$ alkoxy group, halogen, nitro, —C(=O)NHR, or —C(=O)OR, where R is $C_1$-$C_8$ alkyl group;

$R_3$ is a $C_1$-$C_{10}$ alkyl group or a substituted or unsubstituted $C_6$-$C_{10}$ aryl group; and n is 0, 1, 2, 3, or 4; and (c) determining the quantities of one or more of the enzyme products.

In certain embodiments, the method further includes contacting the enzyme products with a glycohydrolase to provide second enzyme products. In certain embodiments, the method further includes adding an inhibitor to block endogenous glycohydrolase enzymatic activity that acts on a substrate for N-acetylgalactosamine 6-sulfate-sulfatase or N-acetylgalactosamine 4-sulfate-sulfatase.

In a second embodiment, the method includes:

(a) contacting a sample with a first solution to provide a solution comprising one or more lysosomal enzymes;

(b) contacting the one or more lysosomal enzymes in solution with an enzyme substrate for each lysosomal enzyme to be analyzed and incubating the substrates with the enzymes for a time sufficient to provide a solution comprising a first enzyme product for each lysosomal enzyme present in the sample;

(c) subjecting the first enzyme products to a glycohydrolase to provide a second enzyme product for each first enzyme product susceptible to further enzymatic action by the glycohydrolase; and (d) determining the quantities of one or more of the first enzyme products and/or one or more of the second enzyme products.

In the above method, certain first enzyme products are not susceptible to further enzymatic action by the glycohydrolase. First enzyme products that are not susceptible to further enzymatic action by the glycohydrolase are provided by the action of an enzyme selected from:

(a) alpha-L-iduronidase;
(b) N-acetyl-alpha-D-glucosaminidase; and
(c) beta-glucuronidase.

First enzyme products susceptible to further enzymatic action by the glycohydrolase are provided by the action of an enzyme selected from (a) iduronate 2-sulfatase;
(b) heparan N-sulfatase;
(c) N-acetylgalactosamine 6-sulfate-sulfatase; and
(d) N-acetylgalactosamine 4-sulfate-sulfatase.

In certain embodiments, the method further includes adding an inhibitor to block endogenous glycohydrolase enzymatic activity that acts on a substrate for N-acetylgalactosamine 6-sulfate-sulfatase or N-acetylgalactosamine 4-sulfate-sulfatase, where the inhibitor does not significantly inhibit the activity of the glycohydrolase of step (c).

In the above methods, the one or more lysosomal enzymes comprises an enzyme selected from:

(a) alpha-L-iduronidase;
(b) iduronate 2-sulfatase;
(c) heparan N-sulfatase;
(d) N-acetyl-alpha-D-glucosaminidase;
(e) N-acetylgalactosamine 6-sulfate-sulfatase;
(f) N-acetylgalactosamine 4-sulfate-sulfatase; and
(g) beta-glucuronidase.

In certain embodiments of the above methods, an internal standard for each lysosomal enzyme to be analyzed is added before, after, or simultaneously with contacting the lysosomal enzymes with the substrates.

In certain embodiments of the above methods, the enzyme reaction is quenched prior to determining the quantities of one or more of the enzyme products.

In embodiments of the above methods, the sample is a blood or tissue sample. In certain embodiments, the sample is a dried blood spot.

Representative glycohydrolases include human hexosaminidase A, bacterial N-acetylhexosaminidases, bacterial β-N-acetylgalactosaminidase, alpha-L-iduronidase, β-galactosidase (aspergillus), and α-glucosidase (yeast).

Representative inhibitors include (Z)—O-(2-acetamido-2-deoxy-D-glucopyranosylidene)-amino N-phenylcarbamate, 1-deoxynojirmycin, castanospermine, swainsonine, calystegine $B_2$, isofagamine, Tamiflu, gluconohydroximolactone, glucuronic acid and its lactones and lactams, Relenza, miglitol, phenethyl substituted gluco-and galacto-imidazoles, N-hydroxyethyl dehydronojirimycin, GalNAc thiazoline, and GlcNAc thiazoline.

In certain embodiments of the above methods, determining the quantities of the enzyme products (e.g., first and/or second enzyme products) includes mass spectrometric analysis. In certain embodiments, determining the quantities of the enzyme products includes determining the ratio of each product to its internal standard by mass spectrometric analysis. In certain embodiments, determining the quantities of the enzyme products includes tandem mass spectrometric analysis in which the parent ions of the products and their internal standards are generated, isolated, and subjected to collision-induced dissociation to provide product fragment ions and internal standard fragment ions. In certain embodiments, determining the quantities of the enzyme products includes comparing the peak intensities of the product fragment ions and internal standard fragment ions to calculate the amount of the products. In certain embodiments, determining the quantities of the enzyme products includes conducting the products to a mass spectrometer by liquid chromatography or by flow injection.

In certain embodiments of the above methods, determining the quantities of the enzyme products includes fluorescence analysis.

In certain embodiments of the above methods, the method further includes using the quantities of the enzyme products to determine whether the sample is from a candidate for treatment for a condition associated with one or more lysosomal enzyme deficiencies.

In the second embodiment of the method noted above, in certain embodiments, the substrate has a carbohydrate moiety and an aglycone moiety and has the formula:

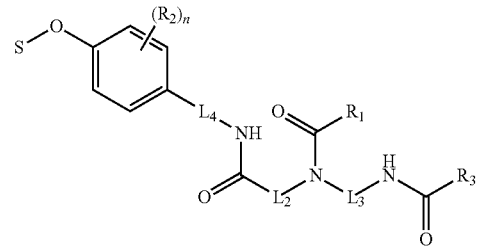

wherein S is the carbohydrate moiety that when covalently coupled to the aglycone moiety provides a substrate for an enzyme selected from the group consisting of:

(a) alpha-L-iduronidase;
(b) iduronate 2-sulfatase;
(c) heparan N-sulfatase;
(d) N-acetyl-alpha-D-glucosaminidase;
(e) N-acetylgalactosamine 6-sulfate-sulfatase;
(f) N-acetylgalactosamine 4-sulfate-sulfatase; and
(g) beta-glucuronidase;

$L_2$ is a linker comprising 1-20 carbon atoms in which one or more carbon atoms may be replaced with a heteroatom selected from N, O, and S, and/or one or more of carbon atoms may be substituted with a $C_1$-$C_6$ alkyl group or halogen;

$L_3$ is a linker comprising 1-20 carbon atoms in which one or more carbon atoms may be replaced with a heteroatom selected from N, O, or S, and/or one or more of carbon atoms may be substituted with a $C_1$-$C_6$ alkyl group or halogen;

$L_4$ is optional and when present is a linker comprising 1-20 carbon atoms in which one or more carbon atoms may be replaced with a heteroatom selected from N, O, or S), and/or one or more of carbon atoms may be substituted with a $C_1$-$C_6$ alkyl group or halogen;

$R_1$ is a $C_1$-$C_{10}$ alkyl group or a $C_1$-$C_{10}$ alkoxy group;

$R_2$ at each occurrence is independently selected from a $C_1$-$C_{10}$ alkyl group, a $C_1$-$C_{10}$ alkoxy group, halogen, nitro, —C(=O)NHR, or —C(=O)OR, where R is $C_1$-$C_8$ alkyl group;

$R_3$ is a $C_1$-$C_{10}$ alkyl group or a substituted or unsubstituted $C_6$-$C_{10}$ aryl group; and n is 0, 1, 2, 3, or 4.

Representative substrates useful in the methods of the invention include the substrates of the invention described herein and noted below.

Representative internal standards useful in the methods of the invention include the internal standards of the invention described herein.

In another aspect of the invention, reagents (substrates and internal standards) for assaying one or more enzymes associated with a lysosomal storage disease are provided.

Representative substrates include compounds having a carbohydrate moiety and an aglycone moiety and having the formula:

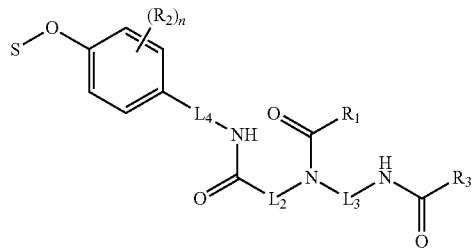

wherein

S is the carbohydrate moiety that when covalently coupled to the aglycone moiety provides a substrate for an enzyme selected from the group consisting of:
(a) alpha-L-iduronidase;
(b) iduronate 2-sulfatase;
(c) heparan N-sulfatase;
(d) N-acetyl-alpha-D-glucosaminidase;
(e) N-acetylgalactosamine 6-sulfate-sulfatase;
(f) N-acetylgalactosamine 4-sulfate-sulfatase; and
(g) beta-glucuronidase;

$L_2$ is a linker comprising 1-20 carbon atoms in which one or more carbon atoms may be replaced with a heteroatom selected from N, O, and S, and/or one or more of carbon atoms may be substituted with a $C_1$-$C_6$ alkyl group or halogen;

$L_3$ is a linker comprising 1-20 carbon atoms in which one or more carbon atoms may be replaced with a heteroatom selected from N, O, or S, and/or one or more of carbon atoms may be substituted with a $C_1$-$C_6$ alkyl group or halogen;

$L_4$ is optional and when present is a linker comprising 1-20 carbon atoms in which one or more carbon atoms may be replaced with a heteroatom selected from N, O, or S), and/or one or more of carbon atoms may be substituted with a $C_1$-$C_6$ alkyl group or halogen;

$R_1$ is a $C_1$-$C_{10}$ alkyl group or a $C_1$-$C_{10}$ alkoxy group;

$R_2$ at each occurrence is independently selected from a $C_1$-$C_{10}$ alkyl group, a $C_1$-$C_{10}$ alkoxy group, halogen, nitro, —C(=O)NHR, or —C(=O)OR, where R is $C_1$-$C_8$ alkyl group;

$R_3$ is a $C_1$-$C_{10}$ alkyl group or a substituted or unsubstituted $C_6$-$C_{10}$ aryl group; and n is 0, 1, 2, 3, or 4.

In certain embodiments, $L_2$ is —$(CH_2)_n$—, where n is 1-6.
In certain embodiments, $L_3$ is —$(CH_2)_m$—, where m is 1-12.
In certain embodiments, $L_4$ is —$(CH_2)_n$—, where n is 1-6.
In certain embodiments, $L_4$ is absent.
In certain embodiments, $R_1$ is $C_1$-$C_5$ alkyl.
In certain embodiments, $R_2$ is $C_1$-$C_8$ alkyl.
In certain embodiments, $R_3$ is $C_1$-$C_6$ alkyl.
In certain embodiments, $R_3$ is phenyl.

Representative substrates are shown below.

In certain embodiments, the substrate has the formula:

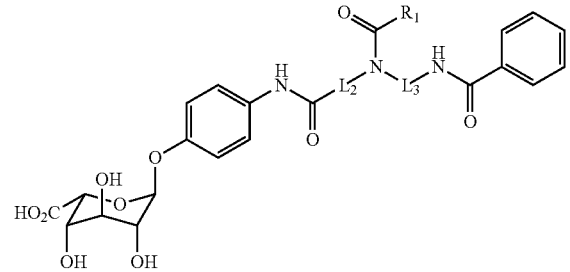

In one embodiment, the substrate has the formula:

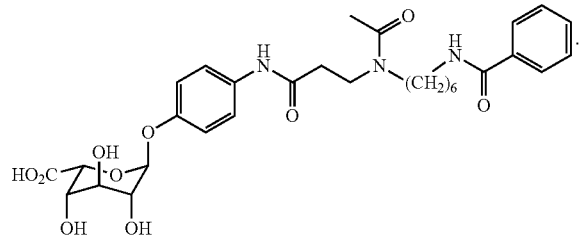

In certain embodiments, the substrate has the formula:

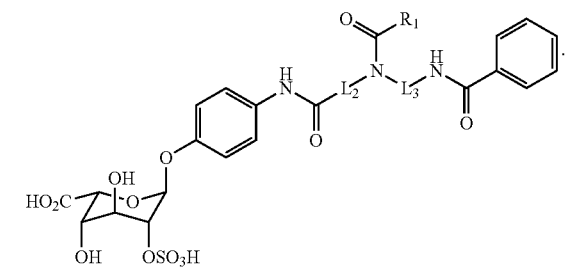

In one embodiment, the substrate has the formula:

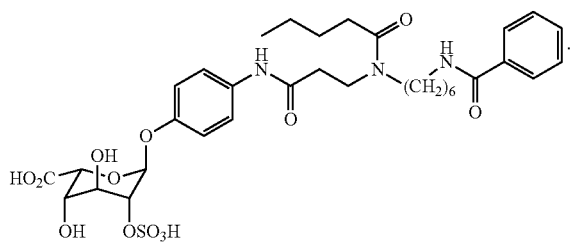

In certain embodiments, the substrate has the formula:

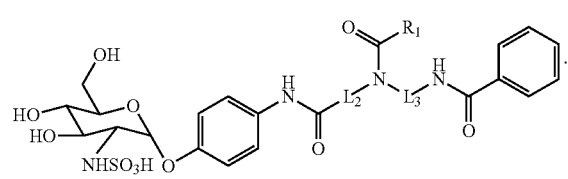

In one embodiment, the substrate has the formula:

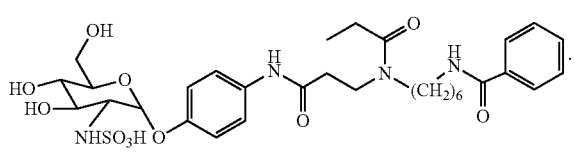

In certain embodiments, the substrate has the formula:

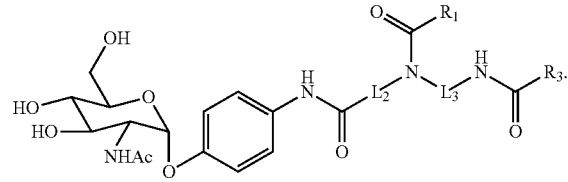

In one embodiment, the substrate has the formula:

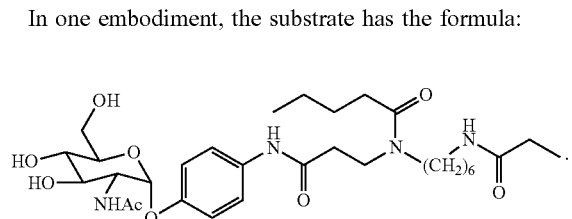

In certain embodiments, the substrate has the formula:

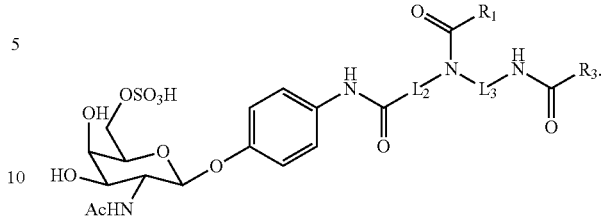

In one embodiment, the substrate has the formula:

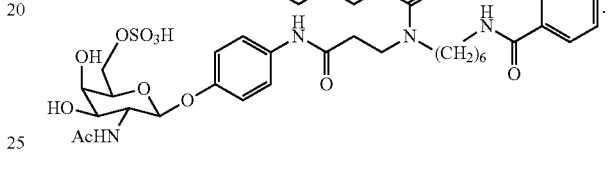

In certain embodiments, the substrate has the formula:

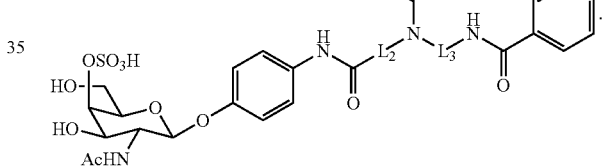

In one embodiment, the substrate has the formula:

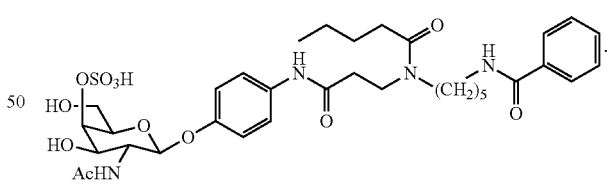

In certain embodiments, the substrate has the formula:

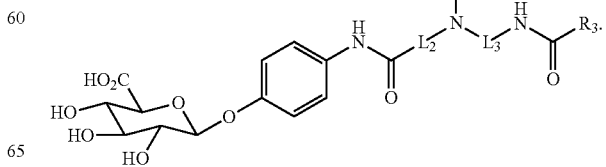

In one embodiment, the substrate has the formula:

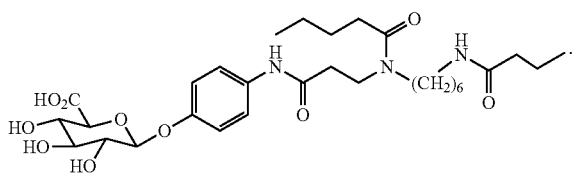

In a further aspect of the invention, kits for assaying one or more enzymes associated with a lysosomal storage disease is provided. In one embodiment, the kit includes one or more reagents (e.g., substrate and internal standards) of the invention. In certain embodiments, enzymes capable of assay by the kit includes one or more of alpha-L-iduronidase (MPS-I), iduronate-2-sulfatase (MPS-II), heparan N-sulfatase (MPS-IIIA), N-acetyl-alpha-D-glycosaminidase (MPS-IIIB), N-acetylgalactosamine-6-sulfate-sulfatase (MPS-IVA), N-acetylgalactosamine-4-sulfate-sulfatase (MPS-VI), and beta-glucuronidase (MPS-VII).

DETAILED DESCRIPTION OF THE INVENTION

Figure 1:
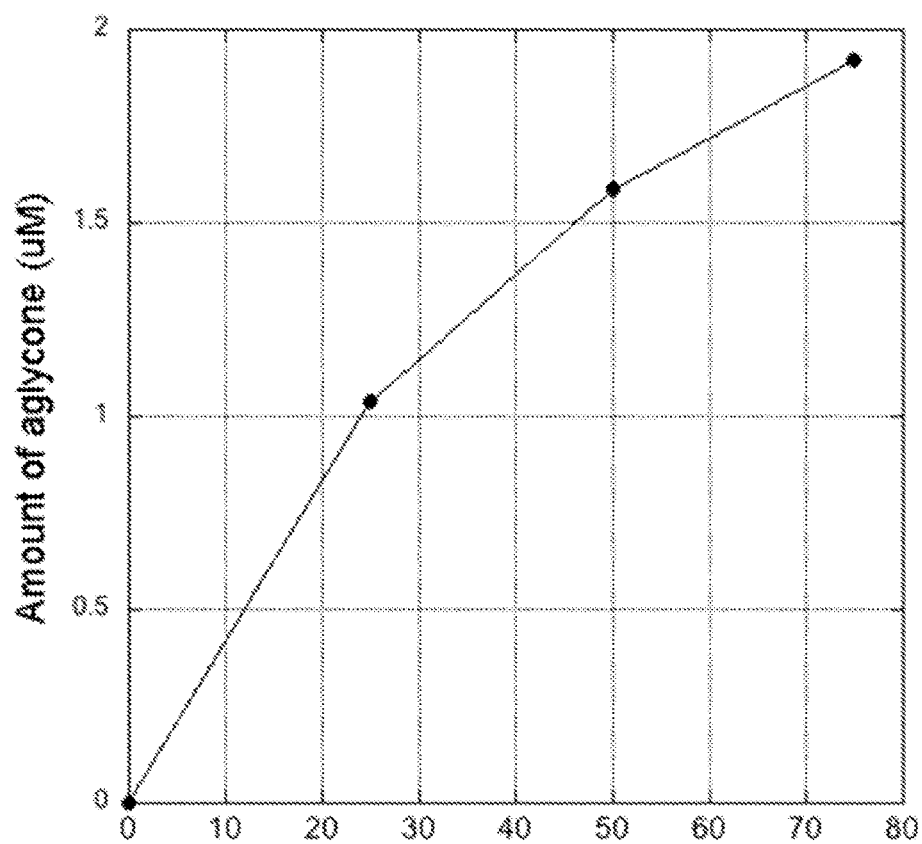
FIG. 1 is a graph illustrating amount of aglycone released as a function of amount of hexosaminidase A added in a representative MPS-VI assay of the invention. Aglycone detected by UHPLC-MS/MS.

The present invention provides reagents for screening mucopolysaccharidoses I, II, IIIA, IIIB, IVA, VI, and VII, (MPS-I, II, IIIA, IIB, IVA, VI, and VII, respectively), methods for screening for MPS-I, II, IIIA, IIIB, IVA, VI, and VII, and kits that include the reagents.

In one aspect, the invention provides reagents for screening MPS-I, II, IIIA, IIIB, IVA, VI, and VII screening. In certain embodiments, the reagents of the invention include substrates (S), products (P), and internals standards (IS) for screening for MPS I, II, IIIA, IIIB, IVA, VI, and VII.

In another aspect, the invention provides methods for screening for MPS I, II, IIIA, IIIB, IVA, VI, and VII. The methods assay specific enzymes, the deficiencies of which lead to the lysosomal storage disease conditions. The methods advantageously assay one or more of alpha-L-iduronidase (MPS-I), iduronate-2-sulfatase (MPS-II), heparan N-sulfatase (MPS-IIIA), N-acetyl-alpha-D-glycosaminidase (MPS-IIIB), N-acetylgalactosamine-6-sulfate-sulfatase (MPS-IVA), N-acetylgalactosamine-4-sulfate-sulfatase (MPS-VI), and beta-glucuronidase (MPS-VII).

Reagents

In one aspect, the present invention provides reagents that can be advantageously utilized to assay enzymes. The reagents include enzyme substrates (S), enzyme products (P) and assay internal standards (IS). In certain embodiments, one or more substrates (S) and their corresponding internal standards (IS) are incubated in a suitable buffer with a suitable source of enzymes such as a dried blood spot from a newborn screening card or a urine sample for a sufficient time to form one or more products (P) that are subsequently detected by tandem mass spectrometry. In certain embodiments, the internal standard (IS) is chemically similar or identical to the enzyme-formed product except the standard has a different mass (e.g., homolog or heavy isotope substituted such as deuterium and/or carbon-13 substitutions). In other embodiments, one or more substrates (S) are incubated in a suitable buffer with a suitable source of enzymes to form one or more products (P) that are subsequently detected by fluorescence analysis.

Enzymes that are advantageously assayed with the reagents of the invention include the following:

(a) alpha-L-iduronidase, which acts on the substrate MPS-I-S to produce the product MPS-I-P, and the assay makes use of the internal standard MPS-I-IS;

(b) iduronate-2-sulfatase, which acts on the substrate MPS-II-S to produce the product MPS-II-P, and the assay makes use of the internal standard MPS-II-IS;

(c) heparan N-sulfatase, which acts on the substrate MPS-IIIA-S to produce the product MPS-IIIA-P, and the assay makes use of the internal standard MPS-IIIA-IS;

(d) N-acetyl-alpha-D-glycosaminidase, which acts on the substrate MPS-IIIB-S to produce the product MPS-IIIB-P, and the assay makes use of the internal standard MPS-IIIB-IS;

(e) N-acetylgalactosamine-6-sulfate-sulfatase, which acts on the substrate MPS-IVA-S to produce the product MPS-IVA-P, and the assay makes use of the internal standard MPS-IVA-IS;

(f) N-acetylgalactosamine-4-sulfate-sulfatase, which acts on the substrate MPS-VI-S to produce the product MPS-VI-P, and the assay makes use of the internal standard MPS-VI-IS; and (g) beta-glucuronidase, which acts on the substrate MPS-VII-S to produce the product MPS-VII-P, and the assay makes use of the internal standard MPS-VII-IS.

The following is a description of the reagents of the invention, substrates (S), products (P), and internals standards (IS) for MPS-I, MPS-II, MPS-IIIA, MPS-IIIB, MPS IVA, MPS-VI, and MPS-VII.

Sugar-Aglycone. The substrates of the invention are glycosides. The term "glycoside" refers to a compound in which a sugar group (glycone) is bonded through its anomeric carbon to another group (aglycone) by a glycosidic bond.

The substrates of the invention are characterized as having a sugar-aglycone structure. The sugar component of the substrates is either the natural sugar that is a substrate for the particular enzyme or a modified sugar that maintains function sufficient to be a substrate for the particular enzyme to be assayed. The aglycone component of the substrate allows for analysis of the enzymatic activity. The aglycone component of the substrate is also a component of the enzyme product, which is analyzed to determine enzymatic activity. The aglycone component includes functionality for analysis for mass spectrometry or fluorescence. When the analysis is by mass spectrometry, an internal standard having a mass that is different from the product may be employed. The internal standard is either structurally identical to the product and includes one or more isotopes (e.g., deuterium or $^{13}C$) or is structurally similar having a functionally equivalent structure and a structural variation (e.g., a homolog: —$(CH_2)_5$— v. —$(CH_2)_6$—, or vice versa).

Aglycones. The reagents of the invention include an aglycone component. The nature of the aglycone can vary depending on the nature of the analytical technique utilized to assay the enzymes of interest. Representative aglycones are represented by formulae (I)-(VI) below. In the aglycone structures below, the wavy line depicts the point of attachment to the sugar anomeric carbon.

In certain embodiments, the aglycone is a Type A aglycone having the formula:

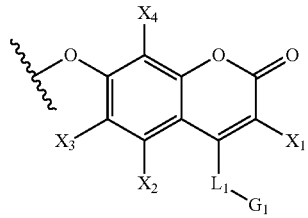

(I)

where $L_1$ is a linker that covalently couples $G_1$ to the coumarin moiety, and where $X_1$, $X_2$, $X_3$, and $X_4$ at each occurrence is independently hydrogen or halogen (e.g., chloro).

In certain embodiments, $L_1$ includes 1-20 carbon atoms (branched or linear) in which one or more carbon atoms may be replaced with an ether oxygen or —C(=O)O— group; a thioether sulfur or —C(=O)S— group; an NH, an N(R), or —C(=O)NH— or —C(=O)NR— where R is an alkyl group of 1-6 carbons. Substitution of one or more of the carbon atom hydrogen atoms is optional. In certain embodiments, $L_1$ is —CH$_2$—C(=O)—NH—(CH$_2$)$_5$-G$_1$.

$G_1$ includes a positively charged group (e.g., a permanently positively charged group such as a quaternary ammonium ion) such as one of the following:

(a) N(R$_a$)(R$_b$)(R$_c$)$^+$, where R$_a$, R$_b$, and R$_c$ are each independently H or an alkyl group of 1-6 carbons;

(b) S(R$_a$)(R$_b$)$^+$, where R$_a$ and R$_b$ are as above;

(c) a pyridinium of the type

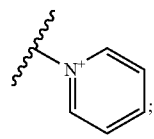 [SMILES: *[n+]1ccccc1]

(d) a pyridinium of the type

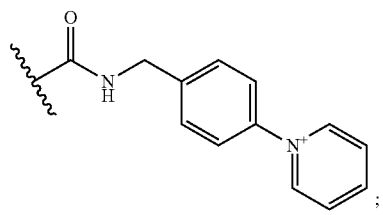 [SMILES: *C(=O)NCc1ccc(-[n+]2ccccc2)cc1]

(e) a pyridinium of the type

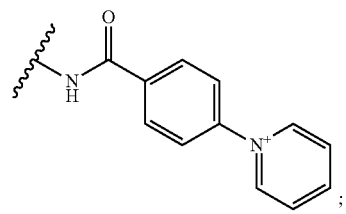 [SMILES: *NC(=O)c1ccc(-[n+]2ccccc2)cc1]

or (f) a pyridinium of the type

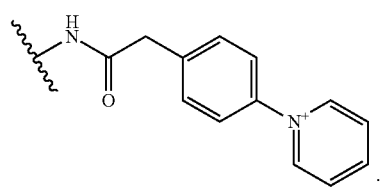 [SMILES: *NC(=O)Cc1ccc(-[n+]2ccccc2)cc1]

In certain embodiments, $L_1$ is —CH$_2$—C(=O)—NH—(CH$_2$)$_5$—C(=O)NH—CH$_2$—C$_6$H$_4$—N$^+$(C$_5$H$_5$), where —C$_6$H$_4$—N$^+$(C$_5$H$_5$) is p-pyridinium phenyl.

It will be appreciated that in addition to the coumarin (umbelliferone) aglycones defined above, other fluorescent aglycones can be utilized (e.g., fluoresceins, resorufins, rhodamines, nitrophenols, and 7-hydroxy-9H-(1,3-dichloro-9,9-dimethylacridin-2-ones, and their halogenated derivatives), as described below.

In certain embodiments, the Type A aglycone has the formula:

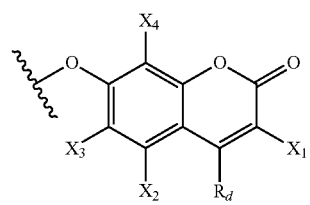

(II)

wherein R$_d$ is hydrogen or methyl, and X$_1$, X$_2$, X$_3$, and X$_4$ at each occurrence is independently hydrogen or halogen (e.g., chloro). In addition to the coumarin (umbelliferone) aglycone defined above, it will be appreciated that other fluorescent aglycones can be utilized. Suitable other aglycones include fluoresceins, resorufins, rhodamines, nitrophenols, and 7-hydroxy-9H-(1,3-dichloro-9,9-dimethylacridin-2-ones, and their halogenated derivatives. For the fluoresceins, resorufins, nitrophenols, and 7-hydroxy-9H-(1,3-dichloro-9,9-dimethylacridin-2-ones, the aglycone is coupled to the sugar through its hydroxy group as in the coumarins noted above. For the rhodamines, the aglycone is coupled to the sugar through its amino group.

Type A aglycone components can be included in the reagents of the invention to impart fluorescent functionality (i.e., coumarin, umbelliferone, fluorescein, resorufin, nitrophenol, rhodamine, 7-hydroxy-9H-(1,3-dichloro-9,9-dimethylacridin-2-one moieties) and to provide reagents that can be analyzed by fluorescence techniques.

In one embodiment, the aglycone is a Type B aglycone and has the formula:

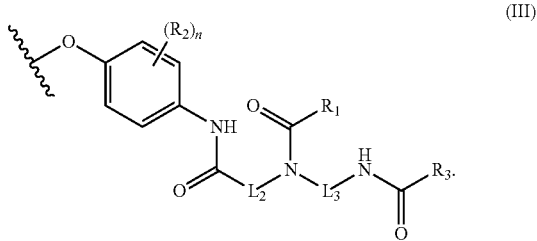

(III)

L₂ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_2$ is —$(CH_2)_n$—, where n is 1-6. In certain embodiments, $L_2$ is —$(CH_2)_2$—.

L₃ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_3$ is —$(CH_2)_m$—, where m is 1-12. In certain embodiments, $L_3$ is —$(CH_2)_m$—, where m is 4, 5, or 6.

$R_1$ is a $C_1$-$C_{10}$ alkyl group (e.g., branched or linear) or a $C_1$-$C_{10}$ alkoxy group (e.g., OtBu). In certain embodiments, $R_1$ is a $C_1$-$C_5$ alkyl group (e.g., methyl, ethyl, n-propyl, n-butyl, n-pentyl).

$R_2$ is at each occurrence is independently selected from a $C_1$-$C_{10}$ alkyl group (e.g., branched or linear), a $C_1$-$C_{10}$ alkoxy group (e.g., branched or linear), halogen (e.g., fluoro, chloro), nitro, —C(=O)NHR, or —C(=O)OR, where R is $C_1$-$C_8$ alkyl group (e.g., methyl), and n is 0, 1, 2, 3, or 4. Representative substitution patterns (relative to phenolic oxygen) for $R_2$ include 2-, 2,6-di, 3-, 3,5-di, and 2,3-di (i.e., 2- and 6-positions are ortho, and 3- and 5-positions are meta). In certain embodiments, $R_2$ is a fluoro, methyl, or methoxy group positioned either ortho or meta to the phenolic oxygen (e.g., 2-fluoro, 2-methyl, 2-methoxy, 3-fluoro, 3-methyl, 3-methoxy). In other embodiments, $R_2$ is a fluoro, methyl, or methoxy group positioned meta to the phenolic oxygen. In certain embodiments, n is zero and the phenylene group is unsubstituted.

$R_3$ is a $C_1$-$C_{10}$ alkyl group (e.g., branched or linear) or a substituted or unsubstituted $C_6$-$C_{10}$ aryl group (e.g., phenyl). Aryl groups substituents include a $C_1$-$C_{10}$ alkyl groups (e.g., branched or linear) and halogens (e.g., chloro). In certain embodiments, $R_3$ is a $C_1$-$C_6$ alkyl group (e.g., ethyl, n-propyl, n-butyl, n-pentyl). In other embodiments, $R_3$ is a phenyl group.

In certain embodiments, the Type B aglycone has the formula:

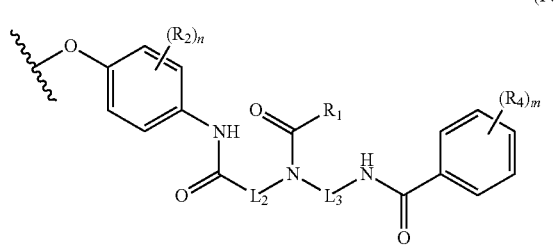

(IV)

wherein $L_2$, $L_3$, $R_1$, $R_2$, and n are as set forth above for formula (III), and $R_4$ at each occurrence is independently selected from $C_1$-$C_6$ alkyl (e.g., methyl) and m is 0, 1, 2, 3, 4, or 5. In certain embodiments, m is 0. In other embodiments, $R_4$ is a $C_1$-$C_5$ alkyl group (e.g., methyl) and m is 2.

In another embodiment, the Type B aglycone has the formula:

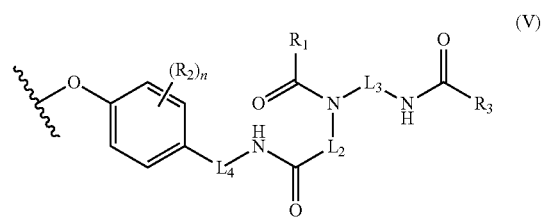

(V)

where $L_2$, $L_3$, $R_1$, $R_2$, $R_3$, and n are as set forth above for formula (III), and $L_4$ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_4$ is —$(CH_2)_n$—, where n is 1-6. In certain embodiments, $L_4$ is —$(CH_2)$—.

In certain embodiments, the Type B aglycone has the formula:

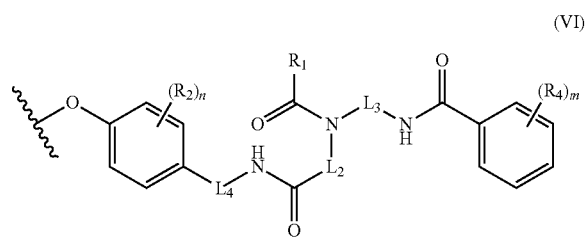

(VI)

where $L_2$, $L_3$, $L_4$, $R_1$, $R_2$, $R_4$, n, and m are as set forth above for formula (V).

Heavy atom derivatives. In certain embodiments, the reagents of the invention include their heavy atom derivatives (i.e., derivatives that include one or more heavy atom isotopes). The heavy atom derivatives are useful as internal standards for assays utilizing mass spectrometric analysis. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. As between an enzyme product and internal standard pair (e.g., MPS-II-P and MPS-II-IS), the reagents differ in mass and the difference in mass can be achieved through the use of additional (or fewer) atoms (e.g., changing the length of a portion of the compound by one or more methylenes for, for example, $L_1$, $L_2$, $L_3$, $L_4$, $R_1$, $R_2$, $R_3$, or $R_4$) or through the incorporation of heavy atoms (e.g., deuterium for hydrogen, $^{13}C$ for carbon, $^{15}N$ for nitrogen in, for example, $L_1$, $L_2$, $L_3$, $L_4$, $R_1$, $R_2$, $R_3$, or $R_4$).

Representative aglycones for substrate/internal standard pairs for MPS-I, II, IIIA, IIIB, IVA, VI, and VII reagents include the following:

for MPS-I substrate (referring to formula (IV)), $R_1$ is methyl, $R_2$ is hydrogen and n is 4, $L_2$ is —$CH_2CH_2$—, $L_3$ is —$(CH_2)_6$—, and $R_4$ is hydrogen and m is 5; for MPS-I internal standard, $R_1$ is methyl, $R_2$ is hydrogen and n is 4, $L_2$ is —$CH_2CH_2$—, $L_3$ is —$(CH_2)_6$—, and $R_4$ is deuterium and m is 5;

for MPS-II substrate (referring to formula (IV)), $R_1$ is n-butyl, $R_2$ is hydrogen and n is 4, $L_2$ is —$CH_2CH_2$—, $L_3$ is —$(CH_2)_6$—, and $R_4$ is hydrogen and m is 5; for MPS-II internal standard, $R_1$ is n-butyl, $R_2$ is hydrogen and n is 4, $L_2$ is —$CH_2CH_2$—, $L_3$ is —$(CH_2)_6$—, and $R_4$ is deuterium and m is 5;

for MPS-IIIA substrate (referring to formula (IV)), $R_1$ is ethyl, $R_2$ is hydrogen and n is 4, $L_2$ is —$CH_2CH_2$—, $L_3$ is —$(CH_2)_6$—, and $R_4$ is hydrogen and m is 5; for MPS-IIIA internal standard, $R_1$ is ethyl, $R_2$ is hydrogen and n is 4, $L_2$ is —$CH_2CH_2$—, $L_3$ is —$(CH_2)_6$—, $R_4$ is deuterium and m is 5;

for MPS-IIIB substrate (referring to formula (III)), $R_1$ is n-butyl, $R_2$ is hydrogen and n is 4, $L_2$ is —$CH_2CH_2$—, $L_3$ is —$(CH_2)_6$—, and $R_3$ is ethyl; for MPS-IIIB internal standard, $R_1$ is n-butyl, $R_2$ is deuterium and n is 4, $L_2$ is —$CH_2CH_2$—, $L_3$ is —$(CH_2)_6$—, $R_3$ is ethyl;

for MPS-IVA substrate (referring to formula (III)), $R_1$ is n-butyl, $R_2$ is hydrogen and n is 4, $L_2$ is —$CH_2CH_2$—, $L_3$ is —$(CH_2)_5$—, and $R_3$ is 3,5-dimethylphenyl; for MPS-IVA internal standard, $R_1$ is n-butyl, $L_2$ is —$CH_2CH_2$—, $L_3$ is —$(CH_2)_5$—, $R_3$ is 3,5-dimethylphenyl, and $R_2$ is deuterium and n is 4; and in an alternative embodiment, for MPS-IVA substrate, $R_1$ is n-pentyl, $R_2$ is hydrogen and n is 4, $L_2$ is —$CH_2CH_2$—, $L_3$ is —$(CH_2)_6$—, and $R_3$ is phenyl; for MPS-IVA internal standard, $R_1$ is n-pentyl, $R_2$ is hydrogen and n is 4, $L_2$ is —$CH_2CH_2$—, $L_3$ is —$(CH_2)_6$—, $R_3$ is $d_5$-phenyl;

for MPS-VI substrate (referring to formula (IV)), $R_1$ is n-butyl, $R_2$ is hydrogen and n is 4, $L_2$ is —$CH_2CH_2$—, $L_3$ is —$(CH_2)_5$—, and $R_4$ is hydrogen and m is 5; for MPS-VI internal standard, $R_1$ is n-butyl, $R_2$ is hydrogen and n is 4, $L_2$ is —$CH_2CH_2$—, $L_3$ is —$(CH_2)_5$—, and $R_4$ is deuterium and m is 5; and for MPS-VII substrate (referring to formula (III)), $R_1$ is butyl, $R_2$ is hydrogen and n is 4, $L_2$ is —$CH_2CH_2$—, $L_3$ is —$(CH_2)_6$—, and $R_3$ is propyl; for MPS-VII internal standard, $R_1$ is butyl, $R_2$ is deuterium and n is 4, $L_2$ is —$CH_2CH_2$—, $L_3$ is —$(CH_2)_6$—, and $R_3$ is propyl.

Salts. In certain embodiments, the reagents include amino groups (e.g., —$NH_2$), carboxylic acid groups (—$CO_2H$), sulfonic acid groups (e.g., —$OSO_3H$), and amidosulfonic acid groups (e.g., —$NHSO_3H$), which depending on the pH environment can become charged groups (e.g., —$NH_3^+$, —$OSO_2^-$, —$OSO_3^-$, —$NHSO_3^-$). It will be appreciated that the reagents of the invention include their salts (e.g., metal salts).

The preparation of representative MPS-I, II, IIIA, IIIB, IVA, and VI reagents are described in Examples 1, 4, and 5.

The following is a description of representative reagents (i.e., compounds) of the invention.

MPS-I Reagents

In one embodiment, the invention provides MPS-I reagents (S, P, and IS reagents) defined by the following formula:

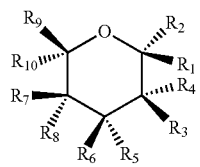

its salts and heavy atom derivatives thereof, wherein $R_1$=aglycone, $R_2$=H
or
$R_1$=H, $R_2$=aglycone
$R_3$=H, OH, $NH_2$ and $R_4$=H
or
$R_4$=H, OH, $NH_2$ and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=COOH and $R_{10}$=H
or
$R_{10}$=COOH and $R_9$=H with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

For the above compounds, the aglycone is as described above.

In certain embodiments of the MPS-I reagents defined above, the carbohydrate portion is replaced by a hydrogen atom; in this case a hydrogen atom is added to the aglycone. These reagents are representative of MPS-I enzyme products and internal standards.

In one embodiment, the sugar has the formula:

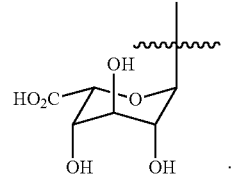

In certain embodiments, the compounds include amino groups (e.g., —$NH_2$) and carboxylic acid groups (—$CO_2H$), which depending on the pH environment can become charged groups (e.g., —$NH_3^+$ or —$CO_2^-$). It will be appreciated that the compounds of the invention include their salts (e.g., metal salts).

As noted above, the compounds of the invention include their heavy atom derivatives. The heavy atom derivatives are useful as internal standards. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

In certain embodiments of the MPS-I reagents defined above, the carbohydrate portion is replaced by a hydrogen atom; in this case a hydrogen atom is added to the aglycone. These reagents are representative of MPS-I enzyme products and internal standards.

Representative MPS-I reagents include the following compounds.

In certain embodiments, MPS-I substrates have the formula:

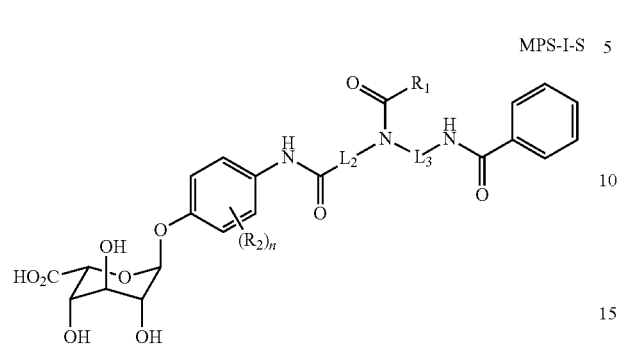

MPS-I-S where $L_2$, $L_3$, $R_1$, $R_2$, and n are as described above for formula (III).

In certain embodiments, MPS-I substrates have the formula:

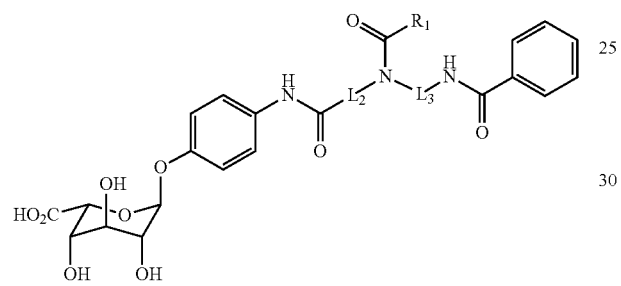

where $L_2$, $L_3$, and $R_1$ are as described above for formula (III).

A representative MPS-I substrate has the formula:

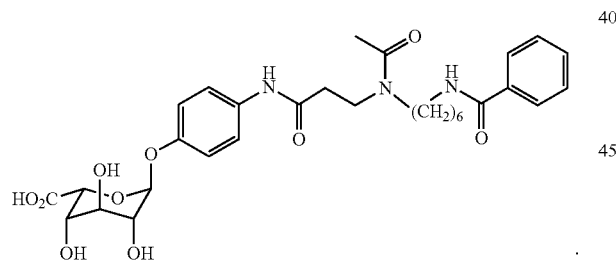

MPS-I products formed from the above substrate (MPS-I-S) have the formula:

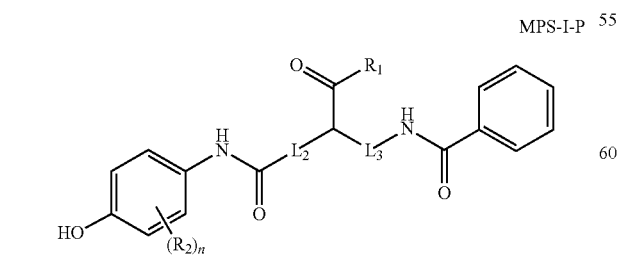

MPS-I-P where $L_2$, $L_3$, $R_1$, $R_2$, and n are as described above for formula (III).

A representative MPS-I product has the formula:

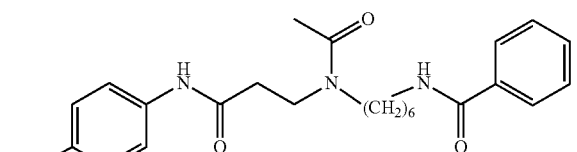

MPS-I internal standards useful for assaying products formed from the above substrate (MPS-I-S) have the formula:

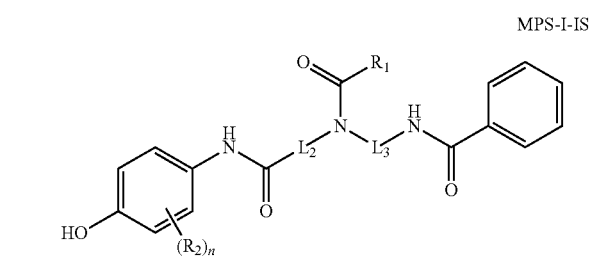

MPS-I-IS where $L_2$, $L_3$, $R_1$, $R_2$, and n are as described above for formula (III), and where the mass of MPS-I-IS differs from the mass of MPS-I-P such that the two are distinguishable by mass spectrometry. As noted above, MPS-I-IS can include one or more heavy atom isotopes (not shown in the structure above), or can have a structural variation (e.g., one or more of $L_2$, $L_3$, $R_1$, and $R_2$ for substrate differ from $L_2$, $L_3$, $R_1$, and $R_2$ for internal standard).

A representative MPS-I internal standard has the formula:

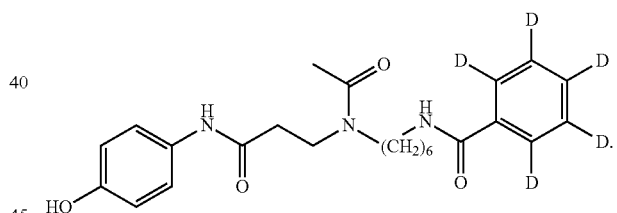

The representative MPS-I product derived from the representative MPS-I substrate can be assayed using the representative MPS-I internal standard.

MPS-II Reagents

In one embodiment, the invention provides MPS-II reagents (S, P, and IS reagents) defined by the following formula:

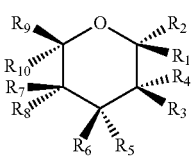

its salts and heavy atom derivatives thereof,
wherein
$R_1$=aglycone, $R_2$=H
or
$R_1$=H, $R_2$=aglycone $R_3$=OSO$_3$H, NHSO$_3$H and $R_4$=H
or
$R_4$=OSO$_3$H, NHSO$_3$H and $R_3$=H
$R_5$=H, OH, NH$_2$ and $R_6$=H
or
$R_6$=H, OH, NH$_2$ and $R_5$=H
$R_7$=H, OH, NH$_2$ and $R_8$=H
or
$R_8$=H, OH, NH$_2$ and $R_7$=H
$R_9$=COOH and $R_{10}$=H
or
$R_{10}$=COOH and $R_9$=H
with the proviso that only one of the pair of $R_5$ and $R_6$, and $R_7$ and $R_8$ can have each R group as hydrogen (i.e., the carbohydrate ring can include only a single methylene group (—CH$_2$—) in the ring).

For the above compounds, the aglycone is as described above.

In one embodiment, the sugar has the formula:

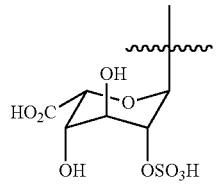

In another embodiment, the sugar has the formula:

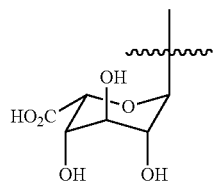

In certain embodiments, the compounds include amino groups (e.g., —NH$_2$), carboxylic acid groups (—CO$_2$H), and sulfonic acid groups (e.g., —OSO$_3$H), which depending on the pH environment can become charged groups (e.g., —NH$_3^+$, —CO$_2^-$, —OSO$_3^-$). It will be appreciated that the compounds of the invention include their salts (e.g., metal salts).

As noted above, the compounds of the invention include their heavy atom derivatives. The heavy atom derivatives are useful as internal standards. In further embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}$C for carbon, $^{15}$N for nitrogen).

The MPS-II enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}$C for carbon, $^{15}$N for nitrogen).

Representative MPS-II reagents include the following compounds.

In certain embodiments, MPS-II substrates have the formula:

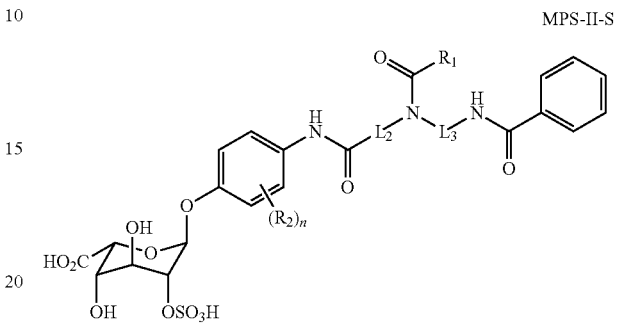

MPS-II-S where $L_2$, $L_3$, $R_1$, $R_2$, and n are as described above for formula (III).

In certain embodiments, MPS-II substrates have the formula:

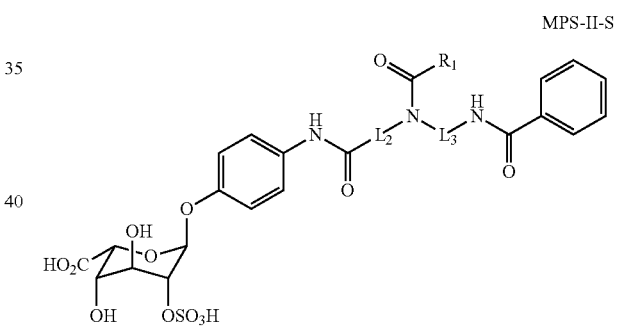

MPS-II-S where $L_2$, $L_3$, and $R_1$ are as described above for formula (III).

A representative MPS-II substrate has the formula:

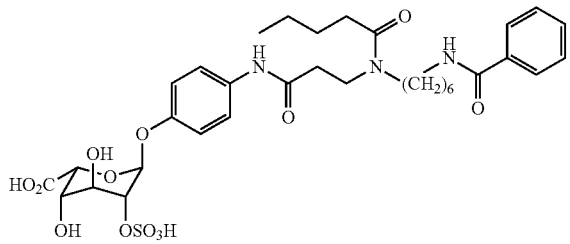

MPS-II products formed from the above substrate (MPS-II-S) have the formula:

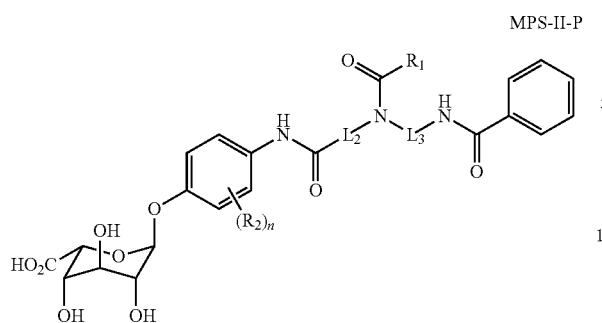

MPS-II-P where $L_2$, $L_3$, $R_1$, $R_2$, and n are as described above for formula (III).

A representative MPS-II product has the formula:

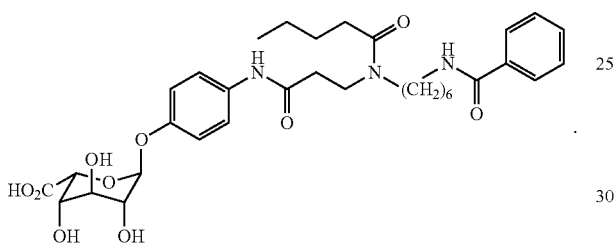

MPS-II internal standards useful for assaying products formed from the above substrate (MPS-II-S) have the formula:

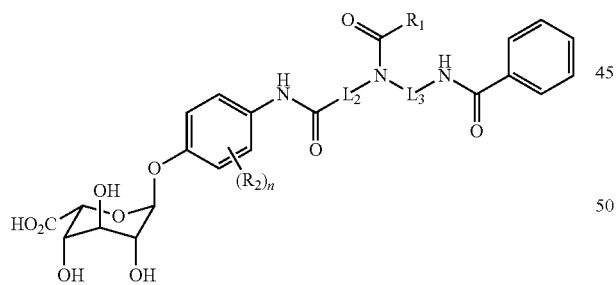

MPS-II-IS where $L_2$, $L_3$, $R_1$, $R_2$, and n are as described above for formula (III), and where the mass of MPS-II-IS differs from the mass of MPS-II-P such that the two are distinguishable by mass spectrometry. As noted above, MPS-II-IS can include one or more heavy atom isotopes (not shown in the structure above), or can have a structural variation (e.g., one or more of $L_2$, $L_3$, $R_1$, or $R_2$ for substrate differ from $L_2$, $L_3$, $R_1$, or $R_2$ for internal standard).

A representative MPS-II internal standard has the formula:

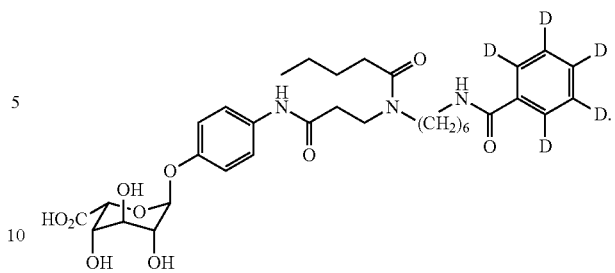

The representative MPS-II product derived from the representative MPS-II substrate can be assayed using the representative MPS-II internal standard.

MPS-IIIA Reagents

In another embodiment, the invention provides MPS-IIIA reagents (S, P, and IS reagents) defined by the following formula:

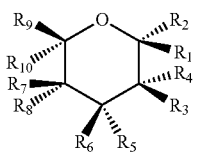

$R_1$=aglycone, $R_2$=H or $R_1$=H, $R_2$=aglycone $R_3$=H, OH, $NH_2$, $NHSO_3H$, $OSO_3H$ and $R_4$=H or $R_4$=H, OH, $NH_2$, $NHSO_3H$, $OSO_3H$ and $R_3$=H $R_5$=H, OH, $NH_2$ and $R_6$=H or $R_6$=H, OH, $NH_2$ and $R_5$=H $R_7$=H, OH, $NH_2$ and $R_8$=H or $R_8$=H, OH, $NH_2$ and $R_7$=H $R_9$=$CH_2OH$, $CH_2NH_2$ and $R_{10}$=H or $R_{10}$=$CH_2OH$, $CH_2NH_2$ and $R_9$=H its salts and heavy atom derivatives thereof, wherein the aglycone is as described above, and with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

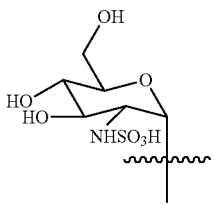

In another embodiment, the sugar has the formula:

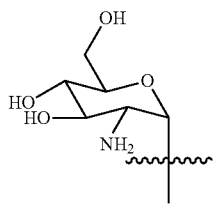

In certain embodiments, the compounds include amino groups (e.g., —$NH_2$) and amidosulfonic acid groups (e.g., —$NHSO_3H$), which depending on the pH environment can become charged groups (e.g., —$NH_3^+$, —$NHSO_3^-$). It will be appreciated that the compounds of the invention include their salts (e.g., metal salts).

The MPS-IIIA enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IIIA reagents include the following compounds.

In certain embodiments, MPS-IIIA substrates have the formula:

MPS-IIIA-S

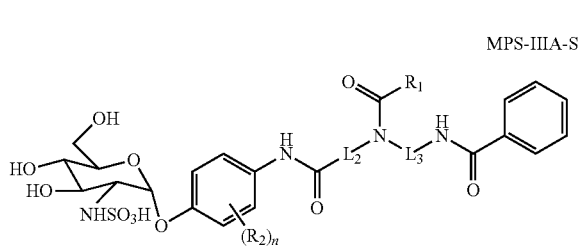

where $L_2$, $L_3$, $R_1$, $R_2$, and n are as described above for formula (III).

In certain embodiments, MPS-IIIA substrates have the formula:

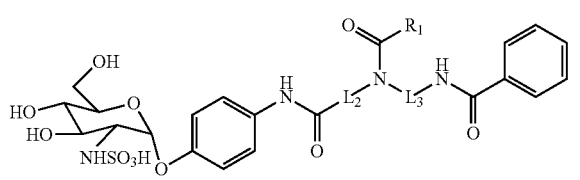

where $L_2$, $L_3$, and $R_1$ are as described above for formula (III).

A representative MPS-IIIA substrate has the formula:

MPS-IIIA products formed from the above substrate (MPS-IIIA-S) have the formula:

MPS-IIIA-P

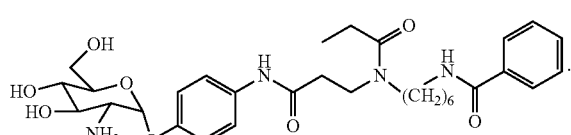

where $L_2$, $L_3$, $R_1$, $R_2$, and n are as described above for formula (III).

A representative MPS-IIIA product has the formula:

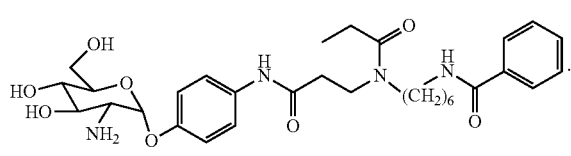

MPS-IIIA internal standards useful for assaying products formed from the above substrate (MPS-IIIA-S) have the formula:

MPS-IIIA-IS

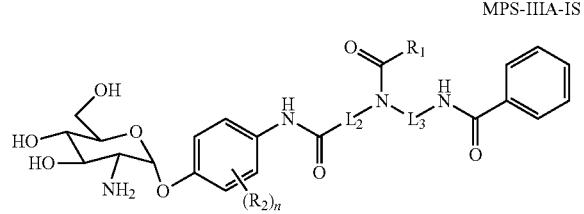

where $L_2$, $L_3$, $R_1$, $R_2$, and n are as described above for formula (III), and where the mass of MPS-IIIA-IS differs from the mass of MPS-IIIA-P such that the two are distinguishable by mass spectrometry. As noted above, MPS-IIIA-IS can include one or more heavy atom isotopes (not shown in the structure above), or can have a structural variation (e.g., one or more of $L_2$, $L_3$, $R_1$, $R_2$ for substrate differ from $L_2$, $L_3$, $R_1$, $R_2$ for internal standard).

A representative MPS-IIIA internal standard has the formula:

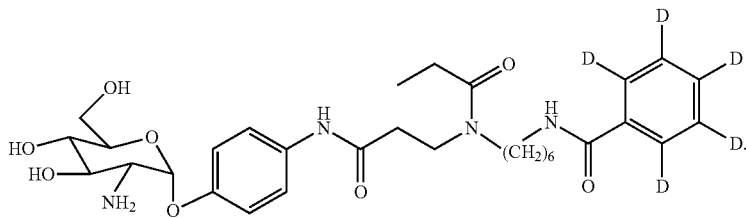

The representative MPS-IIIA product derived from the representative MPS-IIIA substrate can be assayed using the representative MPS-IIIA internal standard.

MPS-IIIB Reagents

In a further embodiment, the invention provides MPS-IIIB reagents (S, P, and IS reagents) defined by the following formula:

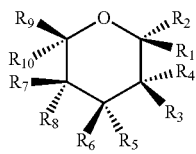

$R_1$=aglycone, $R_2$=H
or
$R_1$=H, $R_2$=aglycone
$R_3$=H, OH, $NH_2$, $NHR_{11}$, where $R_{11}$=formyl, acetyl, C=O (($CH_2)_n CH_3$) with n=1-6 and $R_4$=H
or
$R_4$=H, OH, $NH_2$, $NHR_{11}$, where $R_{11}$=formyl, acetyl, C=O (($CH_2)_n CH_3$) with n=1-6 and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=$CH_2OH$, $CH_2NH_2$ and $R_{10}$=H
or
$R_{10}$=$CH_2OH$, $CH_2NH_2$ and $R_{10}$=H its salts and heavy atom derivatives thereof,
wherein the aglycone is as described above, and
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In certain embodiments of the MPS-IIIB reagents defined above, the carbohydrate portion is replaced by a hydrogen atom; in this case a hydrogen atom is added to the aglycone. These reagents are representative of MPS-IIIB enzyme products and internal standards.

In one embodiment, the sugar has the formula:

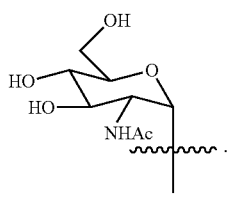 [SMILES: *C1OC(CO)C(O)C(O)C1NC(C)=O]

In the above formula, "NHAc" refers to "NH-C(=O)$CH_3$."

In certain embodiments, the compounds include amino groups (e.g., —$NH_2$), which depending on the pH environment can become charged groups (e.g., —$NH_3^+$). It will be appreciated that the compounds of the invention include their salts (e.g., metal salts).

The MPS-IIIB enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IIIB reagents include the following compounds.

In certain embodiments, MPS-IIIB substrates have the formula:

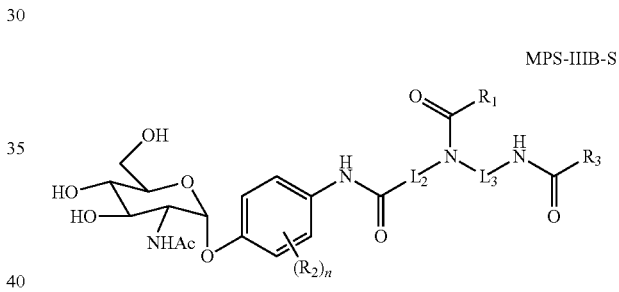

MPS-IIIB-S where $L_2$, $L_3$, $R_1$, $R_2$, $R_3$, and n are as described above for formula (III).

In certain embodiments, MPS-IIIB substrates have the formula:

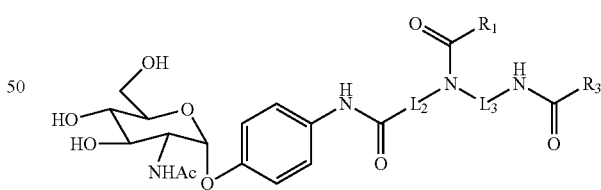

where $L_2$, $L_3$, $R_1$, and $R_3$ are as described above for formula (III).

A representative MPS-IIIB substrate has the formula:

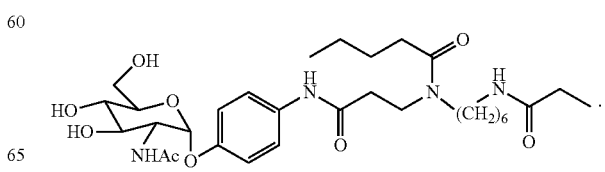

MPS-IIIB products formed from the above substrate (MPS-IIIB-S) have the formula:

MPS-IIIB-P

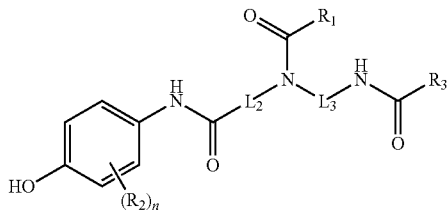

where $L_2$, $L_3$, $R_1$, $R_2$, $R_3$, and n are as described above for formula (III).

A representative MPS-IIIB product has the formula:

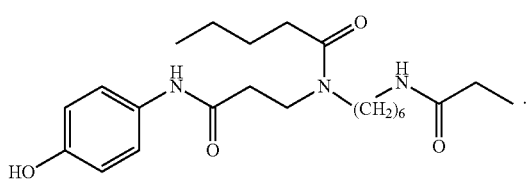

MPS-IIIB internal standards useful for assaying products formed from the above substrate (MPS-IIIB-S) have the formula:

MPS-IIIB-IS

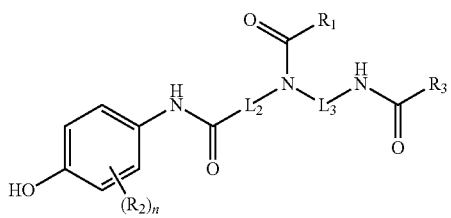

where $L_2$, $L_3$, $R_1$, $R_2$, $R_3$, and n are as described above for formula (III), and where the mass of MPS-IIIB-IS differs from the mass of MPS-IIIB-P such that the two are distinguishable by mass spectrometry. As noted above, MPS-IIIB-IS can include one or more heavy atom isotopes (not shown in the structure above), or can have a structural variation (e.g., one or more of $L_2$, $L_3$, $R_1$, $R_2$, or $R_3$ for substrate differ from $L_2$, $L_3$, $R_1$, $R_2$, or $R_3$ for internal standard).

A representative MPS-IIIB internal standard has the formula:

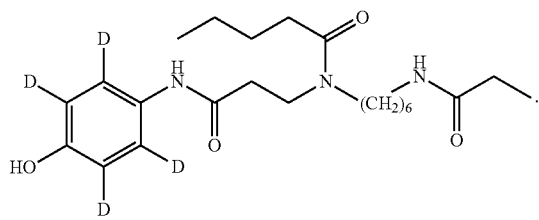

The representative MPS-IIIB product derived from the representative MPS-IIIB substrate can be assayed using the representative MPS-IIIB internal standard.

MPS-IVA Reagents

In another embodiment, the invention provides MPS-IVA reagents (S, P, and IS reagents) defined by the following formula:

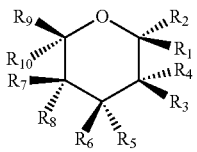

$R_1$=aglycone, $R_2$=H or $R_1$=H, $R_2$=aglycone $R_3$=H, OH, $NH_2$, $NHR_{11}$, where $R_{11}$=formyl, acetyl, C=O $((CH_2)_n CH_3)$ with n=1-6 and $R_4$=H or $R_4$=H, OH, $NH_2$, $NHR_{11}$, where $R_{11}$=formyl, acetyl, C=O$((CH_2)_n CH_3)$ with n=1-6 and $R_3$=H $R_5$=H, OH, $NH_2$ and $R_6$=H or $R_6$=H, OH, $NH_2$ and $R_5$=H $R_7$=H, OH, $NH_2$ and $R_8$=H or $R_8$=H, OH, $NH_2$ and $R_7$=H $R_9$=$CH_2OH$, $CH_2OSO_3H$, $CH_2NH_2$, $CH_2NHSO_3H$ and $R_{10}$=H or $R_{10}$=$CH_2OH$, $CH_2OSO_3H$, $CH_2NH_2$, $CH_2NHSO_3H$ and $R_9$=H its salts and heavy atom derivatives thereof, wherein the aglycone is as described above, and with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

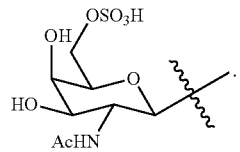

In certain embodiments, the compounds include amino groups (e.g., —$NH_2$) and sulfonic acid groups (e.g., —$OSO_3H$), which depending on the pH environment can become charged groups (e.g., —$NH_3^+$, —$OSO_3^-$). It will be appreciated that the compounds of the invention include their salts (e.g., metal salts).

The MPS-IVA enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IVA reagents include the following compounds.

In certain embodiments, MPS-IVA substrates have the formula:

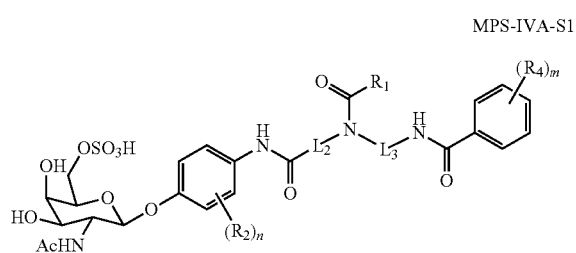

MPS-IVA-S1 where $L_2$, $L_3$, $R_1$, $R_2$, and n are as described above for formula (III). $R_4$ at each occurrence is independently selected from $C_1$-$C_6$ alkyl (e.g., methyl) and m is 0, 1, 2, 3, 4, or 5.

In other embodiments, MPS-IVA substrates have the formula:

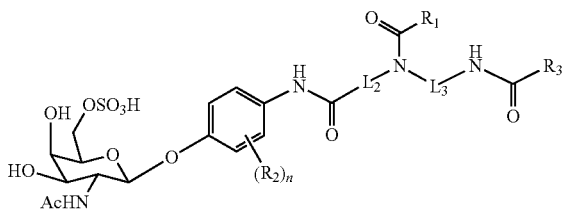

MPS-IVA-S2 where $L_2$, $L_3$, $R_1$, $R_2$, $R_3$, and n are as described above for formula (III).

In certain embodiments, MPS-IVA substrates have the formula:

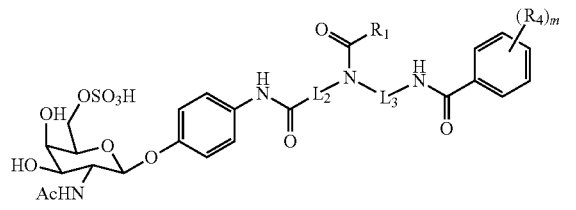

where $L_2$, $L_3$, $R_1$, $R_4$, and m are as described above for formula (IV).

In other embodiments, MPS-IVA substrates have the formula:

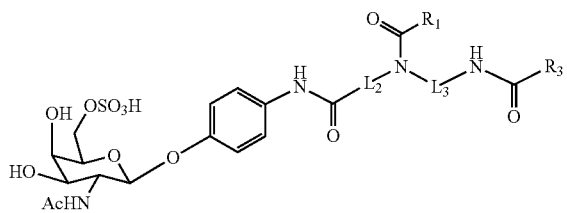

where $L_2$, $L_3$, $R_1$, and $R_3$ are as described above for formula (III).

A representative MPS-IVA substrate has the formula:

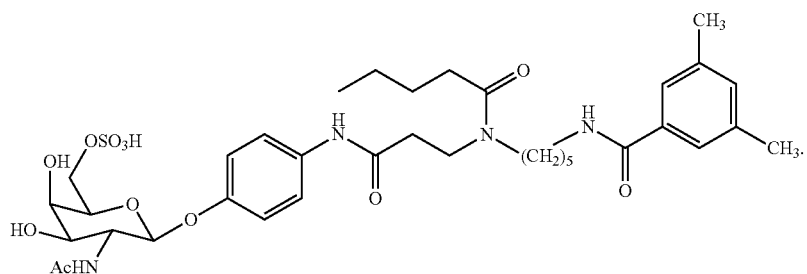

Another representative MPS-IVA substrate has the formula:

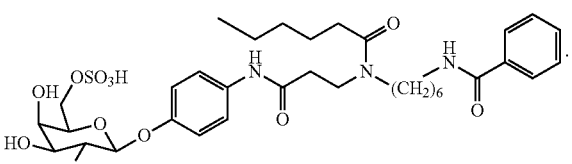

MPS-IVA products formed from the above substrate (MPS-IVA-S1) have the

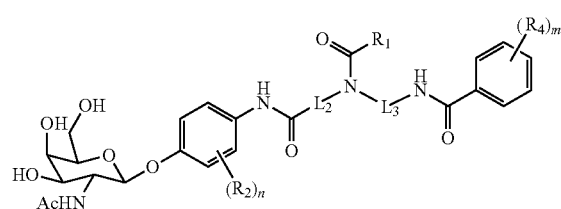

MPS-IVA-P1 where $L_2$, $L_3$, $R_1$, $R_2$, $R_4$, n, and m are as described above in formula (IV).

In another embodiment, MPS-IVA products formed from the above substrate (MPS-IVA-S2) have the formula:

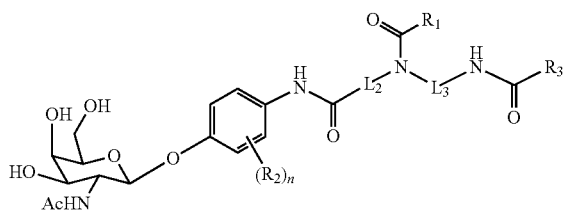

MPS-IVA-P2 where $L_2$, $L_3$, $R_1$, and $R_3$ are as described above for formula (III).

A representative MPS-IVA product has the formula:

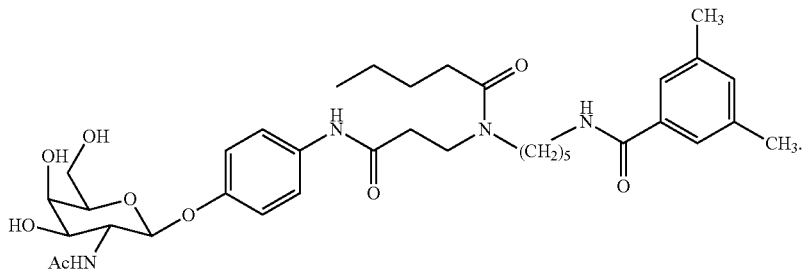

Another representative MPS-WA product has the formula:

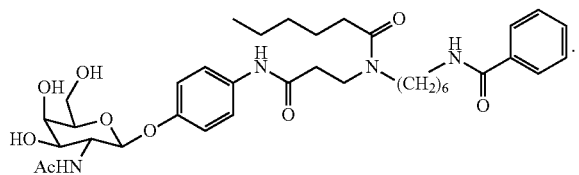

MPS-IVA internal standards useful for assaying products formed from the above substrates (MPS-IVA-S1 and MPS-WA-S2) have the formulae:

MPS-IVA-IS1

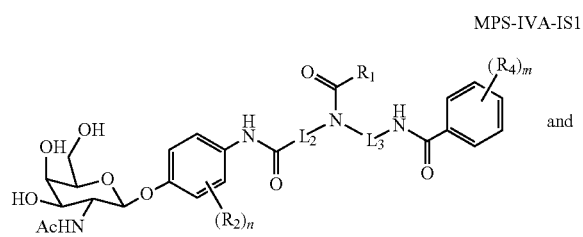

and

-continued

MPS-IVA-IS2

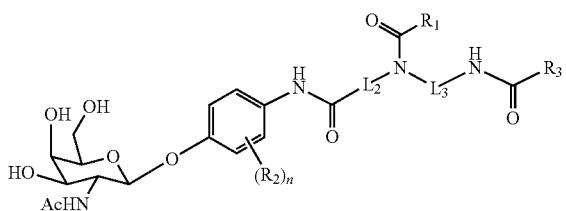

where $L_2$, $L_3$, $R_1$, $R_2$, $R_3$, $R_4$, n, and m are as described above, and the masses of MPS-IVA-IS1 and MPS-IVA-IS2 differ from the masses of MPS-IVA-P1 and MPS-IVA-P2, respectively, such that the two are distinguishable by mass spectrometry. As noted above, MPS-IVA-IS1 and MPS-IVA-IS2 can include one or more heavy atom isotopes (not shown in the structure above), or can have a structural variation (e.g., one or more of $L_2$, $L_3$, $R_1$, $R_2$, $R_3$, or $R_4$ for substrate differ from $L_2$, $L_3$, $R_1$, $R_2$, $R_3$, or $R_4$ for internal standard).

A representative MPS-IVA internal standard has the formula:

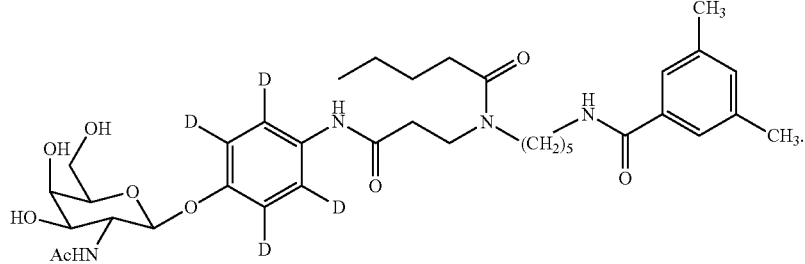

Another representative MPS-WA internal standard has the formula:

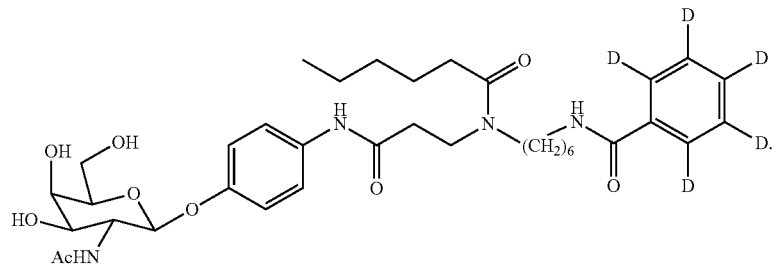

Representative MPS-IVA products derived from the representative MPS-IVA substrates can be assayed using the representative MPS-IVA internal standards.

A further representative set of MPS-IVA reagents is described below.

A further representative MPS-IVA substrate has the formula:

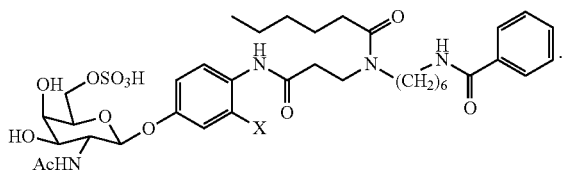

A further representative MPS-IVA product standard has the formula:

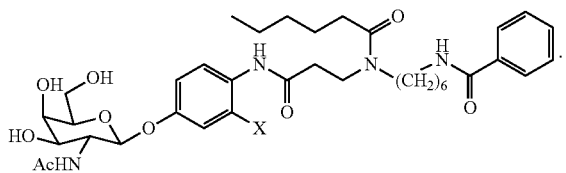

A further representative MPS-IVA internal standard has the formula:

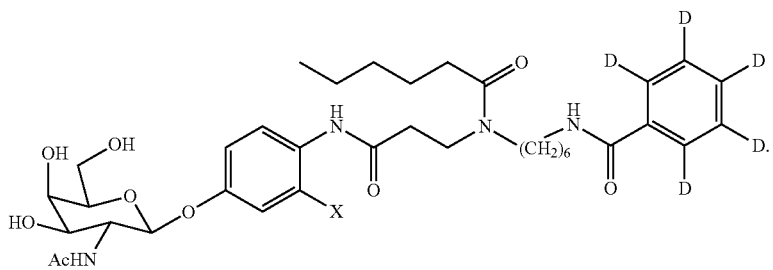

In the above formulas, X is selected from fluoro, methyl, and methoxy.

MPS-VI Reagents

In another embodiment, the invention provides MPS-VI reagents (S, P, and IS reagents) defined by the following formula:

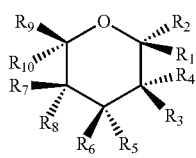

$R_1$=aglycone, $R_2$=H
or
$R_1$=H, $R_2$=aglycone
$R_3$=H, OH, $NH_2$, $NHR_{11}$, where $R_{11}$=formyl, acetyl, $C=O((CH_2)_nCH_3)$ with n=1-6 and $R_4$=H
or
$R_4$=H, OH, $NH_2$, $NHR_{11}$, where $R_{11}$=formyl, acetyl, $C=O((CH_2)_nCH_3)$ with n=1-6 and $R_3$=H $R_5$=H, OH, $NH_2$ and $R_6$=H
or
$R_6$=H, OH, $NH_2$ and $R_5$=H
$R_7$=$CH_2OH$, $CH_2OSO_3H$, $CH_2NH_2$, $CH_2NHSO_3H$ and $R_8$=H
or
$R_8$=$CH_2OH$, $CH_2OSO_3H$, $CH_2NH_2$, $CH_2NHSO_3H$ and $R_7$=H
$R_9$=$CH_2OH$, $CH_2NH_2$ and $R_{10}$=H
or
$R_{10}$=$CH_2OH$, $CH_2NH_2$ and $R_9$=H its salts and heavy atom derivatives thereof,
wherein the aglycone is as described above, and
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

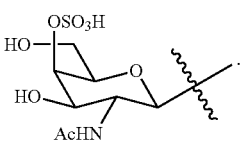

In another embodiment, the sugar has the formula:

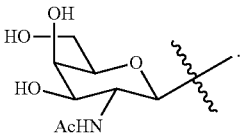 [SMILES: *C1OC(CO)C(O)C(O)C1NC(C)=O]

In the above formulas, "AcNH" refers to "$CH_3C(=O)NH$."

In certain embodiments, the compounds include amino groups (e.g., —$NH_2$) and sulfonic acid groups (e.g., —$OSO_3H$), which depending on the pH environment can become charged groups (e.g., —$NH_3^+$, —$OSO_3^-$). It will be appreciated that the compounds of the invention include their salts (e.g., metal salts).

The MPS-VI enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-VI reagents include the following compounds.

In certain embodiments, MPS-VI substrates have the formula:

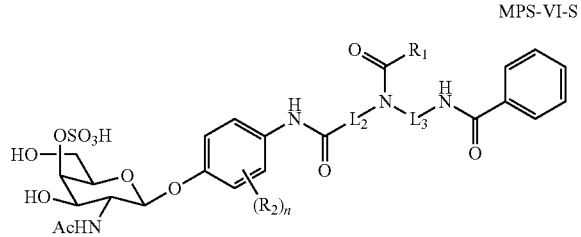
MPS-VI-S where $L_2$, $L_3$, $R_1$, $R_2$, and n are as described above for formula (III).

In certain embodiments, MPS-VI substrates have the formula:

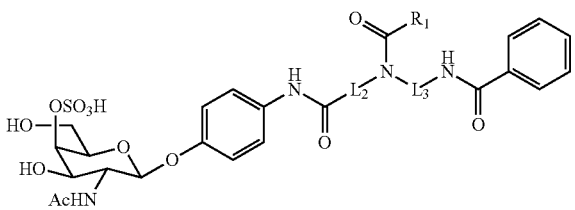

where $L_2$, $L_3$, and $R_1$ are as described above for formula (III).

A representative MPS-VI substrate has the formula:

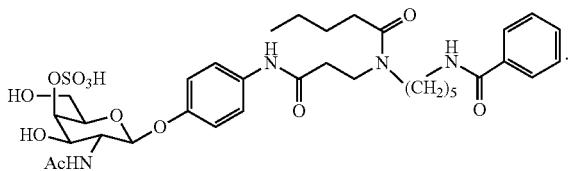

MPS-VI products formed from the above substrate (MPS-VI-S) have the formula:

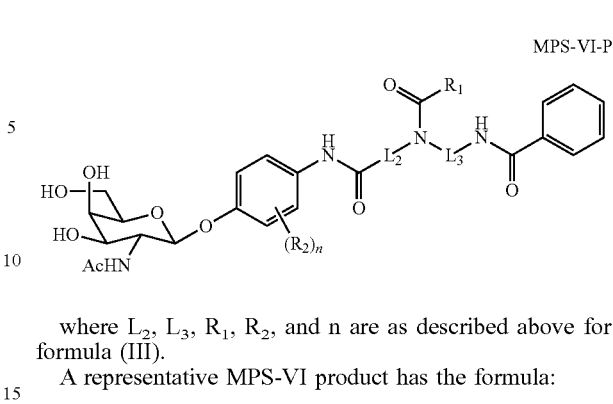
MPS-VI-P where $L_2$, $L_3$, $R_1$, $R_2$, and n are as described above for formula (III).

A representative MPS-VI product has the formula:

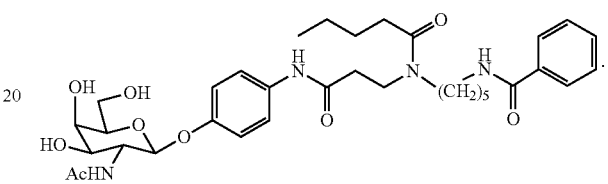

MPS-VI internal standards useful for assaying products formed from the above substrate (MPS-VI-S) have the formula:

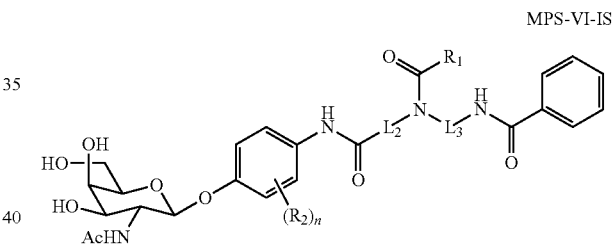
MPS-VI-IS where $L_2$, $L_3$, $R_1$, $R_2$, and n are as described above for formula (III), and where the mass of MPS-VI-IS differs from the mass of MPS-VI-P such that the two are distinguishable by mass spectrometry. As noted above, MPS-VI-IS can include one or more heavy atom isotopes (not shown in the structure above), or can have a structural variation (e.g., one or more of $L_2$, $L_3$, $R_1$, or $R_2$ for substrate differ from $L_2$, $L_3$, $R_1$, or $R_2$ for internal standard).

A representative MPS-VI internal standard has the formula:

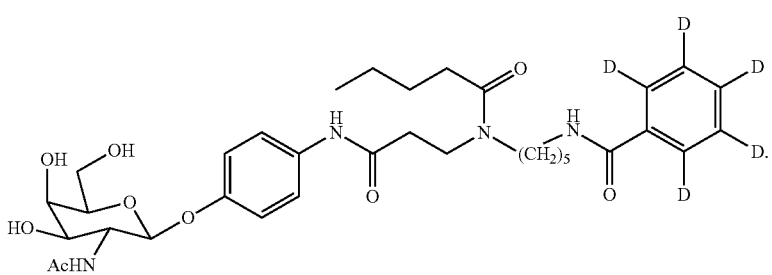

The representative MPS-VI product derived from the representative MPS-VI substrate can be assayed using the representative MPS-VI internal standard.

MPS-VII Reagents

In one embodiment, the invention provides MPS-VII reagents (S, P, and IS reagents) defined by the following formula:

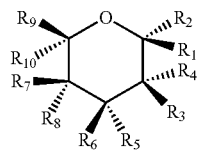

its salts and heavy atom derivatives thereof,
wherein
$R_1$=aglycone, $R_2$=H
or
$R_1$=H, $R_2$=aglycone
$R_3$=H, OH, $NH_2$ and $R_4$=H
or
$R_4$=H, OH, $NH_2$ and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=COOH and $R_{10}$=H
or
$R_{10}$=COOH and $R_9$=H
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

For the above compounds, the aglycone is as described above.

In certain embodiments of the MPS-VII reagents defined above, the carbohydrate portion is replaced by a hydrogen atom; in this case a hydrogen atom is added to the aglycone. These reagents are representative of MPS-VII enzyme products and internal standards.

In one embodiment, the sugar has the formula:

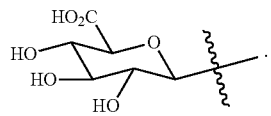

In certain embodiments, the compounds include amino groups (e.g., —$NH_2$) and carboxylic acid groups (—$CO_2H$), which depending on the pH environment can become charged groups (e.g., —$NH_3^+$ or —$CO_2^-$). It will be appreciated that the compounds of the invention include their salts (e.g., metal salts).

As noted above, the compounds of the invention include their heavy atom derivatives. The heavy atom derivatives are useful as internal standards. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

In certain embodiments of the MPS-VII reagents defined above, the carbohydrate portion is replaced by a hydrogen atom; in this case a hydrogen atom is added to the aglycone. These reagents are representative of MPS-VII enzyme products and internal standards.

Representative MPS-VII reagents include the following compounds.

In certain embodiments, MPS-VII substrates have the formula:

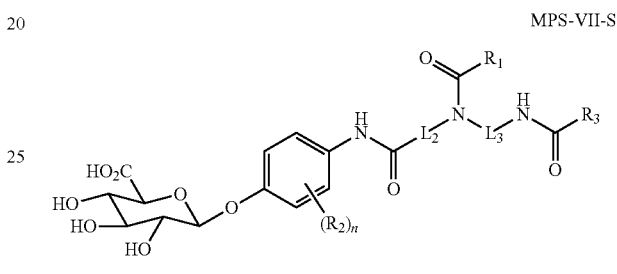

MPS-VII-S where $L_2$, $L_3$, $R_1$, $R_2$, $R_3$, and n are as described above for formula (III).

In certain embodiments, MPS-VII substrates have the formula:

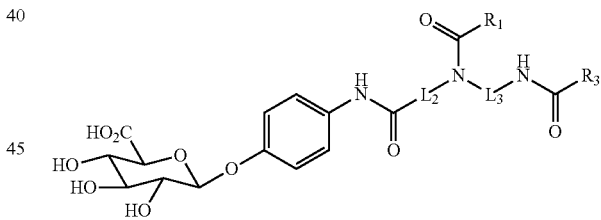

where $L_2$, $L_3$, $R_1$, and $R_3$ are as described above for formula (III).

A representative MPS-VII substrate has the formula:

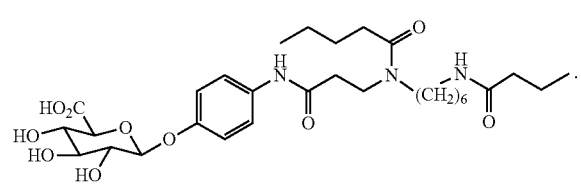

MPS-VII products formed from the above substrate (MPS-VII-S) have the formula:

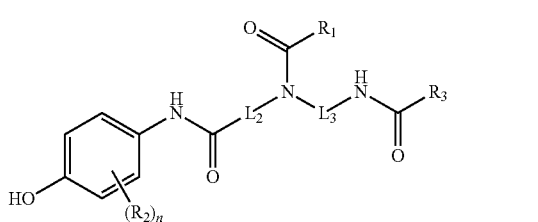

MPS-VII-P where $L_2$, $L_3$, $R_1$, $R_2$, $R_3$, and n are as described above for formula (III).

A representative MPS-VII product has the formula:

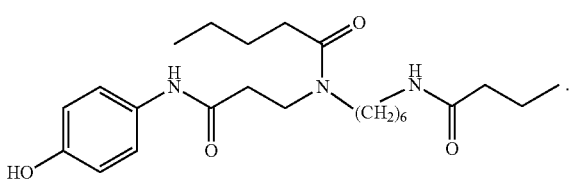

MPS-VII internal standards useful for assaying products formed from the above substrate (MPS-VII-S) have the formula:

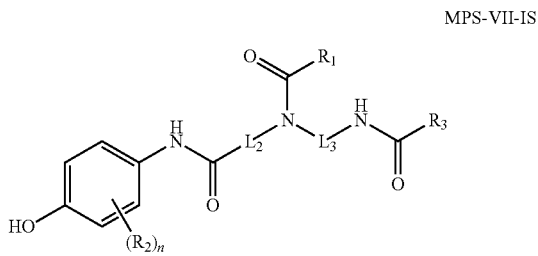

MPS-VII-IS where $L_2$, $L_3$, $R_1$, $R_2$, $R_3$, and n are as described above for formula (III), and where the mass of MPS-VII-IS differs from the mass of MPS-VII-P such that the two are distinguishable by mass spectrometry. As noted above, MPS-VII-IS can include one or more heavy atom isotopes (not shown in the structure above), or can have a structural variation (e.g., one or more of $L_2$, $L_3$, $R_1$, $R_2$, or $R_3$ for substrate differ from $L_2$, $L_3$, $R_1$, $R_2$, or $R_3$ for internal standard).

A representative MPS-VII internal standard has the formula:

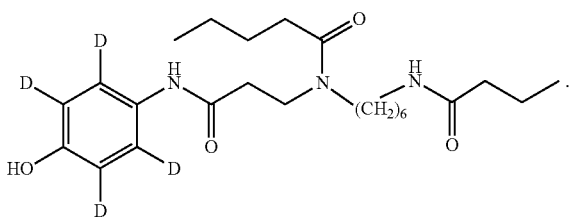

The representative MPS-VII product derived from the representative MPS-VII substrate can be assayed using the representative MPS-VII internal standard.

Reagent Kits

The reagents of the invention can be advantageously combined into kits to perform enzyme assays. Reagent kits for a particular assay include the appropriate enzyme substrate and internal standard pair (e.g., MPS-II-S and MPS-II-IS). In certain embodiments, the kits include more than one substrate/internal standard pair and can be used to assay more than one enzyme (i.e., multiplex assay in which two, three, four, five, or six enzymes can be assayed in a single screen). In other embodiments, the kits further include buffers for performing the assays. In other embodiments, the kits further include the enzymatic products, which can be used for tuning the mass spectrometer. In other embodiments, the kits further include quality control dried blood spots. Instructions for performing the assays can also be included in the kits.

Enzyme Assays

The reagents of the invention can be advantageously utilized to assay enzymes associated with a lysosomal storage disease. In the assays, one or more substrates (S) are incubated in a suitable buffer with a suitable source of enzymes such as a dried blood spot from a newborn screening card or a urine sample for a sufficient time to form one or more products (P) that are subsequently detected by tandem mass spectrometry. The assay also makes used of an internal standard (IS), which in certain embodiments are chemically identical to the enzyme-formed product, but has a different mass (e.g., heavy isotope substituted such as deuterium and/or carbon-13 substitutions). The incubation is done in a suitable buffer to allow the enzymatic reactions to proceed (e.g., 100 mM ammonium formate pH 4.5 containing 5 mM barium acetate and 7.5 mM cerium acetate).

Enzymes that are advantageously assayed with the reagents of the invention include the following:

(a) alpha-L-iduronidase, which acts on the substrate of MPS-I to produce the MPS-I product, and the assay makes use of the MPS-I internal standard;

(b) iduronate-2-sulfatase, which acts on the substrate of MPS-II to produce the MPS-II product, and the assay makes use of the MPS-II internal standard;

(c) heparan N-sulfatase, which acts on the substrate of MPS-IIIA to produce the MPS-IIIA product, and the assay makes use of the MPS-IIIA internal standard;

(d) N-acetyl-alpha-D-glucosaminidase, which acts on the substrate of MPS-IIIB to produce the MPS-IIIB product, and the assay makes use of the MPS-IIIB internal standard;

(e) N-acetylgalactosamine-6-sulfate-sulfatase, which acts on the substrate of MPS-IVA to produce the MPS-WA product, and the assay makes use of the MPS-IVA internal standard;

(f) N-acetylgalactosamine-4-sulfate-sulfatase, which acts on the substrate of MPS-VI to produce the MPS-VI product, and the assay makes use of the MPS-VI internal standard; and (g) beta-glucuronidase, which acts on the substrate of MPS-VII to produce the MPS-VII product, and the assay makes use of the MPS-VII internal standard.

Representative methods for assaying the enzymes noted above are described in WO 2009/026252 (PCT/US2008/073516), WO 2010/081163 (PCT/US2010/020801), WO 2012/027612 (PCT/US2011/049224), and WO 2013/070953 (PCT/US2012/064205), each expressly incorporated herein by reference in its entirety. The reagents of the invention can be advantageously utilized in these methods.

Representative assays using the MPS-I, II, IIIA, IIIB, IVA, and VI reagents of the invention are described in Examples 1-11.

The assays of the invention can include variations without departing from the invention. Several variations are described below.

In a first embodiment, substrate and internal standard are incubated in assay buffer with enzyme source, followed by quench (e.g., addition of acetonitrile) and then mass spectrometric analysis (e.g., LC/MSMS) and quantification of the sugar-aglycone product and internal standard (note that for MPS-I, MPS-IIIB, and MPS-VII, the product is the aglycone (with added hydrogen)).

In a second embodiment, the assay is as described in the first embodiment with the exception that the enzymatic reaction mixture is extracted (optionally without quench) with an organic solvent (e.g., ethyl acetate) suitable for extracting the product and internal standard, the extracted mixture concentrated to dryness and then taken up in a solvent suitable for flow injection mass spectrometric analysis (e.g., FIA/MSMS).

In a third embodiment, the assay is as described in the second embodiment with the exception that a suspension of anion exchange resin is added during the quench to trap the substrate.

In a fourth embodiment, the assay is as described in the first embodiment with the exception that a second enzyme (e.g., a glycohydrolase, such as bacterial beta-N-acetylgalactoaminidase) suitable for cleaving the initial sulfatase product (sugar-aglycone with the sulfate removed) but not cleaving the substrate is added in the assay cocktail (substrate and internal standard). Following extraction, concentration, and resolubilization, mass spectrometric analysis (e.g., FIA/MSMS) is carried out leading to the quantification of the aglycone product and internal standard. In some cases there may be an enzyme that is endogenous in the dried blood spot sample that can act on the sulfated-sugar-aglycone substrate to cleave the glycosidic linkage (i.e. human hexosaminidase A). In this case an inhibitor of this endogenous enzyme may be added to block the action of the endogenous enzyme on the added substrate. This inhibitor is chosen so as to not block the action of the glycohydrolase added to the assay.

In a fifth embodiment, the assay is as described in the second embodiment with the exception that a second enzyme (e.g., a glycohydrolase) suitable for cleaving selective sulfatase sugar-aglycone substrates is added in the assay cocktail (substrate and internal standard). Following quench, mass spectrometric analysis (e.g., LC/MSMS) is used to quantify the aglycone product and internal standard. In a modification of this embodiment, an inhibitor of an endogenous activity (e.g., human hexosaminidase A) is also added to the assay cocktail.

In a sixth embodiment, substrate and internal standard are incubated in assay buffer with enzyme source, then a buffer is added to shift the pH (e.g., to pH 6) to optimize the activity of a second enzyme (e.g., a glycohydrolase), followed by addition of the glycohydrolase (e.g., bacterial beta-N-acetylgalactoaminidase) and incubation (e.g., 1-2 hrs). The sample is then quenched, and mass spectrometric analysis (e.g., LC/MSMS) is used to quantify the aglycone product and internal standard. In a modification of this embodiment, an inhibitor of an endogenous enzyme activity (e.g., human hexosaminidase A) is also added to the assay cocktail.

In a seventh embodiment, the assay is as described in the sixth embodiment with the exception that the enzymatic reaction mixture is extracted (optionally without quench) with an organic solvent (e.g., ethyl acetate) suitable for extracting the product and internal standard, the extracted mixture concentrated to dryness and then taken up in a solvent suitable for flow injection analysis (e.g., FIA/MSMS). In a modification of this embodiment, an inhibitor of an endogenous enzyme activity (e.g., human hexosaminidase A) is also added to the assay cocktail.

In an eighth embodiment, for the embodiments above that utilize extraction with an organic solvent to isolate product and internal standard, after removal of the solvent a solution of a suitable acylating agent (e.g. acetic anhydride) and suitable base (e.g., triethylamine) in a suitable solvent is added and the resulting combination incubated (1-2 hr) to provide acylated (e.g., acetylated) aglycone products and internal standards having increased sensitivity in MS analysis.

In a ninth embodiment, the assay is as described in the eighth embodiment with the exception that the acylating agent and base are included in the extraction (e.g., ethyl acetate) solvent to cause the aglycone and internal standard to become acylated (e.g., acetylated) during the extraction process or after the extract is allowed to incubate (e.g., for 1-2 hrs).

In a tenth embodiment, substrate and second enzyme (glycohydrolase) are incubated in assay buffer with enzyme source, followed by quench, and then fluorescence analysis to quantitate fluorescent product. In a modification of this embodiment, an inhibitor of an endogenous enzyme activity (e.g., human hexosaminidase A) is also added to the assay cocktail. For this embodiment, substrates with Type A aglycone are used.

In an eleventh embodiment, substrate is incubated in assay buffer with enzyme source, then a buffer is added to shift the pH (e.g., to pH 6) to optimize activity of a second enzyme (e.g., a glycohydrolase), followed by addition of the glycohydrolase (e.g., bacterial beta-N-acetylgalactoaminidase) and incubation (e.g., 1-2 hrs), then quench and fluorescence analysis quantification of the fluorescent product. In a modification of this embodiment, an inhibitor of an endogenous enzyme activity (e.g., human hexosaminidase A) is also added to the assay cocktail. For this embodiment, substrates with Type A aglycone are used.

In certain embodiments, additional assay options are also included within the methods of the invention. Two options are described below.

Assay option 1. After the incubation of the desired set of substrates with enzyme source in a suitable buffer, the reaction is subjected to liquid-liquid extraction with a suitable solvent such as ethyl acetate. If MPS-II is assayed without use of the second enzyme (glycohydrolase) to generate the aglycone, the mixture should be acidified to pH about 2-3 with a suitable acid such as citric acid so that the carboxylate group of the MPS-II-P will be protonated and better extract into ethyl acetate. If the second enzyme is used in this assay to remove the sugar, the aglycone will extract well into the solvent without acidification because it does not have a carboxy group. The purpose of the liquid-liquid extraction step is 2-fold: (1) extraction leads to removal of most of the buffer salts, which would interfere with the ionization process in the mass spectrometer; and (2) extraction leads to extraction of most of the enzyme products with minimal extraction of the enzyme substrates. This is useful because the substrates can partially decompose by loss of sulfate in the ionization source of the mass spectrometer to form product, and it is only the product generated enzymatically that one desires to quantify. After liquid-liquid extraction, the ethyl acetate layer is transferred to a new container and solvent is removed by evaporation. The residue is taken up in a solvent suitable for injection into the mass spectrometer. An example solvent is aqueous ammonium formate/methanol mixtures. The products and internal standards are detected in multiple reaction monitoring mode in which the precursor ion is isolated in the first quadrupole and is then subjected to collision-induced dissociation to form one or more product ions. One such product ion is isolated in the third quadrupole and is detected by the ion detector (tandem mass spectrometry). Each fragmentation reaction, one for each product and internal standard, is monitored separately in a duty cycle fashion such that the full set of products and internal standards are quantified. To obtain the moles of product, the mass spectrometry signal (ion counts) for the product is divided by that for the internal standard, and this ratio is multiplied by the moles of internal standard added to the assay.

Assay option 2. A variation of the above assay makes use of a modified pre-mass spectrometry sample workup. After the incubation to allow products to be generated enzymatically from substrates, a small aliquot of a suitable anion exchange resin is added to the mixture. An example resin is DE52 from Whatmann. It is well known that anions bind by electrostatic interaction with cations on the anion exchange resin, in this case all anionic analytes will bind to the resin. The substrates MPS-I-S, MPS-II-S, MPS-IIIA-S, MPS-IVA-S, MPS-VI-S, and MPS-VII-S contain either a carboxylate (MPS-I-S and MPS-VII-S) or a sulfate ester and will thus bind to the resin. The MPS-I-P, MPS-I-IS, MPS-IVA-P, MPS-IVA-IS, MPS-VI-P, MPS-VI-IS, MPS-VII-P, and MPS-VII-IS lack charge or contain a positive charge (MPS-IIIA-P and MPS-IIIA-IS) and will thus not be bound to the resin. The MPS-IIIB-S, MPS-IIIB-P and MPS-IIIB-IS also lack negative charge and will not bind to the resin. The MPS-II-S, MPS-II-P and MPS-II-IS are all anionic and thus will all bind to the resin. In this assay option, the assay buffer contains recombinant alpha-L-iduronidase, which acts on MPS-II-P and MPS-II-IS, not on MPS-II-S, to remove the iduronic acid residue from the aglcyone thus leaving behind the free aglycone, which lacks charge. Thus the resulting analytes derived from MPS-II-P and MPS-II-IS will not bind to the anion exchange resin. If recombinant alpha-L-iduronidase is included, the assay cannot include MPS-I-S because the enzyme will act on MPS-I-S to make MPS-I-P. The use of alpha-L-iduronidase is not limited to those MPS-II assays where anion exchange resin is added. The addition of this enzyme can also be done for all other MPS-II assays where anion exchanger is not used.

After addition of anion exchange resin, the mixture is extracted with ethyl acetate as in Assay Option 1, and all analytes not bound to the resin will extract into ethyl acetate. The ethyl acetate layer is then processed as described in Assay Option 1 for analysis by tandem mass spectrometry.

Multiplex Assays. The methods of the present invention provide for analysis of one or more of MPS-I, MPS-II, MPS-IIIA, MPS-IIIB, MPS-IVA, MPS-VI, and MPS-VII, including any combination thereof. For embodiments that utilize mass spectrometry to quantitate assay products, in certain embodiments, the product for each assay is mass distinct. The mass of each product differs such that a single assay can be utilized to quantitate all assay products. The mass distinctiveness is achieved by choice of substrates.

The representative substrates of MPS-I, MPS-II, MPS-IIIA, MPS-IIIB, MPS-IVA, MPS-VI, and MPS-VII described above provide mass distinct products (i.e., no two products have the same mass). Together with their corresponding internal standards (see representative internal standards of MPS-I, MPS-II, MPS-IIIA, MPS-IIIB, MPS-IVA, MPS-VI, and MPS-VII described above), the result is the ability to perform and analyze more than a single assay at a time.

In other embodiments, more than one product ion may have the same mass. In these embodiments, quantitation can be obtained so long as the fragment masses derived from these isobaric products are different (i.e., the combination of parent ion mass/fragment ion mass are unique for each species to be quantified in the mixture).

In one aspect, the invention provides a method for simultaneously assaying MPS-I, MPS-II, MPS-IIIA, MPS-IIIB, MPS-IVA, MPS-VI, and MPS-VII, or any subset thereof, using the reagents described herein.

Sulfatase Assays: MPS II, IIIA, IVA, and VI Screening

In another aspect, the invention provides assays, reagents, and kits for detection of sulfatases (MPS II, IIIA, IVA, and VI) associated with lysosomal storage diseases for newborn screening.

Assays of lysosomal enzymes using tandem mass spectrometry are useful for newborn screening of lysosomal storage diseases. The assays utilize substrates of the general structure: sulfate-sugar-aglycone. These substrates are acted on by the lysosomal sulfatase to yield the product lacking sulfate: sugar-aglycone. In certain assays, the sugar-aglycone product was detected using tandem mass spectrometry.

The present invention provides an alternative to those sulfatase assays. In certain aspects of the assays of the present invention, a second enzyme is added to the assay cocktail so as to effect remove of the sugar to provide the aglycone. Tandem mass spectrometry detection of the aglycone is more sensitive than detection of the sugar-aglycone. The second enzyme that removes the sugar does not act on the sulfated sugar (i.e., the second enzyme does not act on the substrate for the sulfatase). Thus, the present invention provides a method that includes an additional step of adding a suitable glycohydrolase or suitable lysase to the assay cocktail to produce the aglycone as the final enzyme product, which is then detected by tandem mass spectrometry.

As used herein, the term "glycohydrolase" refers to an enzyme that hydrolyzes glycosides. The term "lysase" refers to an enzyme that removes a proton from the sugar C2 and eliminates the glycosidic oxygen (e.g., aglycone leaving group) to provide an unsaturated sugar derivative.

Suitable second enzymes (e.g., glycohydrolases and lysases) are characterized in that they do cleave the sugar from the aglycone for the enzyme products described herein (e.g., they only cleave the sugar once the sulfate is removed), they do not act on the enzyme substrates themselves, and they are not inhibited by an inhibitor that is added in the assays of the invention to block the action of endogenous enzymes present in the dried blood spot like hexosaminidase A, which can cleave the sulfated substrate to provide the aglycone.

Suitable second enzymes include glycohydrolases and lysases.

Representative glycohydrolases include human hexosaminidase A, bacterial N-acetylhexosaminidases, bacterial β-N-acetylgalactosaminidase (e.g., *Paenibacillus* sp. TS12), alpha-L-iduronidase, β-galactosidase (*aspergillus*), and α-glucosidase (yeast).

Representative lysases include heparin lysase (heparinase) and heparanase.

Assay Methods. In one aspect, the invention provides methods for screening for MPS II, IIIA, IVA, and VI. The methods assay specific enzymes, the deficiencies of which lead to the lysosomal storage disease conditions. The methods advantageously assay one or more of iduronate-2- sulfatase (MPS-II), heparan N-sulfatase (MPS-IIIA), N-acetylgalactosamine-6-sulfate-sulfatase (MPS-IVA), and N-acetylgalactosamine-4-sulfate-sulfatase (MPS-VI).

As noted above, in the methods of the invention, a second enzyme is utilized to improve the sensitivity of the mass spectrometric assay embodiments and to generate the fluorophore in the fluorescent assay embodiments. In accordance with the methods, a suitable sulfatase substrate (i.e., sulfate-sugar-aglycone) is contacted with a sample to be assessed for sulfatase activity. When the sample includes a sulfatase, the substrate is enzymatically converted to an initial enzyme product (i.e., sugar-aglycone). In the methods of the invention, a second enzyme (e.g., a glycohydrolase) acts on the initial enzyme product to provide a secondary enzyme product (i.e., aglycone). Analysis of the secondary enzyme product (i.e., the aglycone) by tandem mass spectrometry provides increased sensitivity compared to previous assays in which the second enzyme is not present and which rely on the analysis of the initially formed enzyme product, the sugaraglycone. For substrates containing a type A aglycone, the second enzyme acts to release the fluorescent aglycone only after the sulfate is removed. This allows the sulfatase to be assayed by fluorescence analysis.

For fluorescent assays the quench can include a buffer to raise the pH to about 10 so that the phenolic hydroxy of the aglycone is deprotonated thus rendering the product (aglycone) highly fluorescent.

In the assays, one or more substrates (S) are incubated in a suitable buffer with a suitable source of enzymes such as a dried blood spot from a newborn screening card or a urine sample for a sufficient time to form one or more products (P1) that are subsequently subjected to a second enzyme (i.e., a glycohydrolase) to provide secondary enzyme products (P2) that are detected by tandem mass spectrometry. The assay also makes used of an internal standard (IS), which in certain embodiments are chemically identical to the enzyme-formed product, but has a different mass (e.g., heavy isotope substituted such as deuterium and/or carbon-13 substitutions). In certain assays, the internal standard is also acted on by the second enzyme to form the final internal standard that is detected by tandem mass spectrometry. The incubation is done in a suitable buffer to allow the enzymatic reactions to proceed. A suitable buffer is for example 100 mM ammonium formate pH 4.5 containing 7.5 mM barium acetate and 5 mM cerium acetate.

Enzymes that are advantageously assayed with the reagents of the invention include the following:

(a) iduronate-2-sulfatase, which acts on the substrate of MPS-II to produce the MPS-II product, and the assay makes use of the MPS-II internal standard;

(b) heparan N-sulfatase, which acts on the substrate of MPS-IIIA to produce the MPS-IIIA product, and the assay makes use of the MPS-IIIA internal standard;

(c) N-acetylgalactosamine-6-sulfate-sulfatase, which acts on the substrate of MPS-IVA to produce the MPS-WA product, and the assay makes use of the MPS-IVA internal standard; and (d) N-acetylgalactosamine-4-sulfate-sulfatase, which acts on the substrate of MPS-VI to produce the MPS-VI product, and the assay makes use of the MPS-VI internal standard.

In certain embodiments, additional assay options are also included within the methods of the invention Assay options 1 and 2 noted above can be utilized in these assay methods.

Reagents. Reagents for screening MPS II, IIIA, IVA, and VI include substrates (S), products (P), and internals standards (IS) for screening for MPS II, IIIA, IVA, and VI.

The reagents can be advantageously utilized to assay enzymes. The reagents include enzyme substrates (S), enzyme products (P), and assay internal standards (IS). In certain embodiments, one or more substrates (S) and their corresponding internal standards (IS) are incubated in a suitable buffer with a suitable source of enzymes such as a dried blood spot from a newborn screening card or a urine sample for a sufficient time to form one or more products (P) that are subsequently subject to a second enzyme (e.g., a glycohydrolase) to provide a second enzyme product that is detected by tandem mass spectrometry. In certain embodiments, the internal standard (IS) is chemically identical to the enzyme-formed product except the standard has a different mass (e.g., heavy isotope substituted such as deuterium and/or carbon-13 substitutions).

Reagents useful in the assay of these sulfatases include substrates (S), products (P), and internals standards (IS) for MPS-II, MPS-IIIA, MPS IVA, and MPS-VI, including those described herein.

Representative assays for MPS-II, MPS-IIIA, MPS IVA, and MPS-VI are described in Examples 7-11.

Representative Assays and Results for MPS IVA and VI Screening

As described above, glycohydrolase and lysase enzymes are used to improve the sensitivity of assaying sulfatases using mass spectrometry and to provide fluorescent aglycone products for fluorescent assays. In a related aspect, a method is provided that further includes the step of adding an inhibitor to block endogenous glycohydrolase activity.

Suitable inhibitors block endogenous glycohydrolase activity, but do not significantly inhibit the activity of the added glycohydrolase. Dried blood spots contain, for example, hexosaminidase A, which can act on the sulfated substrate to form the aglycone in one step. In this case it is optimal to add an inhibitor of the hexosaminidase when the aglycone is measured by tandem mass spectrometry or fluorimetry in order to quantify the sulfatase enzyme. The added inhibitor should not significantly inhibit the second enzyme, which is added to the assay to convert the initial sulfatase product to the aglycone.

Suitable inhibitors block the hexosaminidase(s) in the biological sample, but do not fully block the second enzyme. The inhibitor may partially block the latter, but not so completely that the latter can convert most if not all of the initial sulfatase product to its aglycone. Suitable inhibitors inhibit human hexosaminidinase A, human hexosaminidinase B, and/or human hexosaminidinase X.

Representative inhibitors include (Z)—O-(2-acetamido-2-deoxy-D-glucopyranosylidene)-amino N-phenylcarbamate (Z-PUG-NAc), 1-deoxynojirmycin, castanospermine, swainsonine, calystegine $B_2$, isofagamine, Tamiflu, gluconohydroximolactone, glucuronic acid and its lactones and lactams, Relenza, miglitol, phenethyl substituted gluco-and galacto-imidazoles, N-hydroxyethyl dehydronojirimycin, GalNAc thiazoline, and GlcNAc thiazoline.

Representative assays for MPS-WA and MPS-VI are described below.

Representative Assay for Mucopolysaccharidosis IVA. In one embodiment, an assay is provided for MPS-IVA, also known as Morquio A syndrome, to detect N-acetylgalactosamine-6-sulfatase (also known as GALNS and used herein interchangeable with this term), the enzyme that is deficient in MPS-IVA. The GALNS substrate was N-acetylgalactose-6-sulfate attached to the aglycone where $R_1$ is n-butyl, $L_2$ is —$CH_2CH_2$—, $L_3$ is —$(CH_2)_5$—, and $R_3$ is phenyl (see below). The assay includes adding an enzyme that removes N-acetylgalactosamine from aglycone, only after the 6-sulfate has been removed. An enzyme for removing N-acetylgalactosamine from aglycone is beta-hexosaminidase (e.g., human hexosaminidase A), which cleaves beta-glycosides to N-acetylgalactosamine and N-acetylglucosamine residues. The biological sample may contain human hexosaminidase A and other human hexosaminidases. Human hexosaminidase A can act on the MPS-IVA substrate to generate the aglycone. As shown in Table 1, human hexosaminidase A can cleave the glycoside even when the sugar is sulfated at the 6-position. See rows in which Z-PUG-NAc is omitted.

Table 1 also shows that the amount of hexosaminidase A endogenous in dried blood spots causes problems in the assay of GALNS using dried blood spots for newborn screening of Morquio A syndrome.

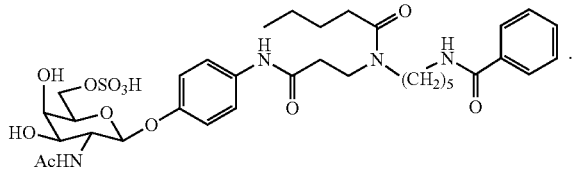

Representative assays use dried blood spots on newborn screening cards as a source of GALNS. These assays also use beta-NGA as well as the inhibitor of human hexosaminidase A: Z-PUG-NAc ((Z)—O-(2-acetamido-2-deoxy-D-glucopyranosylidene)-amino N-phenylcarbamate).

The GALNS enzyme in the dried blood spots acts on the GALNS substrate shown above to liberate the product (i.e., the GALNS substrate without the 6-sulfate). The bacterial beta-NGA in the assay cocktail acts on the GALNS substrate without the 6-sulfate to liberate the aglycone, and does not

TABLE 1

Assay results for GALNS.

| Expt. number | Sample | Additives to substrate in assay buffer | GALNS product (substrate without sulfate) peak area | aglycone peak area (product without sugar) | GALNS internal standard peak area | internal standard aglycone peak area |
|---|---|---|---|---|---|---|
| 1 | 3 mm dried blood spot punch | 1 mM Z-PUG-NAc, 0.01 mg beta-NGA | 46,100 | 411,000 | 278 | 54,400 |
| 2 | 3 mm filter paper punch (no blood) | 1 mM Z-PUG-NAc, 0.01 mg of bacterial enzyme | 422 | 42,000 | 3,290 | 15,900 |
| 3 | 3 mm dried blood spot punch | 1 mM Z-PUG-NAc, no beta-NGA | 121,000 | 42,900 | 23,500 | 940 |
| 4 | 3 mm filter paper punch (no blood) | 1 mM Z-PUG-NAc, no beta-NGA | 753 | 22,700 | 14,700 | 412 |
| 5 | 3 mm dried blood spot punch | 0.01 mg beta-NGA, no Z-PUG-NAc | 25,100 | 1,350,000 | 852 | 49,200 |
| 6 | 3 mm dried blood spot punch | Nothing | 110,000 | 1,110,000 | 17,900 | 17,100 |
| 7 | 3 mm filter paper punch (no blood) | 0.01 mg beta-NGA, no Z-PUG-NAc | 253 | 19,800 | 1,920 | 22,200 |
| 8 | 3 mm filter paper punch (no blood) | Nothing | 820 | 14,500 | 12,100 | 648 |

In certain embodiments, the bacterial enzyme, beta-N-acetylgalactosaminidase (beta-NGA) from Paenibacillus sp. TS12 (J. Biol. Chem. 2011, 286, 14065-14072), is used in the assays. This enzyme is not structurally related to human hexosaminidases, and data shown in Table 1 shows that the bacterial enzyme cleaves beta glycosides to N-acetyl-galactosamine when it is not sulfated on the 6-position, and that the enzyme does not significantly act on the substrate when it bears the sulfate.

In certain embodiments, the inhibitor of human hexosaminidase A is used in the assays to block human hexosamidinase A action on the GALNS substrate. In certain embodiments, the inhibitor does not significantly inhibit beta-NGA.

The GALNS substrate used in the above assay has the following structure:

act on the GALNS substrate. The addition of Z-PUG-NAc to the assay cocktail blocks the ability of endogenous human hexosaminidase A to act on GALNS substrate to generate the aglycone. The algycone is then detected by tandem mass spectrometry. Thus, aglycone formation marks the action of GALNS, and sensitivity is gained by detecting the aglycone rather than the initially formed desulfated product.

Representative sulfatase assays for MPS-IVA are described in Example 10.

Representative Assay for MPS-VI. In another embodiment, the invention provides an assay that was developed for MPS-VI, to detect arylsulfatase B (ASB), the enzyme that is deficient in MPS-VI, also known as Maroteaux-Lamy syndrome.

The following ASB (MPS-VI) substrate was used in the assay:

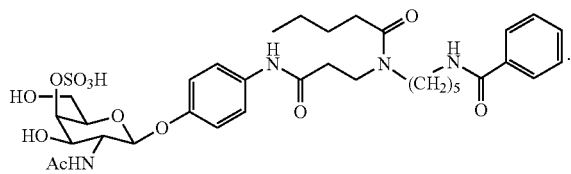

ASB removes the 4-sulfate from the N-acetyl-galactosamine-4-sulfate group from the ASB substrate. Prior to the present invention, no data was available on the ability of human hexosaminidase A to act on N-acetyl-galactosamine-4-sulfates. Recombinant human hexosaminidase A acts on the ASB substrate to liberate aglycone. Aglycone was detected by UHPLC-MS/MS (see FIG. 1).

FIG. 1 shows that the amount of this aglycone increases as the amount of hexosaminidase A is added to the mixture. The mixture includes 1 mM ASB substrate in 100 mM ammonium formate buffer, pH 5.6 containing the indicated amount of hexosaminidase. After incubation for 5 hrs at 37° C., the mixture is analyzed by UHPLC-MS/MS. The aglycone signal is not due to contamination of the substrate with aglycone because no aglycone is seen when hexosaminidase A is omitted. The aglycone is not the result of cleavage of the ASB in the electrospray ionization source of the mass spectrometer because the amount of aglycone increases with increasing hexosaminidase A (FIG. 1), and the UHPLC retention time of the aglycone matches that of an authentic aglycone, and this is different than the retention time of the ASB substrate. Thus, hexosaminidase A acts on the ASB substrate to produce algycone. Because hexosaminidase A acts on ASB substrate to produce algycone, this enzyme cannot be used in a coupled assay of ASB, and furthermore it is important to inhibit hexosaminidase A so as not to generate aglycone directly from the ASB substrate.

Having established the action of human hexosaminidase A on the ASB substrate, the ASB assay was developed, using the same approach developed for GALNS, namely adding beta-NGA and Z-PUG-NAc. Results are given in Table 2 below. The experiments were carried out as for the GALNS assays (see Example 10) but with 1 mM ASB substrate replacing the GALNS substrate.

Comparison of Experiment 1 (complete assay with blood) to Experiment 2 (no blood control) shows that beta-NGA present converts most of the ASB internal standard to its aglycone in both experiments. The amount of aglycone, 1,570,000 with blood, is well above that formed in the no-blood control, 58,300. Experiment 3 has blood and Z-PUG-Nac, but no beta-NGA, and the amount of ASB product, 371,000 is compared to the signal of 1,570,000 for its aglycone in the presence of beta-NGA, again showing the sensitivity advantage of converting the product to the aglycone. Finally, Experiment 4 has no blood and no beta-NGA or Z-PUG-NAc, showing that the ASB substrate is contaminated with small amounts of the product, 3,340 and its aglycone, 33,800.

The present invention provides for the use of any enzyme that has the properties described herein below for execution of assays of GALNS and ASB enzymatic activities:

(a) the enzyme used in the assays described herein should cleave the sugar to yield the aglycone only if the sugar does not bear a sulfate at the 4-or 6-positions; and (b) the enzyme used in the assays described herein should not be significantly inhibited by an inhibitor added to the assay mixture that significantly inhibits human hexosaminidase A present in the biological sample (e.g., dried blood spot) that is the source of lysosomal enzyme to be assayed.

Fluorescence Detection. In some embodiments, certain assays of the invention are also useful in the assay of the enzymes described herein using fluorescence methods. In one aspect, aglycone is fluorescent but is less fluorescent when it forms a glycosidic linkage to the sugar. Thus in one aspect, the combined action of arylsulfatase B (ASB) and bacterial N-acetylgalactosaminidase leads to an increase in fluorescence signal due to the formation of the highly fluorescent aglycone. A fluorogenic glycoside suitable for use with the assays of the present invention is shown below.

TABLE 2

Assay results for ASB.

| Expt. Number | Sample | Additives to substrate in assay buffer | ASB product (substrate without sulfate) peak area | aglycone peak area (product without sugar) | ASB internal standard peak area | internal standard aglycone peak area |
|---|---|---|---|---|---|---|
| 1 | 3 mm dried blood spot punch | 1 mM Z-PUG-NAc, 0.01 mg beta-NGA | 154,000 | 1,570,000 | 39 | 50,800 |
| 2 | 3 mm filter paper punch (no blood) | 1 mM Z-PUG-NAc, 0.01 mg of bacterial enzyme | 404 | 58,300 | 210 | 25,600 |
| 3 | 3 mm dried blood spot punch | 1 mM Z-PUG-NAc, no beta-NGA | 371,000 | 39,900 | 20,900 | 1,320 |
| 4 | 3 mm filter paper punch (no blood) | nothing | 3,430 | 33,800 | 17,700 | 840 |

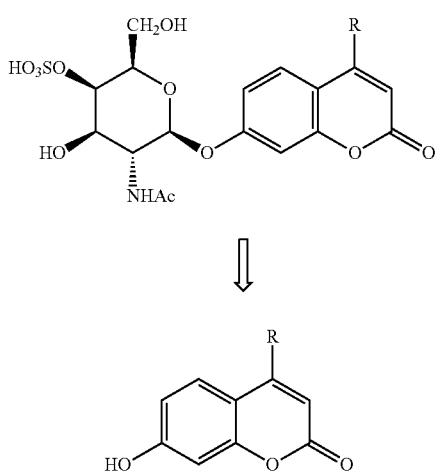

⇓

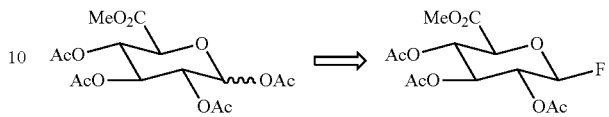

The fluorogenic glycoside shown above is a fluorogenic ASB substrate containing a glycoside to 7-hydroxycoumarin bearing an additional substituent (R group). The consecutive action of ASB followed by bacterial N-acetylgalactosaminidase leads to the substituted 7-hydroxycoumarin, which is more fluorescent than the glycoside. Thus, the ASB is assayed by observation of an increase in fluorescence signal. Other fluorophores can also be used, so long as the glycoside is a substrate for ASB and N-acetylgalactosaminidase and the fluorophore changes its fluorescence intensity when the glycoside is cleaved. It will be appreciated that fluorescence intensity is significantly increased at high pH when the phenol becomes phenoxide as a result of deprotonation. Experimentally, in certain embodiments, the assay is quenched with a pH 10.5 buffer to reveal fluorescence.

Previously, there had been no use of this method to assay ASB or use of an enzyme to selectively cleave the glycoside only when it is not sulfated. This method can also be used to assay GALNS with the suitable substrate containing a sulfate on the 6-position of the sugar residue. The invention provides an assay that uses a substrate based on N-acetylgalactosamine-6-sulfate, which is acted on by GALNS more rapidly than other substrates, such as 4-methylumbelliferone attached as a glycoside to galactose-6-sulfate.

The following examples are provided for the purpose of illustrating, not limiting, the invention.

EXAMPLES

Example 1

Synthesis of Representative MPS-I and MPS-II Reagents

In this example, the synthesis of representative MPS-I (MPS-I-S-Acetyl-C6 and MPS-I-IS-Acetyl-C6) reagents and MPS-II (MPS-II-S-Pentanoyl-C6 and MPS-II-IS-Pentanoyl-C6) reagents is described.

Synthesis of 1-F-2,3,4-Triacetoxy-Iduronic Acid Methyl Ester

The synthesis of 1-F-2,3,4-triacetoxy-iduronic acid methyl ester is described below.

Step 1

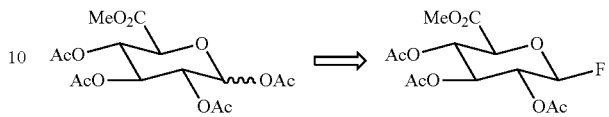

A 50.05 g (133.0 mmol) portion of methyl 1,2,3,4-tetra-O-acetyl-alpha,beta-glucopyranosyluronate (Carbosynth, UK) was suspended at 0° C. in 295 mL 33% HBr/acetic acid (Acros Cat. 123180010) under nitrogen and stirred for 15 minutes at 0° C. The reaction was allowed to warm to room temperature and stirring continued for 3 hours. The reaction was diluted with 295 mL of toluene and then concentrated on a rotary evaporator (30-35° C. water bath with water aspirator suction). The residue was dissolved in 800 mL EtOAc, washed with 500 mL of ice-cold saturated aqueous NaHCO$_3$, washed with ice-cold brine and then dried over anhydrous Na$_2$SO$_4$. The solution was filtered, and the solvent was removed by rotary evaporation as above. The compound was placed under high vacuum for 1 hour at room temperature. Proton-NMR (CDCl$_3$) is consistent with the product. TLC on silica with 20% EtOAc/hexane (charring with 5% H$_2$SO$_4$ in MeOH) shows the product at R$_f$ about 0.6 with the starting material at R$_f$ about 0.5. Two small spots were seen just above the origin.

The crude bromide from above was dissolved in 600 mL of anhydrous acetonitrile and stirred under nitrogen for about 5 minutes to dissolve the bromide. The flask was wrapped in aluminum foil to exclude light. 20.27 g of AgF (Oakwood Cat. 002862) was added in one portion. The reaction was stirred in the dark under nitrogen at room temperature for 24 hours. TLC on silica with 20% EtOAc/hexane (charring with 5% H$_2$SO$_4$ in MeOH) shows the product at R$_f$ about 0.5 with the starting material at R$_f$ about 0.6. The mixture was filtered through a pad of Celite with suction, and the filtrate was then concentrated by rotary evaporation (30-35° C. water bath with water aspirator for suction). 180 g silica was loaded into a glass column and hexanes were passed through the column. The compound was dissolved in EtOAc and a minimal amount of dry silica was added. The EtOAc was removed by rotary evaporation, and the resulting compound/silica mixture was loaded onto the top of the column. The column was run with low air pressure. Initially 1 L of 100% hexanes was passed through the column and no product eluted. The column was then run with 2 L of 20% EtOAc/hexanes and no product eluted. 1 L of 25% EtOAc/hexanes also did not elute the product. The column was finally run with 3 L of 30% EtOAc/hexanes and all of the product eluted. The fractions were pooled, and the solvent was removed by rotary evaporation to give a white, crystalline solid. The product was dried under high vacuum for 1 hour at room temperature to give 27.0 g of product (60.4% yield). Proton-NMR in CDCl$_3$ was consistent with the product.

Step 2

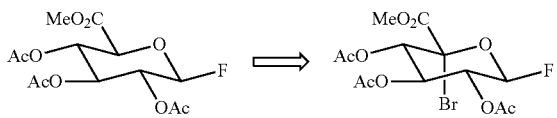 [SMILES: COC(=O)C1OC(F)C(OC(C)=O)C(OC(C)=O)C1OC(C)=O ; COC(=O)C1(Br)OC(F)C(OC(C)=O)C(OC(C)=O)C1OC(C)=O]

6.0 g of the fluoride from above and 6.0 g of NBS (Aldrich Cat. B81255-500G, recrystallized from hot water, dried overnight under high vacuum) was dissolved in 240 mL $CCl_4$ (JT Baker Cat. 1512-3) and stirred under nitrogen in a round-bottom flask positioned next to a UV lamp (450 W, Ace Glass 7825-34 lamp in a quartz jacket with water circulation to cool the lamp). Another round-bottom flask with an identical reaction was placed on the opposite side of the same UV lamp. Two reactions were run simultaneously in this fashion.

The outside of hood was covered with aluminum foil to protect the chemist. The lamp was turned on and the reaction refluxed at 78° C. for 2 hours. The lamp was turned off, about 6 g portion of NBS was added to each of the reactions, the UV lamp was turned back on and reactions were allowed to continue refluxing. After another 2 hours, additional about 6 g portions of NBS were added as above and refluxing continued in the presence of the UV lamp for 3 more hours. After a total of 7 hours, the lamp was turned off and reactions were allowed to cool to room temperature. Each reaction was filtered through glass wool and the wool was washed with 50 mL of $CCl_4$. The solvent was removed by rotary evaporation (35° C. water bath with water aspirator for suction). TLC with 30% EtOAc/hexanes showed the product spot at $R_f$ about 0.6 running just above starting material (charring with 5% $H_2SO_4$ in MeOH). 4×6 g scale reactions were purified simultaneously on a column with 180 g silica. The compound was dissolved in EtOAc, a minimum amount of dry silica was added, the EtOAc was removed by rotary evaporation and the silica/compound mixture was then loaded to the top of the column. The column was run with 1 L of 100% hexanes and no product eluted. The column was run with 2 L of 10% EtOAc/hexanes and no product eluted. The column was run with 3 L of 20% EtOAc/hexanes and the product eluted as the slower of two spots visualized by TLC. The fractions (from 700 mL to 1300 mL of added 3 L) that contained the minor product (the faster TLC spot) were discarded. All product containing fractions (from 1400 mL to 2500 mL of added 3 L) were combined, and the solvent was removed by rotary evaporation, giving a viscous yellow liquid that became a crystalline solid upon standing overnight. This solid was placed under high vacuum for 12 hours. 18.90 g of total product was obtained from 4×6 g reactions (63.3% yield).

Step 3

9.92 g of the bromide from above was dissolved in 154 mL of toluene (not dry; Macron Chemicals cat# 4483-4L) and stirred under nitrogen. 10.0 mL of $Bu_3SnH$ (either Aldrich 234188-1OG or Acros 215730500) was added and the mixture was refluxed at 110° C. for 1 hour. TLC (10% EtOAc in toluene) showed some starting material left, so refluxing was continued for an additional hour. TLC was repeated and indicated that the reaction was complete. The round bottom flask was allowed to cool to room temperature, and the solvent was removed by rotary evaporation (about 40° C. water bath with water aspirator for suction).

180 g silica was loaded into a column. The crude residue was absorbed onto silica and loaded onto the column as before. The column was run with 1 L of 100% toluene and no product eluted. The column was run with 1 L of 10% EtOAc/toluene and no product eluted. The column was run with 2.5 L of 20% EtOAc/toluene and the product eluted as the slower of two spots at $R_f$ about 0.6 (TLC in 10% EtOAc/toluene). The faster spot at $R_f$ about 0.7 was the glucuronic acid, minor product. The fractions (from 600 mL to 1000 mL of the 2.5 L) that contained the faster TLC spot were discarded. The fractions containing the product (from 1100 mL to 2100 mL of the 2.5 L) were pooled and concentrated by rotary evaporation (about 40° C. water bath with water aspirator for suction) and placed under high vacuum for 3 hours to give 5.2 g of the product (64.7% yield). The product is a clear, viscous liquid upon purification.

Aglycone Preparation

The aglycones can be made by two methods. The first method utilizes Michael addition of commercial mono-BOC-1,6-hexanediamine to HO-Ph-NHCO—CH=$CH_2$ followed by acetylation of the secondary amine, removal of the BOC, and benzoylation of the primary amine. Some benzoylation of the phenol-OH occurs, but this ester is cleaved by saponification prior to sample workup. The second method includes treating mono-BOC-1,6-hexanediamine with benzoyl chloride, removal of BOC to give the mono-benzoyl-1,6-hexanediamine, which is used in the Michael addition followed by acetylation of the secondary amine. Because benzoylation and BOC removal are both nearly quantitative, each route is essentially equivalent.

Mono-benzoylation of symmetric diamines (Tang, W.; Fang, S. Tetrahedron Lett. 2008, 49, 6003)

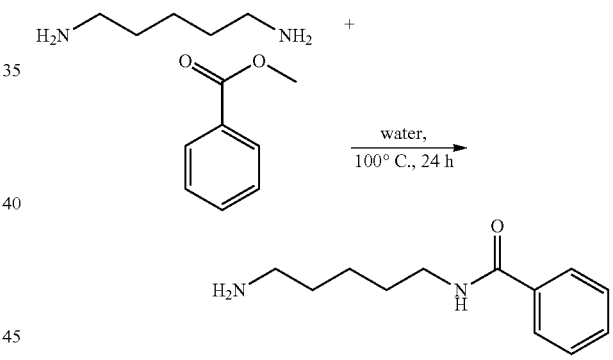

To methyl benzoate (1.0 g, 7.34 mmol), pentane-1,5-diamine (0.75 g, 7.34 mmol), and water (0.37 mL) were added and the mixture was heated to 100° C. for 24 hours under constant stirring. The reaction mixture was cooled to room temperature and directly loaded on to a short silica column (the silica column was pre-flushed with 4% triethylamine in chloroform followed by 100% chloroform before loading the reaction mixture). Upon elution with 30% of methanol in chloroform the desired mono-benzoylated product was obtained (0.80 g, 53%) as pale yellow oil. $^1$H NMR (300 MHz, MeOD) δ 7.83 (d, J=7.4 Hz, 2H), 7.58-7.31 (m, 4H), 3.41 (t, J=7.0 Hz, 2H), 2.76 (t, J=7.2 Hz, 2H), 1.74-1.21 (m, 6H). MS (EST$^+$) for [M +H]$^+$; calculated: 207.1, found: 207.2.

Method 1. A solution of 4-aminophenol (50 g, 458 mmole) in $CH_2Cl_2$ (400 mL) and saturated $NaHCO_3$ in water (400 mL) was stirred for 10 min at room temperature, then acryloyl chloride (40.9 mL, 503.8 mmole) was added dropwise and the reaction stirred for an additional 6 hr at room temperature. The resulting solid was collected by filtration, washed with water and dried under vacuum (oil pump) to afford 75 g of 4-acrylamido-phenol.

4-Acrylamido-phenol (163 mg, 1 mmol) and mono-BOC-1,6-hexanediamine (Ark Pharm Inc.) (237 mg, 1.1 mmol) were dissolved in a solution of isopropanol (9 mL) and water (1 mL) and heated in an oil bath at 65° C. for 48 hrs. The reaction mixture was concentrated by rotary evaporation to afford the Michael addition product, which was used in the next step without further purification.

To the residue from the above step was added $CH_2Cl_2$ (4 mL) and 4 mL of saturated sodium bicarbonate in water. Acetyl chloride (0.21 mL, 3 mmole) was added dropwise at room temperature with stirring, and the mixture was stirred for an additional 3 h at room temperature. The layers were allowed to separate, and the $CH_2Cl_2$ layer was concentrated by rotary evaporation.

The residue was dissolved in 4 mL of $CH_2Cl_2$ and 2 mL of 4 M HCl in dioxane was added dropwise with stirring. Stirring was continued at room temperature for 1 hr. The resulting solid was collected by filtration, and the solid was dried under vacuum (oil pump).

To the above solid was added 10 mL of $CH_2Cl_2$ and 10 mL of saturated sodium bicarbonate in water. Benzoyl chloride (0.23 mL, 2 mmole) was added dropwise with stirring, and the mixture was stirred an additional 3 hr at room temperature. The layers were allowed to separate, and the $CH_2Cl_2$ layer was concentrated with a rotary evaporator. The residue was dissolved in 2 mL of MeOH, and 2 mL of 5% NaOH in water was added. The mixture was stirred for 30 min at room temperature (this step is necessary to remove any benzoylated phenol). The mixture was neutralized with 1 M HCl and extracted with EtOAc. The organic layer was dried over $Na_2SO_4$, filtered and solvent was removed by rotary evaporation. The residue was submitted to silica gel chromatography with 5% MeOH in $CH_2Cl_2$ to give 170 mg of pure product (40% overall yield).

Method 2. To an ice-cooled solution of mono-BOC-1,6-hexanediamine.HCl (20 g, 79.12 mmol) in dry dichloromethane (350 mL) was added anhydrous triethylamine (33 mL, 237.4 mmol) dropwise with stirring under nitrogen atmosphere. After 10 min, benzoyl chloride (9.64 mL, 83 mmol) was added dropwise at 0° C., and the resulting mixture was stirred overnight at room temperature. Water (200 mL) was added, and the aqueous layer was extracted twice with 200 mL portions of $CH_2Cl_2$ and the organic extracts were combined and washed with water, brine and dried over anhydrous $Na_2SO_4$, filtered and concentrated by rotary evaporation. The resulting solid was washed with hexane to remove the less polar impurities, and the solid was used for next step without purification.

The above solid was dissolved in 100 mL of $CH_2Cl_2$ and 300 mL of 20% TFA in $CH_2Cl_2$ was added dropwise at 0° C. with stirring, and the resulting mixture was stirred overnight at room temperature. The reaction mixture was concentrated by rotary evaporation. The resulting residue was dissolved in 300 mL water and washed twice with 200 mL portions of $CH_2Cl_2$ to remove less polar impurities. The resulting water layer was neutralized with 5% NaOH in water and extracted with four times with 200 mL portions of $CH_2Cl_2$. The organic layers were combined and dried over $Na_2SO_4$, filtered and solvent removed by rotary evaporation. The resulting crude product (14.6 g, 66.4 mmol, 84%) was used in the next step without further purification. In this way the free amine is obtained, which is needed for the next step (Michael addition).

4-Acrylamido-phenol (8.43 g, 51.6 mmol) and mono-benzoyl-1,6-hexanediamine (12.5 g, 56.8 mmol) were dissolved in a solution of isopropanol (450 mL) and water (50 mL) and heated in an oil bath at 65° C. for 48 hrs. The reaction mixture was concentrated by rotary evaporation to afford the Michael addition product, which was divided into 2 parts and used for the next step without further purification.

Acetylation. To the residue from the above step was added $CH_2Cl_2$ (100 mL), DMF (10 mL) and 100 mL of saturated sodium bicarbonate in water. Acetyl chloride (3.7 mL, 52 mmol) was added dropwise at room temperature with stirring, and the mixture was stirred for an additional 6 h at room temperature. The organic layer was separated, and the water layer was extracted twice with 50 mL portions of 5% MeOH in $CH_2Cl_2$. The organic layers were combined and concentrated by rotary evaporation. The residue was purified by silica gel column chromatography (1-5% MeOH in $CH_2Cl_2$) to afford MPS-I aglycone (4.5 g, 10.6 mmol) in 41% yield.

Pentanoylation. To the residue from the above step was added $CH_2Cl_2$ (100 mL), DMF (10 mL) and 100 mL of saturated sodium bicarbonate in water. Pentanoyl chloride (6.17 mL, 52 mmol) was added dropwise at room temperature with stirring, and the mixture was stirred for an additional 6 h at room temperature. The organic layer was separated, and the water layer was extracted twice with 50 mL portions of 5% MeOH in $CH_2Cl_2$. The organic layers were combined and concentrated by rotary evaporation. The residue was purified by silica gel column chromatography (1-5% MeOH in $CH_2Cl_2$) to afford the MPS—II aglycone (3.5 g, 7.5 mmol) in 29% yield.

MPS-I-IS-Acetyl-C6

The internal standard, MPS-I-P-Acetyl-C6, was prepared as described for the MPS-I aglycone except using $d_5$-benzoyl chloride (Aldrich). The enzymatic product, MPS-I-P-Acetyl-C6, is the MPS-I aglycone (i.e., identical to the IS, but with non-deuterated benzoyl).

Aglycone Coupling to Iduronyl-F, Deacetylation, and Methyl Ester Hydrolysis

The following describes the procedure for coupling with the MPS-II aglycone. The procedure for coupling with the MPS-I aglycone is analogous.

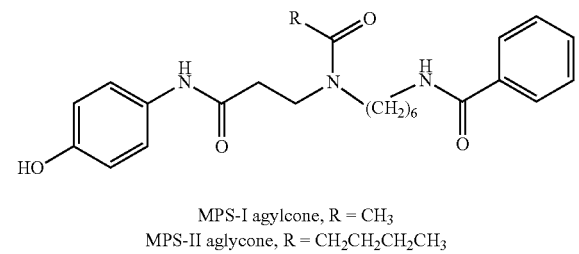

MPS-I agylcone, R = $CH_3$
MPS-II aglycone, R = $CH_2CH_2CH_2CH_3$

MPS-II aglycone (1.9 g, 4.06 mmol, 1 eq), methyl 2,3,4-trihydroxy-iduronosy-1-F (1.23 g, 3.66 mmol, 0.9 eq) and 2,6-di-tert-butyl-4-methylpyridine (2.5 g, 12.2 mmol, 3 eq) were dried for 1 hr under high vacuum (oil pump) and dissolved in dry $CH_2Cl_2$ (80 mL, 0.05 M). All of the MPS-II aglycone dissolved before addition of $BF_3$-etherate. For the reaction with MPS-I aglycone, more $CH_2Cl_2$ was used to give 0.02 M aglycone (not all dissolved even after $BF_3$-etherate was added).

BF$_3$•Et$_2$O (5.1 mL, 40.6 mmol, 10 eq) was added dropwise with stirring at room temperature under a nitrogen atmosphere. After the reaction mixture had been stirred for 2.5 h at room temperature, 150 mL of saturated aqueous NaHCO$_3$ was added. The aqueous layer was extracted with CH$_2$Cl$_2$ and the organic extracts were combined and washed with water, brine and dried over anhydrous Na$_2$SO$_4$. The solution was filtered and concentrated by rotary evaporation. The residue was purified by silica gel column chromatography (CH$_2$Cl$_2$, then 1-4% MeOH in CH$_2$Cl$_2$) to afford product (1.87 g, 2.38 mmol) in 65% yield.

Deacetylation. To a solution of coupled product (2.7 g, 3.44 mmol, 1 eq) in 75 mL of dry methanol (Aldrich) was added 0.5 M sodium methoxide in methanol (2.75 mL, 1.38 mmol, 0.4 eq) dropwise at 0° C. under a nitrogen atmosphere with stirring. The reaction mixture was stirred at 0° C. for 3 h. The reaction mixture was neutralized with AG 50W-X8 resin (H+) and filtered. The filtrate was concentrated by rotary evaporation. Column chromatography on silica gel (1-6% MeOH in CH$_2$Cl$_2$) afforded product (2.1 g, 3.19 mmol) in 92% yield.

Methyl Ester Hydrolysis. The MPS-I-S-Acetyl-C6 is made by demethylation of the methyl ester. For the MPS-II-S-Pentanoyl-C6, the deacetylated compound is sulfated, and then the methyl ester is hydrolyzed. The MPS-II-P-Pentanoyl-C6 is made by methyl ester saponification without sulfation, as for MPS-I-S-Acetyl-C6. The MPS-II-IS-Pentanoyl-C6 is made as for MPS-II-P-Pentanoyl-C6, but with the aglycone containing a d$_5$-benzoyl group.

Deacylated compound (1.5 g, 2.44 mmol, 1 eq) was dissolved in 150 mL of water/methanol (1:1) at room temperature. An aqueous solution of sodium hydroxide 0.1 M was added in increments of 0.1 eq of NaOH until the pH of the solution reached approximately 8 (pH paper). The pH was maintained by incremental additions of the 0.1 M NaOH solution as the reaction proceeded (about 2 eq NaOH added). The reaction mixture was stirred overnight. The reaction mixture was neutralized with 1 M HCl and concentrated by rotary evaporation. The residue was purified by column chromatography on silica (5% MeOH and 1% AcOH in CH$_2$Cl$_2$, then 10% MeOH and 2% AcOH in CH$_2$Cl$_2$) to give product MPS-I-S-Acetyl-C6 (1.45 g, 2.41 mmol) in 98% yield.

It is important to remove as much as possible of the MPS-I enzymatic product from the substrate otherwise the assay blank will be higher. The substrate can be dissolved in water at pH 7 and extracted with EtOAc because the product will extract well. However, the substrate, anionic because of its carboxylate, will remain in the water. Dissolve 1.5 g of MPS-I-S-Acetyl-C6 in 200 mL distilled water and adjust pH to close to 7 with KOH using a pH meter. Extract with 3 200 mL potions of EtOAc. Transfer the water layer to a round bottom flask and place on a rotary evaporator with water aspiration and a water bath at 30° C. and rotovap for about 20 min to remove any EtOAc in the water. Then lyophilize the water layer to give the final product, the sodium salt of MPS-I-S-Acetyl-C6. This procedure produced the substrate containing the MPS-I product. Alternative purifications were investigated.

In one alternative, 50 mg of MPS-I-S-Ac-C6 was dissolved in 5 mL water, adjusted to pH 7 (pH meter) with dilute aqueous NaOH, extracted with 8 mL ethyl acetate by vortexing and then centrifuged to separate the layers, repeat 4 more times (so total 40 mL ethyl acetate). The water layer was lyophilized. The amount of MPS-I product was very low and acceptable by this purification.

In another alternative, 120 mg of MPS-I-S-Ac-C6 was purified by flash Si column (10 g Silica) using a linear 1-10% MeOH in CH$_2$Cl$_2$ gradient over 10 min and then to 20% MeOH/2% water/CH$_2$Cl$_2$. The peak of material was pooled in 3 batches, first third, second third and last third of the peak. The solvent was removed by rotary evaporation with a 30° C. water bath and water aspiration. Assays done with the 3 separate batches showed that the middle and last third peak materials contained acceptable amounts of MPS-I-product.

Sulfation and methyl ester hydrolysis. Deacetylated compound (2 g, 3.04 mmol, 1 eq) was solubilized in anhydrous MeOH (120 mL) and dibutyltin (IV) oxide (1.13 g, 4.56 mmol, 1.5 eq) was added. The reaction mixture was heated under reflux for 1 hour under nitrogen, after which time the dibutyltin oxide was completely dissolved. The reaction mixture was allowed to cool and was concentrated under vacuum. The residue was co-evaporated once with anhydrous toluene (100 mL) to remove traces of water. The residue was solubilized in anhydrous N,N-dimethylformamide (120 mL). Sulfur trioxide—trimethylamine complex (633.8 mg, 4.56 mmol, 1.5 eq) was added, and the reaction mixture was stirred at room temperature under nitrogen atmosphere for 24 h. The reaction mixture was quenched with MeOH (20 mL). The mixture was then concentrated under vacuum. The residue was purified by column chromatography on silica gel (10% MeOH and 1% H$_2$O in CH$_2$Cl$_2$, then 20% MeOH and 2% H$_2$O in CH$_2$Cl$_2$) to give sulfate compound (1.2 g, 1.63 mmol) in 53.6% yield.

Sulfate compound (1 g, 1.35 mmol) was solubilized in 1:1 methanol—water (100 mL) at room temperature. An aqueous solution of 0.1 M NaOH was added in increments of 0.1 equiv of NaOH until the pH of the solution reached approximately 8 (pH paper). The pH was maintained by incremental additions of the 0.1 M NaOH solution as the reaction proceeded (every 15-30 min). It is probably important not to go to high in pH as this may result in some hydrolysis of the sulfate ester. The reaction mixture was stirred for overnight (about 2 eq NaOH added), after which it was concentrated under vacuum to remove methanol and water. The residue was purified by column chromatography on silica gel (10% MeOH and 1% H$_2$O in CH$_2$Cl$_2$, then 20% MeOH and 2% H$_2$O in CH$_2$Cl$_2$) to give MPS-II-S (0.77 g, 1.06 mmol) in 79% yield.

Removal of non-sulfated material from the sulfated material can be performed by extraction or ion exchange chromatography as described below.

Extraction clean up. The compound from the silica gel (0.77 g, 1.06 mmol) was dissolved in pure water (200 mL) and 1M HCl was added dropwise to adjust pH to 2.7 by pH meter. The water layer was extracted with EtOAc (5×200 mL). The remaining water layer was transferred to a round bottom flask which was placed on a rotary evaporator with a 30° C. water bath and water aspiration for 30 min to remove traces of EtOAc from the water layer. The water layer was lyophilized. LC-MSMS on the 5 EtOAc extracts showed a about 100-fold drop in non-sulfated material in the 3$^{rd}$ extract compared to the first one. The amount in the 4$^{th}$ and 5$^{th}$ extracts were low and similar to the amount in the 3$^{rd}$ extract.

Ion exchange purification. AKTA using solvent A (MeOH) and solvent B (MeOH+1 M ammonium formate). Use commercial Pharmacia HiLoad 26/10 Q-Sepharose column at 3 ml/min. About 10 mg of MPS-II-IS-Pent-C6-d5 was injected in about 0.5 mL onto the column and held at 100% A for 20 min then a linear gradient was run from 0 to 100% B over 30 min and hold at 100% B (elution at 51 min).

22 mg of MPS-II-S-Pent-C6 in 1.5mL MeOH was injected using the above program (2 ml loop). Substrate elutes at 100 min. Rotovap off MeOH (water aspirator 25-30° C. water bath). The residue was dissolved in about 10 mL water and load onto a Waters C18 Sep-Pak (50 g size) that was previously washed with about 100 mL MeOH than about 100 mL water, wash with about 200 mL water (OD280 nm is close to 0). Compound was eluted with about 200 mL MeOH, additional MeOH had OD280 close to 0, methanol was removed by rotoevaporation (water aspirator, 30 deg C water bath). The residue dissolved in a few mL MeOH and transfer to 2×5 mL glass vials (more MeOH was used to complete the transfer) and subjected to Speed-Vac overnight without heat.

Example 2

Representative Assay using MPS-I Reagents

In this example, a representative assay using MPS-I reagents of the invention is described. The results for these reagents is compared to other MPS-I reagents.

The original MPS-I reaction is shown below (Blanchard, Sophie, Sadilek, Martin, Scott, C. Ronald, Turecek, Frantisek, and Gelb, Michael H. (2008) "Tandem mass spectrometry for the direct assay of Lysosomal enzymes in dried blood spots: Application to screening newborns for Mucopolysaccharidosis I," Clin. Chem., 54:2067-2070.). Note that the S, P and IS have the BOC group and that the P and IS are not chemically identical (the P has 4 CH2 groups in the linker whereas the IS has 3).

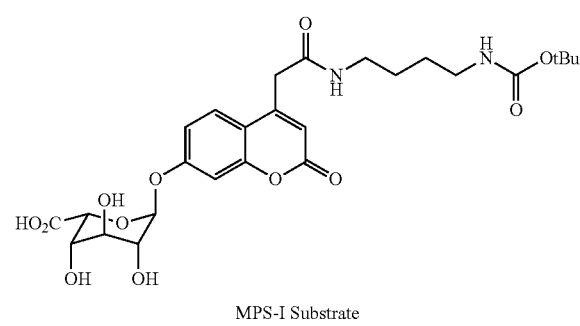

MPS-I Substrate

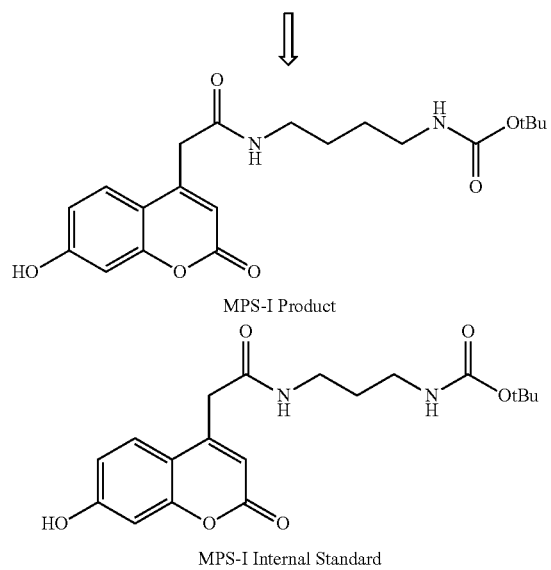

MPS-I Product

MPS-I Internal Standard

An alternative MPS-I reaction is shown below:

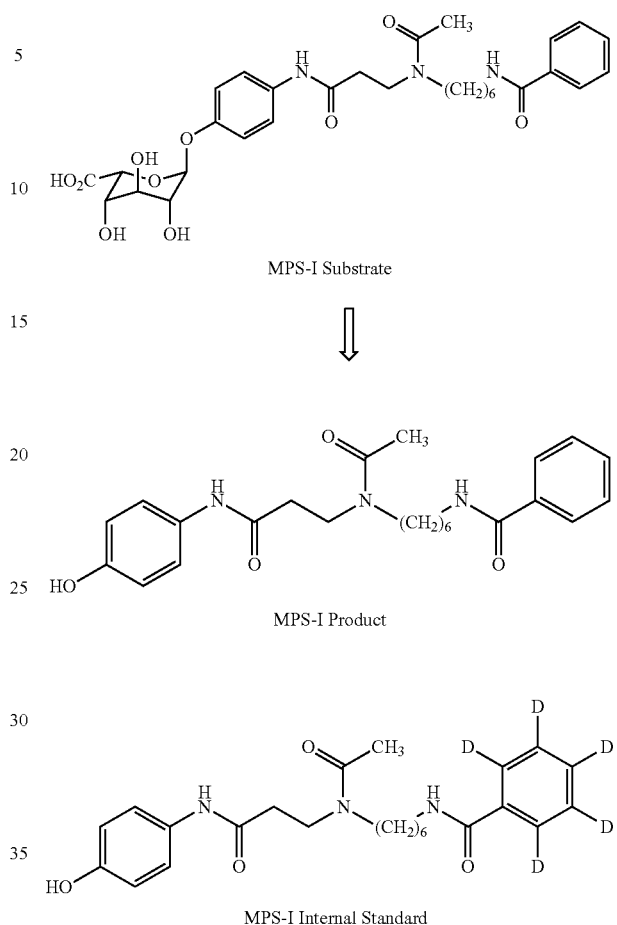

MPS-I Substrate

MPS-I Product

MPS-I Internal Standard

Note the different aglycone that has an N-acetyl group, no BOC carbamate group. Note also that the internal standard is chemically identical to the product but has 5 deuteriums in the benzoyl group.

The original and alternative MPS-I substrates were compared in side-by-side enzyme assays as follows: 0.5 mM substrate, 3.5 uM internal standard in 30 uL of buffer (100 mM ammonium formate, pH 4.0). A 3 mm punch of a dried blood spot was added, and the mixtures were incubated with shaking for 16 hours at 37 deg C. The reactions were quenched by addition 120 uL of acetonitrile. The wells were centrifuged, and 120 uL of supernatant was transferred to a new well. The sample was diluted by addition of 120 uL of water, and 10 uL was injected onto the LC/MSMS system. The LC and MS/MS conditions are as published (Spacil, Z., Tatipaka, H., Barcenas, M., Scott, C. R., Turecek, F., Gelb, M. H. (2012) "High-Throughput Assay of 9 Lysosomal Enzymes for Newborn Screening." Clinical Chemistry., 59 (3), 1530-8561). A blank assay is also carried out in which a blood-free 3 mm punch of filter paper is substituted for the dried blood spot. The blank is incubated and processed as above.

TABLE 3

Comparative MPS-I Assay Results.

| Substrate | Enzymatic Activity[1] (umole/hr/ L blood) | Coeff. of Variation on activity[2] | MSMS response of IS and P[3] (ion counts/ pmole) | blood-no blood assay ratio[4] |
|---|---|---|---|---|
| Original MPS-I | 2.4 | 9.4 | 100 | 21 |
| Alternative MPS-I | 2.5 | 5.5 | 500 | 34 |

[1]Enzymatic activity is expressed as umoles of product formed per hour per liter of blood.

[2]Coefficient of Variation (CV) is based on 6 runs of the assay each carried out with a different punch from the same dried blood spot.

[3]MSMS response is the amount of ion counts measured in the tandem mass spectrometry channel per pmole of analyte.

[4]Blood-no blood assay ratio is the enzymatic activity measured in an assay with a dried blood spot punch to that measured with a blood-free punch.

It can be seen from the above table that both MPS-I substrates display similar activity on the MPS-I enzyme (umoles product produced per hr per liter of blood) but that the alternative substrate gives rise to a product that is about 5-fold more sensitive in MSMS detection (ion counts detected per pmole of analyte). Similar results were obtained by flow injection-MSMS. The MSMS response for the alternative MPS-I product and internal standard was about 5-fold higher than the original ones (not shown).

The MSMS response of the MPS-I product was compared to the Fabry assay product (structures shown below).

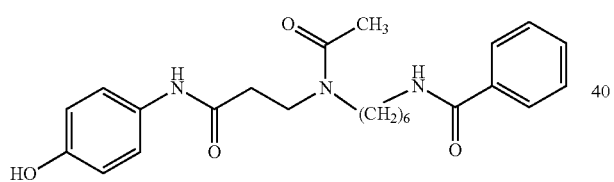

MPS-I Product

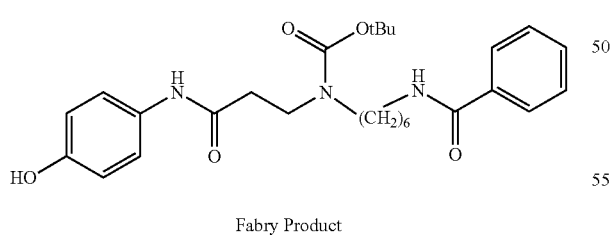

Fabry Product

Note the MPS-I product has an acetyl on the amine, whereas the Fabry product has the BOC carbamate. The BOC carbamate partially decomposes in the electrospray ionization source of the MSMS instrument due to loss of isobutylene and $CO_2$ to produce the decomposition product with the BOC replaced with H. The Fabry product gives 211 ion counts per pmole, whereas the MPS-I product gives 500 ion counts per pmole.

Example 3

Representative Assay using MPS-II Reagents

In this example, a representative assay using MPS-II reagents of the invention is described. The results for these reagents are compared to other MPS-II reagents.

The original MSP-II reaction is shown below (Wolfe, B. J., Blanchard, S., Sadilek, M., Scott, C. R., Turecek, F., Gelb, M. H. (2011) "Tandem mass spectrometry for the direct assay of Lysosomal enzymes in dried blood spots: Application to screening newborns for Mucopolysaccharidosis II (Hunter Syndrome)" Anal. Chem., 83:1152-1156.). Note that the S, P and IS have the BOC group.

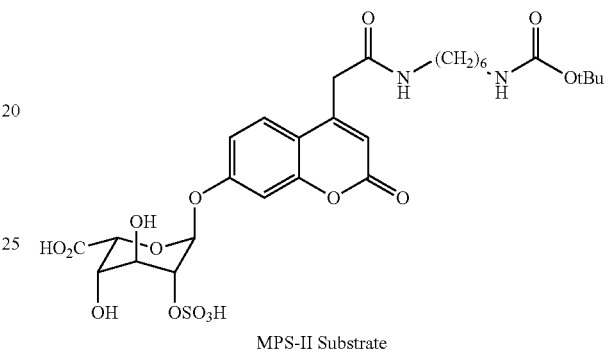

MPS-II Substrate

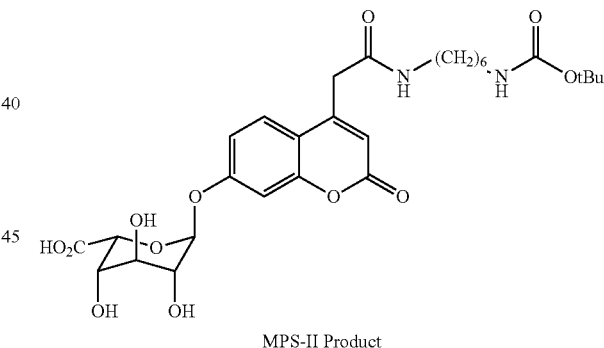

MPS-II Product

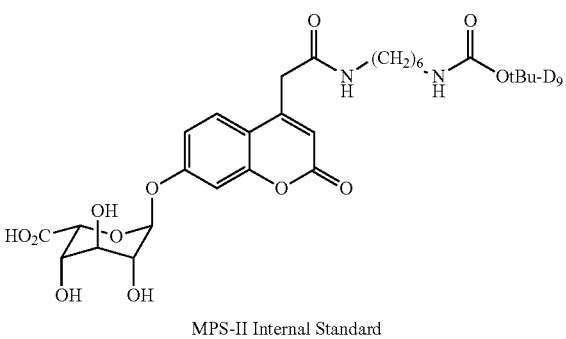

MPS-II Internal Standard

The alternative MPS-II reaction is shown below:

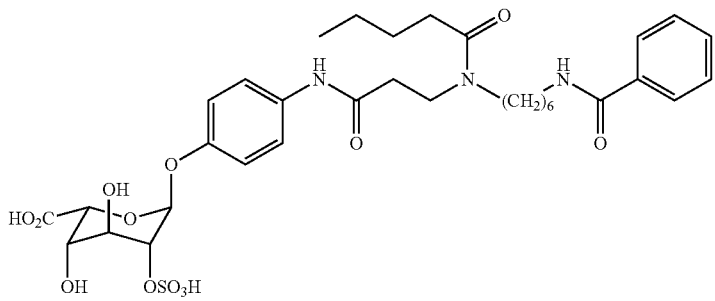

MPS-II Substrate

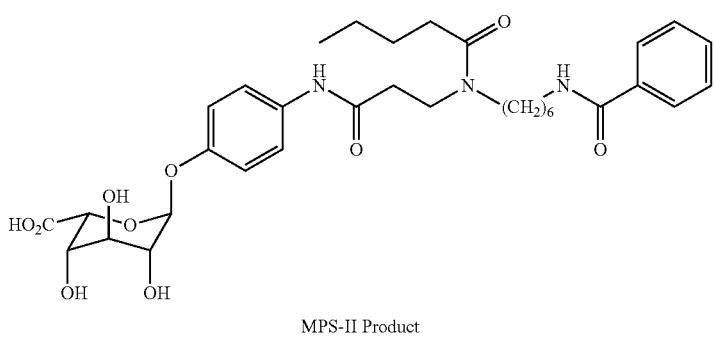

MPS-II Product

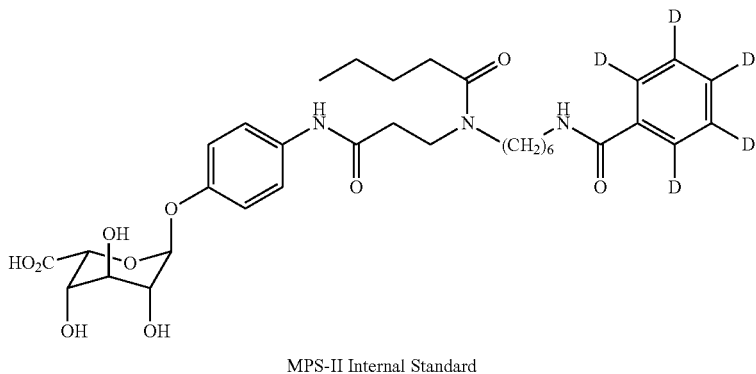

MPS-II Internal Standard

Note the different aglycone that has an N-pentanoyl group and lacks a BOC carbamate group. Note also that the internal standard is chemically identical to the product but has 5 deuteriums in the benzoyl group.

The original and alternative MPS-II substrates were compared in side-by-side enzyme assays as follows: 1 mM substrate, 5 uM internal standard in 30 uL of buffer (100 mM ammonium formate, pH 4.0, 7.5 mM barium(II) acetate, 5.0 mM cerium(III) acetate). A 3 mm punch of a dried blood spot was added, and the mixtures were incubated with shaking for 16 hours at 37 deg C. The reactions were quenched by addition of 200 uL of 44 mM citric acid followed by addition of 400 uL ethyl acetate and 100 uL of water. After mixing up and down a few times with the pipet, the samples were centrifuged (10 min at 3000 rpm) to separate the liquid layers. A 200 uL portion of the upper ethyl acetate layer was transferred to a new well, and solvent was removed by evaporation with a stream of oil-free air. The residue was taken up in 100 uL of methanol/5 mM aqueous ammonium formate (80/20, v/v) and infused into the tandem mass spectrometer. The barium and cerium salts are present to precipitate free sulfate and phosphate present in the dried blood spot since these anions cause production inhibition of the MPS-II enzyme. The citric acid is used to acidify the mixture so that the carboxylate of the iduronic acid portion of the MPS-II product and internal standard is protonated and is extracted into ethyl acetate. A blank assay is also carried out in which a blood-free 3 mm punch of filter paper is substituted for the dried blood spot. The blank is incubated and processed as above.

TABLE 4

Comparative MPS-II Assay Results.

| Substrate | Enzymatic Activity[1] (umole/hr/L blood) | Coeff. of Variation on activity[2] | MSMS response of IS and P[3] (ion counts/pmole) | blood-no blood assay ratio[4] |
|---|---|---|---|---|
| Original MPS-II | 5 | 6 | 8.6 | 45 |
| Alternative MPS-II | 6 | 12 | 86 | 53 |

[1]Enzymatic activity is expressed as umoles of product formed per hour per liter of blood.
[2]Coefficient of Variation (CV) is based on 6 runs of the assay each carried out with a different punch from the same dried blood spot.
[3]MSMS response is the amount of ion counts measured in the tandem mass spectrometry channel per pmole of analyte.
[4]Blood-no blood assay ratio is the enzymatic activity measured in an assay with a dried blood spot punch to that measured with a blood-free punch.

It can be seen from the above table that both MPS-II substrates display similar activity on the MPS-II enzyme (umoles product produced per hr per liter of blood) but that the alternative substrate gives rise to a product that is about 10-fold more sensitive in MSMS detection (ion counts detected per pmole of analyte).

Example 4

Synthesis of Representative MPS-IVA Substrates and Enzymatic Products

Figure 2:
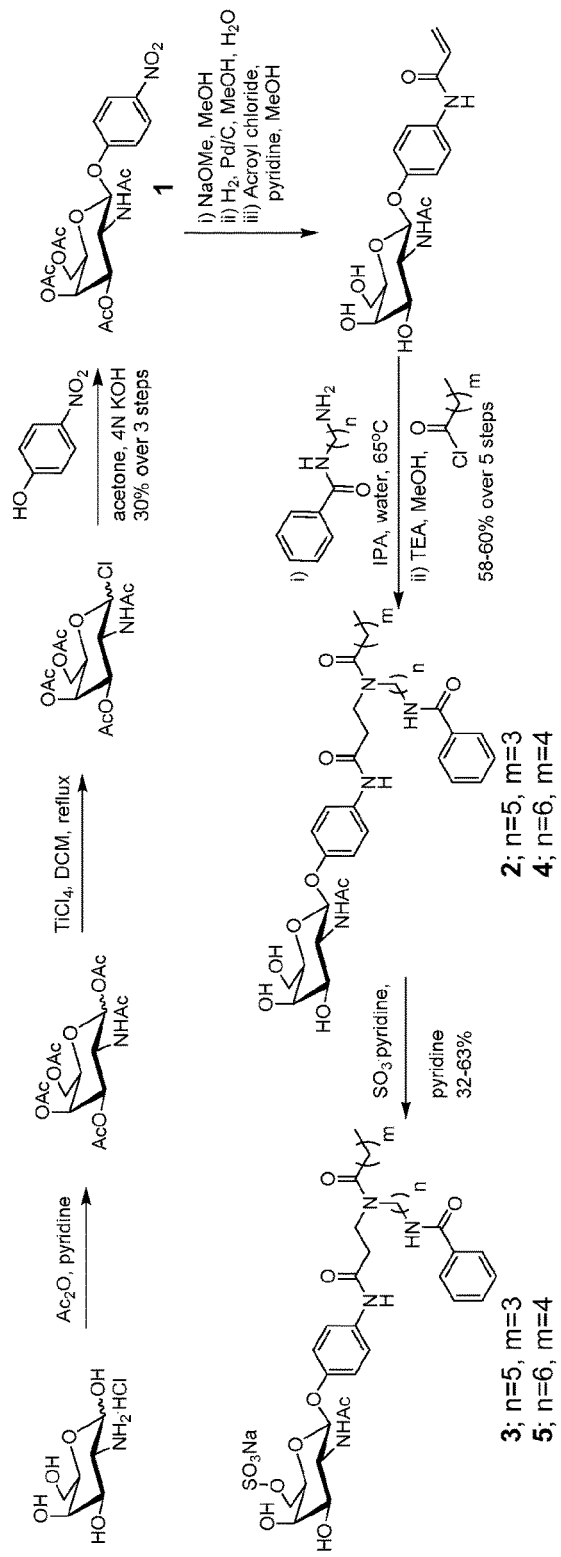
FIG. 2 is schematic illustration of the preparation of representative MPS-IVA substrates of the invention.

In this example, the synthesis of representative MPS-IVA substrate reagents is described. The general scheme for the synthesis of MPS-WA substrates is shown in FIG. 2.

(2R,3R,4R,5R,6S)-5-acetamido-2-(acetoxymethyl)-6-(4-nitrophenoxy)tetrahydro-2H-pyran-3,4-diyl diacetate (1)

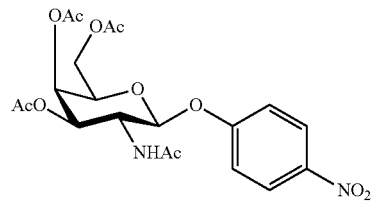

Pyridine (60 mL) was added to nitrogen back flushed flask containing D-galactosamine hydrochloride (5 g, 23.2 mmol) and the resultant slurry was cooled on an ice bath. To the cooled mixture acetic anhydride (25 g, 245 mmol) was added dropwise and allowed to warm to room temperature followed by stirring at this temperature for 16 hours. The reaction mixture was quenched with the addition of methanol (15 mL) and let stir for 20 minutes. The resultant mixture was concentrated under reduced pressure and the residue was dissolved in 20% methanol in chloroform with the aid of warming the mixture. This solution was washed with 1N HCl solution followed by brine solution. The resultant organic layer was dried using anhydrous sodium sulfate and concentrated under reduced pressure. The residue was taken in nitrogen back flushed flask equipped with a dropping funnel. Anhydrous dichloromethane (100 mL) was added to this residue and the resultant slurry was cooled on an ice bath. In the dropping funnel titanium chloride (6.5 g, 42.1 mmol) was dissolved in anhydrous dichloromethane (40 mL) and the resulting solution was added dropwise to the cooled solution. The reaction mixture was warmed to 50° C. in an oil bath and left to stir at this temperature for 48 hours. The reaction mixture was cooled back on an ice bath and saturated sodium bicarbonate solution was added dropwise with vigorous shaking. The resultant mixture was extracted between dichloromethane and saturated sodium bicarbonate solution. The organic layer was dried using anhydrous sodium sulfate and concentrated under reduced pressure. The resultant residue was dissolved in acetone (60 mL) and added slowly to a solution of 4-nitrophenol (16.1 g, 116 mmol) in acetone (130 mL) and 4N KOH aqueous solution (23.2 mL). The reaction was left to stir at room temperature for 48 hours and concentrated under reduced pressure to less than 20 mL. This solution was extracted between 1N NaOH and chloroform. The organic layer was dried using anhydrous sodium sulfate and concentrated under reduced pressure. The crude product thus obtained was purified by silica flash chromatography using 3% methanol in dichloromethane as the elution mixture. The fractions with the desired compound, as determined by TLC, were combined and concentrated under reduced pressure to get 1 (3.29 g, 30%). $^1$H NMR (300 MHz, CDCl$_3$) δ 8.20 (d, J=9.1 Hz, 2H), 7.09 (d, J=9.1 Hz, 2H), 5.61 (d, J=8.0 Hz, 1H), 5.56-5.39 (m, 3H), 4.32-4.07 (m, 4H), 2.18 (s, 3H), 2.07 (s, 3H), 2.04 (s, 3H), 1.97 (s, 3H). MS (EST$^+$) for [M+Na]$^+$; calculated: 491.1, found: 491.2.

N-(5-(N-(3-(4-(((2S,3R,4R,5R,6R)-3-acetamido-4,5-dihydroxy-6-(hydroxymethyl)tetrahydro-2H-pyran-2-yl)oxy)phenyl)amino)-3-oxopropyl)pentanamido)pentyl)benzamide (2)

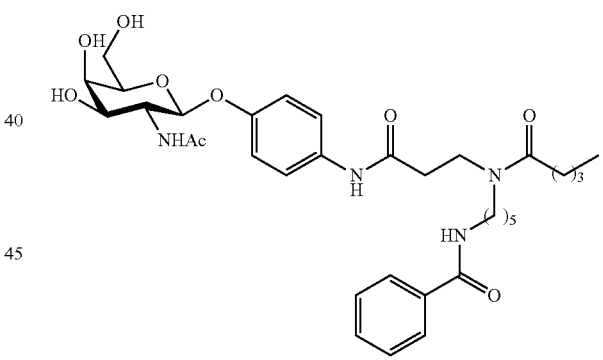

To a solution of 1 (3.5 g, 7.47 mmol) in anhydrous methanol (90 mL), cooled on an ice bath, 0.5 M sodium methoxide solution in methanol (3 mL, 1.50 mmol) was added dropwise and allowed to warm to room temperature. After 2 hours formic acid (0.1 mL) was added to the reaction mixture and concentrated to dryness under reduced pressure. To the resulting residue methanol (135 mL), water (15 mL) and 10% palladium on activated carbon (125 mg) was added and let to stir under a hydrogen atmosphere at room temperature for 16 hours. Water was added dropwise to the reaction mixture till the entire white residue was completely dissolved. The reaction mixture was filtered and the filtrate was cooled on an ice bath. To it pyridine (2 mL) and followed by the dropwise addition of a solution of acryloyl chloride (2.1 g, 23.2 mmol) in dichloromethane (50 mL). The reaction was let to stir on the ice bath for 30 minutes and then warmed to room temperature and continued for 2 hours.

Sodium carbonate powder (3.0 g) was added to the reaction mix and let to stir for 15 minutes and filtered. The filtrate was concentrated under reduced pressure and further dried under high vacuum. The residue was dissolved in 2-propanol (50 mL) and water (6.6 mL) mixture and to it N-(5-aminopentyl)benzamide (2.0 g, 9.69 mmol) was added and let to stir for 40 hours at 65° C. The reaction mixture was cooled to room temperature and methanol (25 mL) was added to it. Upon cooling this mixture on an ice bath triethylamine (2.5 mL) was added followed by the dropwise addition of a solution of pentanoyl chloride (2.7 g, 22.4 mmol) in dichloromethane (50 mL). The reaction was left to stir on the ice bath for 30 minutes and then warmed to room temperature and continued for 16 hours. The reaction mixture was concentrated under reduced pressure and subjected to purification by silica flash chromatography using 15% methanol in dichloromethane as the elution mixture to yield 2 (2.96 g, 60%). $^1$H NMR (300 MHz, MeOD) δ 7.84 (d, J=7.1 Hz, 2H), 7.59-7.35 (m, 5H), 7.09-6.91 (m, 2H), 5.00 (d, J=8.4 Hz, 1H), 4.28-4.09 (m, 1H), 3.97-3.55 (m, 7H), 3.46-3.24 (m, 4H), 2.72-2.51 (m, 2H), 2.49-2.28 (d, J=7.3 Hz, 2H), 2.02 (s, 3H), 1.78-1.49 (m, 6H), 1.49-1.22 (m, 4H), 0.94 (t, J=7.1 Hz, 3H). MS (ESI$^+$) for [M+H]$^+$; calculated: 657.3, found: 657.5.

Sodium ((2R,3R,4R,5R,6S)-5-acetamido-6(4(3(N (5-benzamidopentyl)-pentanamido)propanamido) phenoxy)-3,4-dihydroxytetrahydro-2H-pyran-2-yl) methyl sulfate (3)

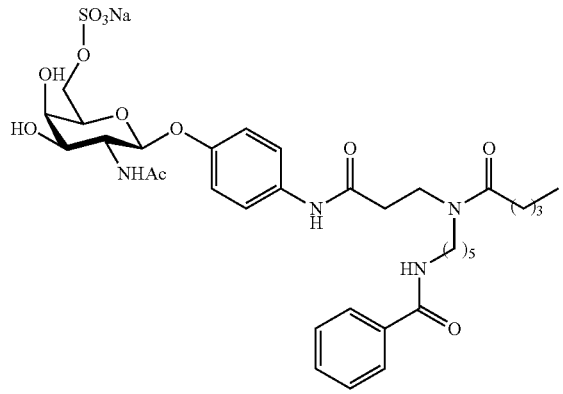

To compound 2 (32 mg, 0.048 mmol) under nitrogen anhydrous pyridine (1 mL) was added. To this solution sulfur trioxide pyridine complex (18 mg, 0.113 mmol) was added and let to stir for 5 hours at room temperature. The reaction was quenched with the addition of methanol (0.3 mL) and stirring for 30 minutes. The reaction mixture was concentrated under reduced pressure and redissolved in water and subjected to reversed phase (C18) HPLC purification using water-methanol gradient system to get 3 (23 mg, 63%). $^1$H NMR (300 MHz, MeOD) δ 7.81 (d, J=7.3 Hz, 2H), 7.57-7.39 (m, 5H), 7.00 (dd, J=9.0, 2.4 Hz, 2H), 4.93 (d, J=8.5 Hz, 1H), 4.38-4.12 (m, 3H), 3.95 (t, J=4.5 Hz, 2H), 3.83-3.61 (m, 3H), 3.49-3.34 (m, 4H), 2.72-2.54 (m, 2H), 2.50-2.30 (m, 2H), 1.98 (s, 3H), 1.78-1.49 (m, 6H), 1.49-1.24 (m, 4H), 1.02-0.84 (m, 3H). MS (ESI$^-$) for [M-Na$^+$]$^-$; calculated: 735.3, found: 735.5.

N-(6-(N-(3-(4-(((2S,3R,4R,5R,6R)-3-acetamido-4,5-dihydroxy-6-(hydroxymethyl)tetrahydro-2H-pyran-2-yl)oxy)phenyl)amino)-3-oxopropyl)hexanamido) hexyl)benzamide (4)

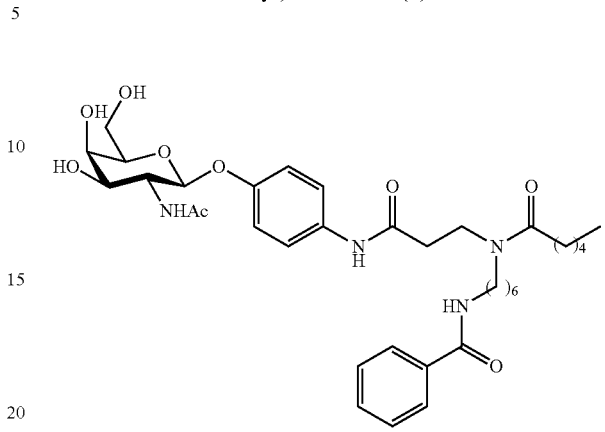

To a solution of 1 (0.27 g, 0.576 mmol) in anhydrous methanol (9 mL), cooled on an ice bath, 0.5 M sodium methoxide solution in methanol (0.3 mL, 0.15 mmol) was added dropwise and allowed to warm to room temperature. After 2 hours formic acid (10 μL) was added to the reaction mixture and concentrated to dryness under reduced pressure. To the resulting residue methanol (13.5 mL), water (1.5 mL) and 10% palladium on activated carbon (12.5 mg) was added and let to stir under a hydrogen atmosphere at room temperature for 16 hours. Water was added dropwise to the reaction mixture till the entire white residue was completely dissolved. The reaction mixture was filtered and the filtrate was cooled on an ice bath. To it pyridine (0.16 mL) and followed by the dropwise addition of a solution of acryloyl chloride (0.16 g, 1.76 mmol) in dichloromethane (4 mL). The reaction was let to stir on the ice bath for 30 minutes and then warmed to room temperature and continued for 2 hours. Sodium carbonate powder (0.3 g) was added to the reaction mix and let to stir for 15 minutes and filtered. The filtrate was concentrated under reduced pressure and further dried under high vacuum. The residue was dissolved in 2-propanol (6.3 mL) and water (0.7 mL) mixture and to it N-(6-aminohexyl)benzamide (0.17 g, 0.77 mmol) was added and let to stir for 40 hours at 65° C. The reaction mixture was cooled to room temperature and methanol (8 mL) was added to it. Upon cooling this mixture on an ice bath triethylamine (0.25 mL) was added followed by the dropwise addition of a solution of hexanoyl chloride (0.24 g, 1.78 mmol) in dichloromethane (4 mL). The reaction was left to stir on the ice bath for 30 minutes and then warmed to room temperature and continued for 16 hours. The reaction mixture was concentrated under reduced pressure and subjected to purification by silica flash chromatography using 15% methanol in dichloromethane as the elution mixture to yield 4 (0.23 g, 58%). $^1$H NMR (300 MHz, MeOD) δ 7.80 (d, J=6.9 Hz, 2H), 7.56-7.39 (m, 5H), 6.99 (d, J=9.1 Hz, 2H), 4.96 (d, J=8.4 Hz, 1H), 4.17 (dd, J=10.7, 8.4 Hz, 1H), 3.96-3.51 (m, 7H), 3.44-3.33 (m, 4H), 2.69-2.50 (m, 2H), 2.48-2.28 (m, 2H), 1.98 (s, 3H), 1.72-1.49 (m, 6H), 1.49-1.21 (m, 9H), 0.89 (dt, J=8.7, 4.8 Hz, 3H). MS (ESI$^+$) for [M +H]$^+$; calculated: 685.4, found: 685.5.

Sodium ((2R,3R,4R,5R,6S)-5-acetamido-6(4(3-(N (6-benzamidohexyl)-hexanamido)propanamido)phenoxy)-3,4-dihydroxytetrahydro-2H-pyran-2-yl) methyl sulfate (5)

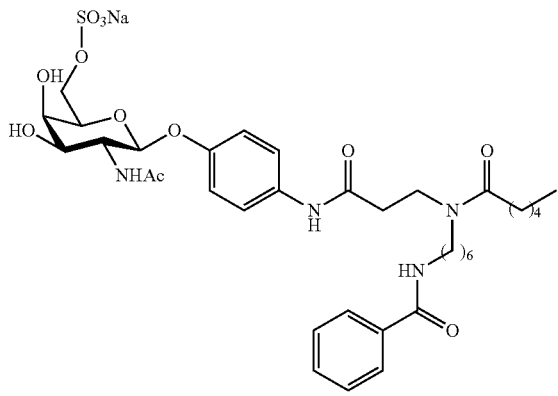

To compound 4 (99 mg, 0.144 mmol) under nitrogen anhydrous pyridine (5 mL) was added. To this solution sulfur trioxide pyridine complex (34 mg, 0.214 mmol) was added and let to stir for 5 hours at room temperature. The reaction was quenched with the addition of methanol (0.5 mL) and stirring for 30 minutes. The reaction mixture was concentrated under reduced pressure and redissolved in water and subjected to reversed phase (C18) HPLC purification using water-methanol gradient system to get 3 (36 mg, 32%). $^1$H NMR (300 MHz, MeOD) δ 7.81 (d, J=6.9 Hz, 2H), 7.59-7.35 (m, 5H), 7.00 (d, J=9.0 Hz, 2H), 4.93 (d, J=8.4 Hz, 1H), 4.32-4.10 (m, 3H), 4.03-3.90 (m, 2H), 3.83-3.60 (m, 3H), 3.44-3.33 (m, 4H), 2.61 (q, J=7.0 Hz, 2H), 2.49-2.29 (m, 2H), 1.98 (s, 3H), 1.72-1.49 (m, 6H), 1.48-1.22 (m, 9H), 0.98-0.81 (m, 3H). MS (ESL) for [M-Na$^+$]$^-$; calculated: 763.3, found: 763.7.

Example 5

Synthesis of Representative MPS-VI Substrates and Enzymatic Products

Figure 3:
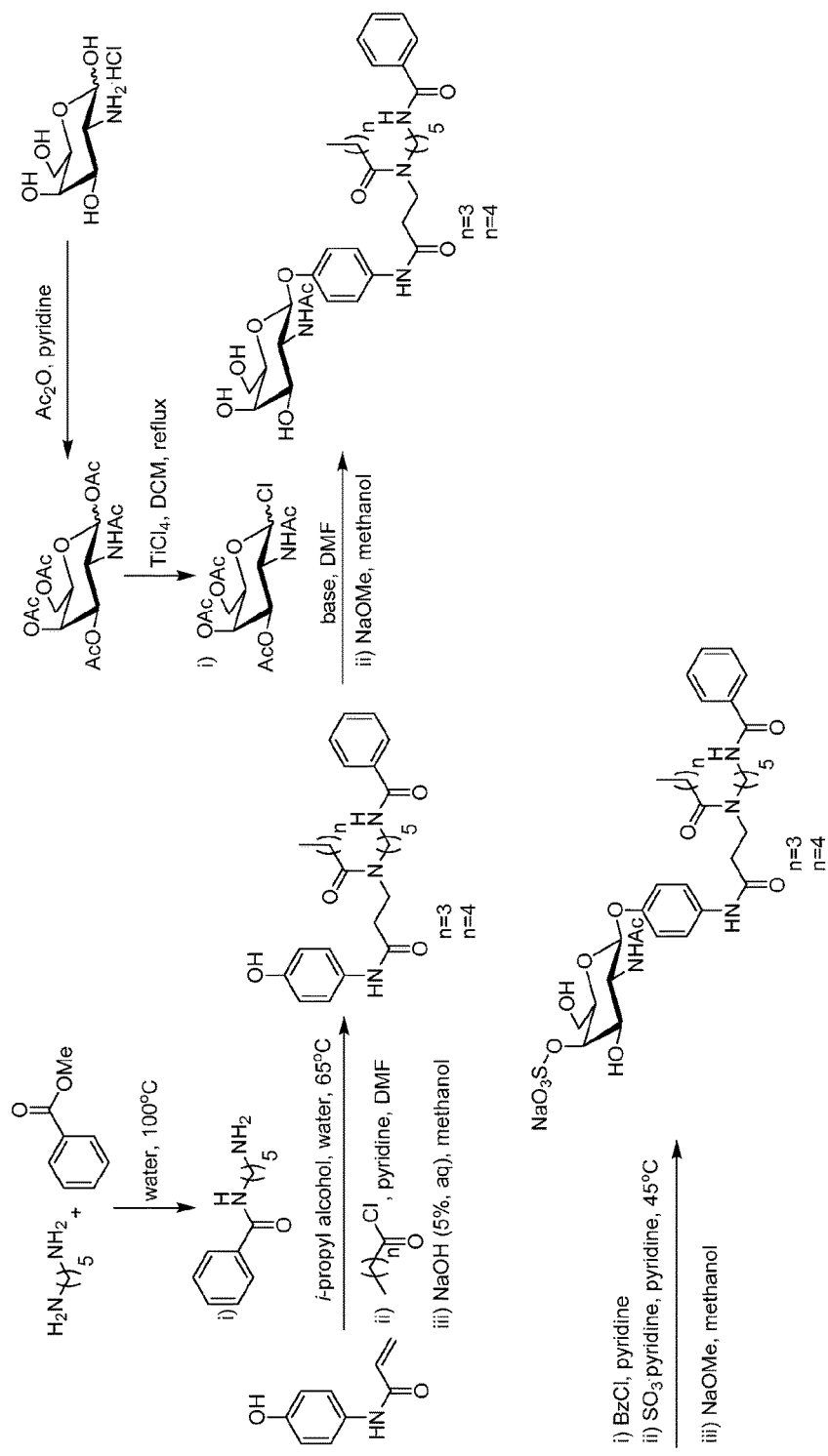
FIG. 3 is schematic illustration of the preparation of representative MPS-VI substrates of the invention.

In this example, the synthesis of representative MPS-VI substrates and enzymatic product reagents is described. The general scheme for the synthesis of MPS-VI substrates is shown in FIG. 3.

Figure 4:
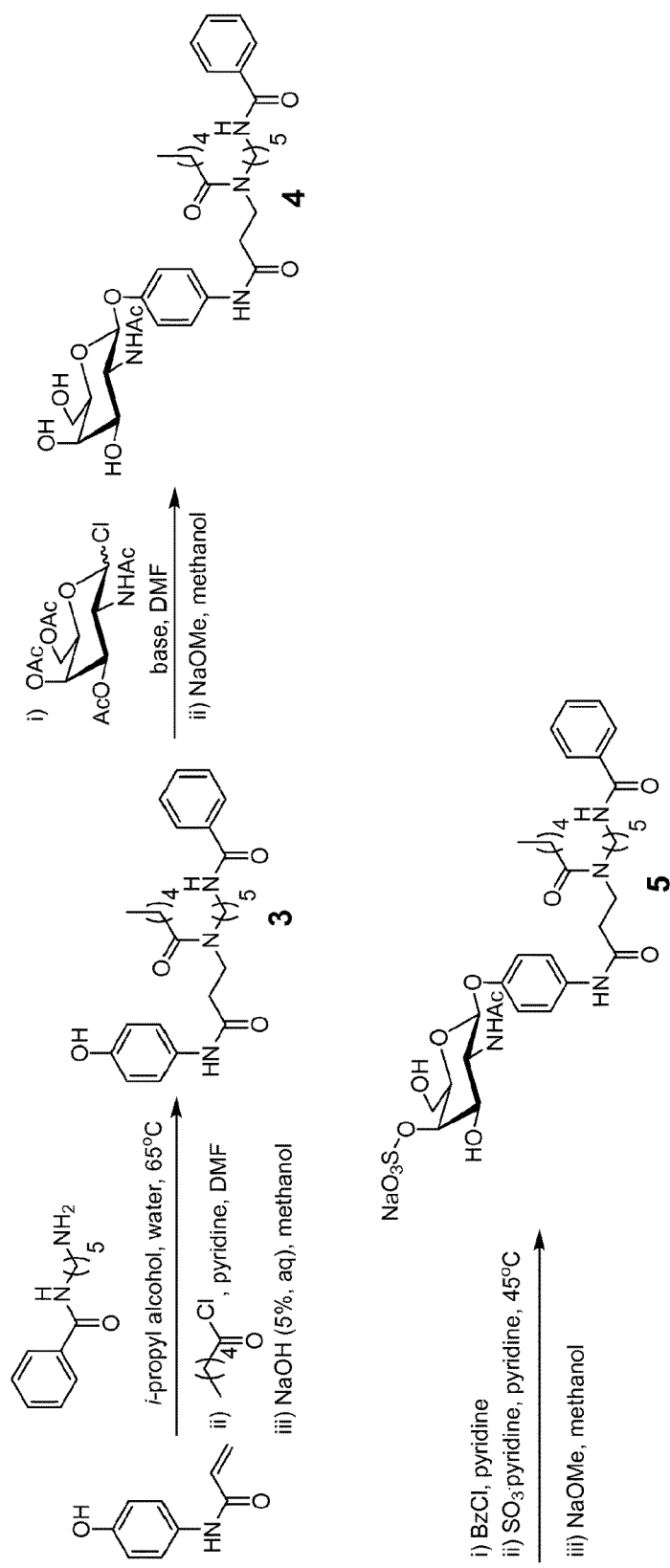
FIG. 4 is schematic illustration of the preparation of representative MPS-VI substrates of the invention.

MPS-VI substrate (hexanamido). The preparation of a representative MPS-VI substrate (hexanamido) is described below and illustrated in FIG. 4.

N-(5-(N-(3-((4-hydroxyphenyl)amino)-3-oxopropyl) hexanamido)pentyl)-benzamide (3)

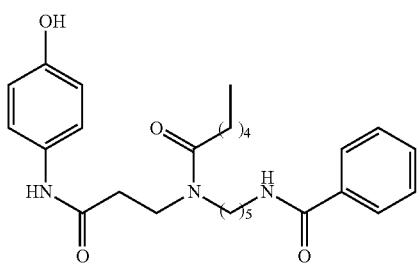

A solution of N-(5-aminopentyl)benzamide (180 mg, 0.872 mmol) and N-(4-hydroxyphenyl)acrylamide (171 mg, 1.05 mmol) in i-propyl alcohol (7.8 mL) and water (0.87 mL) was heated to 65° C. under constant stirring for 24 hours. The reaction mixture was cooled to room temperature and concentrated under reduced pressure and further under high vacuum. To this crude concentrate anhydrous N,N-dimethylformamide (DMF) (3.0 mL) and triethylamine (220 mg, 2.17 mmol) were added and dissolved thoroughly. This solution was cooled to 0° C. and hexanoyl chloride (234 mg, 1.74 mmol) was added dropwise and warmed to room temperature and stirred for 2 hours. The reaction was quenched with the addition of saturated sodium bicarbonate solution and the reaction mixture was extracted with DCM/methanol (4:1). The organic layer was further washed with water and dried with anhydrous sodium sulfate. The organic layer was concentrated to dryness under reduced pressure and methanol (3.0 mL) was added and re-dissolved. To this solution 5% aqueous sodium hydroxide (3.0 mL) was added dropwise and stirred at room temperature for 2 hours. The reaction was acidified, as indicated by pH paper, with 1N HCl solution and extracted with DCM/methanol (4:1). The organic layer was concentrated under reduced pressure and the residue was subjected to silica column chromatography and eluted with 5% methanol in DCM to yield 3 (151 mg, 37%). $^1$H NMR (300 MHz, MeOD) δ 8.47 (s, 1H), 7.81 (d, J=7.7 Hz, 2H), 7.57-7.40 (m, 3H), 7.36-7.27 (m, 2H), 6.78-6.67 (m, 2H), 3.69 (dt, J=18.7, 6.9 Hz, 2H), 3.46-3.33 (m, 4H), 2.60 (q, J=7.0 Hz, 2H), 2.47-2.29 (m, 2H), 1.63 (ddd, J=11.6, 10.6, 5.7 Hz, 6H), 1.48-1.22 (m, 6H), 0.89 (td, J=6.6, 2.6 Hz, 3H). MS (ESI$^+$) for [M+Na]$^+$; calculated: 490.3, found: 490.6.

N-(5-(N-(3-(4-(((2S,3R,4R,5R,6R)-3-acetamido-4,5-dihydroxy-6-(hydroxymethyl)tetrahydro-2H-pyran-2-yl)oxy)phenyl)amino)-3-oxopropyl)hexanamido) pentyl)benzamide (4)

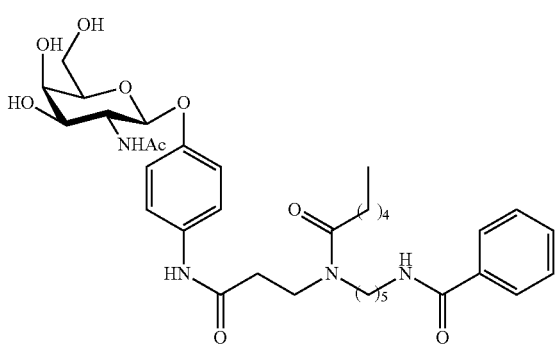

To a solution of 3 (73 mg, 0.156 mmol) and (2R,3R,4R, 5R)-5-acetamido-2-(acetoxymethyl)-6-chlorotetrahydro-2H-pyran-3,4-diyl diacetate (114 mg, 0.312 mmol) in anhydrous DMF (0.7 mL) cesium carbonate (152 mg, 0.466 mmol) was added and left to stir for 6 hours at room temperature. The reaction mixture was then extracted between water and DCM and the organic layer was further washed with water, dried with anhydrous sodium sulfate and concentrated under reduced pressure. The resultant crude was purified by flash silica column chromatography using 4% methanol in DCM as eluent to get the peracetylated intermediate. The NMR spectroscopy indicated that the peracetylated intermediate has co-eluted with the starting material 3. This mixture was used for the next deacetylation step without further purification. To the solution of the above mixture in anhydrous methanol (5.0 mL), a 0.5 M solution of sodium methoxide in methanol (200 μL) was added dropwise at 0° C. and left to stir for 2 hours at room temperature. The reaction was quenched with the addition of formic acid (100 μL) and subjected to semi-preparative reverse phase HPLC purification (gradient water/methanol system) to get 4 (23 mg, 22%). $^1$H NMR (300 MHz, MeOD) δ 7.85-7.77 (m, 2H), 7.58-7.38 (m, 5H), 6.99 (dd, J=9.1, 2.6 Hz, 2H), 4.96 (dd, J=8.4, 1.3 Hz, 1H), 4.17 (dd, J=10.7, 8.4 Hz, 1H), 3.90 (d, J=3.1 Hz, 1H), 3.84-3.60 (m, 6H), 3.38 (dd, J=11.1, 6.8 Hz, 4H), 2.61 (q, J=7.1 Hz, 2H), 2.47-2.29 (m, 2H), 1.98 (s, 3H), 1.74-1.50 (m, 6H), 1.47-1.21 (m, 6H), 0.89 (td, J=6.6, 3.3 Hz, 3H). MS (ESI$^+$) for [M+Na]$^+$; calculated: 693.3, found: 693.4.

Sodium (2R,3R,4R,5R,6S)-5-acetamido-6(4(3(N (5-benzamidopentyl)-hexanamido)propanamido) phenoxy)-4-hydroxy-2-(hydroxymethyl)tetrahydro-2H-pyran-3-yl sulfate (5)

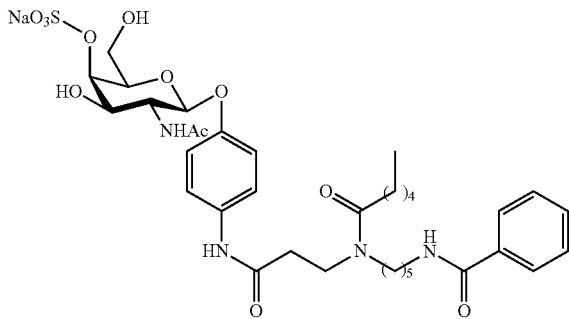

To a cooled (0° C.) solution of 4 (22 mg, 32.8 μmol) in anhydrous pyridine (0.5 mL), benzoyl chloride (7.7 μL, 65.6 μmol) was added. After 1 hour at room temperature the solution was cooled back to 0° C. and another portion of benzoyl chloride (7.7 μL, 65.6 μmol) was added left to stir for 2 hours at room temperature. The reaction was quenched with addition of methanol (200 μL) and stirred for another 30 mins. The resultant mixture was concentrated under reduced pressure and purified by flash silica column chromatography using 4% methanol in DCM as the eluent. The desired fractions were concentrated under reduced pressure and further under high vacuum. The resultant residue was dissolved in anhydrous pyridine (1.0 mL) and sulfur trioxide pyridine complex (17 mg, 109 μmol) was added to it at room temperature. The resulting mixture was heated to 45° C. for 3 hours followed by the addition of methanol (0.5 mL) and stirred for further 10 mins. The reaction mixture was concentrated under reduced pressure and further under high vacuum. The resulting residue was re-dissolved in anhydrous methanol (6.0 mL) and cooled to 0° C. To this cooled solution 0.5 M solution of sodium methoxide in methanol (0.8 mL) was added dropwise and let stir for 16 hours. The reaction was quenched by the addition of 1 M aqueous solution of sodium phosphate monobasic (1.0 mL) and subjected to semi-preparative reverse phase HPLC purification (gradient water/methanol system) to yield 5 (12 mg, 47%). $^1$H NMR (300 MHz, MeOD) δ 7.85-7.76 (m, 2H), 7.58-7.38 (m, 5H), 7.05-6.92 (m, 2H), 5.00 (dd, J=8.4, 1.2 Hz, 1H), 4.75 (d, J=3.1 Hz, 1H), 4.15 (dd, J=10.9, 8.4 Hz, 1H), 3.95-3.60 (m, 6H), 3.38 (dt, J=11.2, 5.6 Hz, 4H), 2.62 (dd, J=15.9, 6.9 Hz, 2H), 2.47-2.29 (m, 2H), 1.97 (s, 3H), 1.76-1.51 (m, 6H), 1.47-1.21 (m, 6H), 0.89 (td, J=6.6, 3.4 Hz, 3H). MS (ESI$^-$) for [M-Na$^+$]$^-$; calculated: 749.3, found: 749.5.

MPS-VI substrate (pentanamido). The preparation of a representative MPS-VI substrate (pentanamido) is described below and illustrated in FIG. 4.

N-(5-(N-(3-((4-hydroxyphenyl)amino)-3-oxopropyl) pentanamido)pentyl)-benzamide

A solution of N-(5-aminopentyl)benzamide (207 mg, 1.00 mmol) and N-(4-hydroxyphenyl)acrylamide (197 mg, 1.21 mmol) in i-propyl alcohol (9.0 mL) and water (1.0 mL) was heated to 65° C. under constant stirring for 24 hours. The reaction mixture was cooled to room temperature and concentrated under reduced pressure and further under high vacuum. To this crude concentrate anhydrous N,N-dimethylformamide (DMF) (3.0 mL) and triethylamine (253 mg, 2.50 mmol) were added and dissolved thoroughly. This solution was cooled to 0° C. and valeryl chloride (241 mg, 2.00 mmol) was added dropwise and warmed to room temperature and stirred for 2 hours. The reaction was quenched with the addition of saturated sodium bicarbonate solution and the reaction mixture was extracted with DCM/methanol (4:1). The organic layer was further washed with water and dried with anhydrous sodium sulfate. The organic layer was concentrated to dryness under reduced pressure and methanol (3.0 mL) was added and re-dissolved. To this solution 5% aqueous sodium hydroxide (3.0 mL) was added dropwise and stirred at room temperature for 2 hours. The reaction was acidified, as indicated by pH paper, with 1N HCl solution and extracted with DCM/methanol (4:1). The organic layer was concentrated under reduced pressure and the residue was subjected to silica column chromatography and eluted with 5% methanol in DCM to yield the title compound (203 mg, 45%). $^1$H NMR (300 MHz, MeOD) δ 8.45 (s, 1H), 7.83-7.78 (m, 2H), 7.56-7.40 (m, 3H), 7.34-7.26 (m, 2H), 6.76-6.68 (m, 2H), 3.69 (dt, J=19.4, 6.9 Hz, 2H), 3.44-3.37 (m, 4H), 2.60 (dd, J=14.7, 7.4 Hz, 2H), 2.47-2.30 (m, 2H), 1.75-1.49 (m, 6H), 1.47-1.26 (m, 4H), 0.91 (t, J=7.3 Hz, 3H). MS (ESI$^+$) for [M+Na]$^+$; calculated: 476.3, found: 476.5.

N-(5-(N-(3-(4-(((2S,3R,4R,5R,6R)-3-acetamido-4,5-dihydroxy-6-(hydroxymethyl)-tetrahydro-2H-pyran-2-yl)oxy)phenyl)amino)-3-oxopropyl)pentanamido) pentyl)benzamide To a solution of N-(5-(N-(3-((4-hydroxyphenyl)amino)-3-oxopropyl)pentanamido)pentyl)-benzamide (148 mg, 0.326 mmol) and (2R,3R,4R,5R)-5-acetamido-2-(acetoxymethyl)-6-chlorotetrahydro-2H-pyran-3,4-diyl diacetate (239 mg, 0.653 mmol) in DCM (0.4 mL) tetrabutylammonium hydrogen sulfate (110 mg, 0.324 mmol) and 2 M aqueous sodium hydroxide solution (0.4 mL) was added and left to stir for 3 hours at room temperature. To the reaction mixture another portion of the diacetate (90 mg, 0.246 mmol) was added and stirred for another 13 hours. The reaction mixture was then extracted between water and DCM and the organic layer was further washed with water, dried with anhydrous sodium sulfate and concentrated under reduced pressure. The resultant crude was purified by flash silica column chromatography using 4% methanol in DCM as eluent to get the peracetylated intermediate. The NMR spectroscopy indicated that the peracetylated intermediate has co-eluted with the starting material. This mixture was used for the next deacetylation step without further purification. To the solution of the above mixture in anhydrous methanol (5.0 mL), a 0.5 M solution of sodium methoxide in methanol (200 µL) was added dropwise at 0° C. and left to stir for 2 hours at room temperature. The reaction was quenched with the addition of formic acid (100 µL) and subjected to semi-preparative reverse phase HPLC purification (gradient water/methanol system) to provide the title compound (29 mg, 14%). $^1$H NMR (300 MHz, MeOD) δ 7.83 (d, J=7.1 Hz, 2H), 7.59-7.35 (m, 5H), 7.06-6.90 (m, 2H), 4.99 (d, J=8.4 Hz, 1H), 4.27-4.11 (m, 1H), 3.96-3.55 (m, 7H), 3.46-3.35 (m, 4H), 2.71-2.51 (m, 2H), 2.49-2.27 (m, 2H), 2.01 (s, 3H), 1.76-1.49 (m, 6H), 1.37 (dd, J=14.6, 7.2 Hz, 4H), 0.93 (t, J=7.2 Hz, 3H). MS (ESI$^+$) for [M+Na]$^+$; calculated: 679.3, found: 679.7.

Sodium (2R,3R,4R,5R,6S)-5-acetamido-6(4(3-(N (5-benzamidopentyl)-pentanamido)propanamido) phenoxy)-4-hydroxy-2-(hydroxymethyl)tetrahydro-2H-pyran-3-yl sulfate To a cooled (0° C.) solution of N-(5-(N-(3-((4-(2S,3R,4R,5R,6R)-3-acetamido-4,5-dihydroxy-6-(hydroxymethyl)-tetrahydro-2H-pyran-2-yl)oxy)phenyl)amino)-3-oxopropyl) pentanamido)pentyl)benzamide (25 mg, 38.1 µmol) in anhydrous pyridine (0.5 mL), benzoyl chloride (4.9 µL, 41.9 µmol) was added. After 1 hour at room temperature the solution was cooled back to 0° C. and another portion of benzoyl chloride (9.4 µL, 80.4 µmol) was added and left to stir for 2 hours at room temperature. The reaction was extracted between 1 M HCl solution and chloroform. The chloroform layer was further washed with a mixture of water and brine solution (1:1). The organic layer was concentrated and purified by flash silica column chromatography using 5% methanol in DCM as the eluent. The desired fractions were concentrated under reduced pressure and further under high vacuum. The resultant residue was dissolved in anhydrous pyridine and sulfur trioxide pyridine complex (8.3 mg, 52.1 µmol) was added to it at room temperature. The resulting mixture was heated to 45° C. for 3 hours followed by the addition of methanol (0.5 mL) and stirred for further 10 mins. The reaction mixture was concentrated under reduced pressure and further under high vacuum. The resulting residue was re-dissolved in anhydrous methanol (5.0 mL) and cooled to 0° C. To this cooled solution 0.5 M solution of sodium methoxide in methanol (0.5 mL) was added dropwise and let stir for 16 hours. The reaction was quenched by the addition of 1 M aqueous solution of sodium phosphate monobasic (1.0 mL) and subjected to semi-preparative reverse phase HPLC purification (gradient water/methanol system) to yield the title compound (5.8 mg, 20%). $^1$H NMR (300 MHz, MeOD) δ 7.80 (dd, J=7.0, 1.2 Hz, 2H), 7.58-7.38 (m, 5H), 7.03-6.94 (m, 2H), 5.01 (dd, J=8.4, 1.1 Hz, 1H), 4.75 (d, J=3.1 Hz, 1H), 4.13 (dd, J=10.9, 8.4 Hz, 1H), 3.95-3.61 (m, 6H), 3.45-3.34 (m, 4H), 2.61 (dd, J=16.1, 7.0 Hz, 2H), 2.47-2.31 (m, 2H), 1.97 (s, 3H), 1.73-1.49 (m, 6H), 1.43-1.23 (m, 5H), 0.91 (td, J=7.3, 2.2 Hz, 3H). MS (ESL) for [M-Na$^+$]$^-$; calculated: 735.3, found: 735.4.

Figure 5:
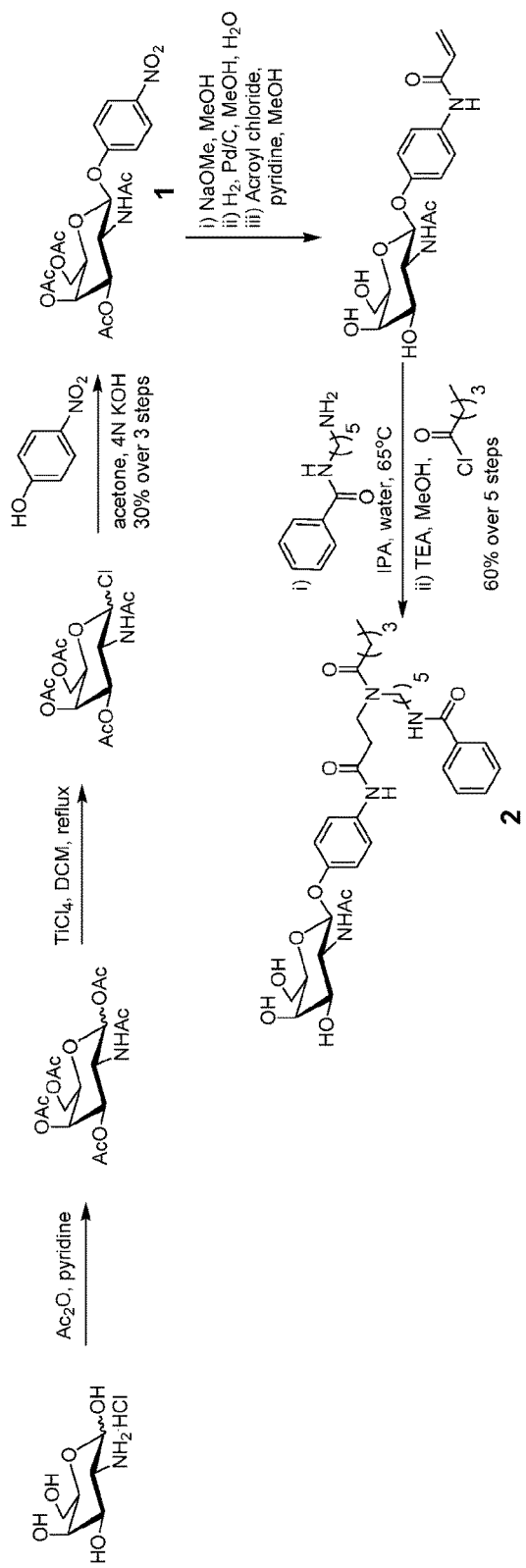
FIG. 5 is schematic illustration of the preparation of representative MPS-VI products.

MPS-VI Product. The preparation of a representative MPS-VI product is described below and illustrated in FIG. 5.

(2R,3R,4R,5R,6S)-5-acetamido-2-(acetoxymethyl)-6-(4-nitrophenoxy)tetrahydro-2H-pyran-3,4-diyl diacetate (1)

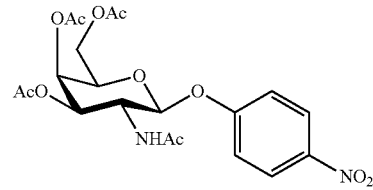

Pyridine (60 mL) was added to nitrogen back flushed flask containing D-galactosamine hydrochloride (5 g, 23.2 mmol) and the resultant slurry was cooled on an ice bath. To the cooled mixture acetic anhydride (25 g, 245 mmol) was added dropwise and allowed to warm to room temperature followed by stirring at this temperature for 16 hours. The reaction mixture was quenched with the addition of methanol (15 mL) and let stir for 20 minutes. The resultant mixture was concentrated under reduced pressure and the residue was dissolved in 20% methanol in chloroform with the aid of warming the mixture. This solution was washed with 1N HCl solution followed by brine solution. The resultant organic layer was dried using anhydrous sodium sulfate and concentrated under reduced pressure. The residue was taken in nitrogen back flushed flask equipped with a dropping funnel. Anhydrous dichloromethane (100 mL) was added to this residue and the resultant slurry was cooled on an ice bath. In the dropping funnel titanium chloride (6.5 g, 42.1 mmol) was dissolved in anhydrous dichloromethane (40 mL) and the resulting solution was added dropwise to the cooled solution. The reaction mixture was warmed to 50° C. in an oil bath and left to stir at this temperature for 48 hours. The reaction mixture was cooled back on an ice bath and saturated sodium bicarbonate solution was added dropwise with vigorous shaking. The resultant mixture was extracted between dichloromethane and saturated sodium bicarbonate solution. The organic layer was dried using anhydrous sodium sulfate and concentrated under reduced pressure. The resultant residue was dissolved in acetone (60 mL) and added slowly to a solution of 4-nitrophenol (16.1 g, 116 mmol) in acetone (130 mL) and 4N KOH aqueous solution (23.2 mL). The reaction was left to stir at room temperature for 48 hours and concentrated under reduced pressure to less than 20 mL. This solution was extracted between 1N NaOH and chloroform. The organic layer was dried using anhydrous sodium sulfate and concentrated under reduced pressure. The crude product thus obtained was purified by silica flash chromatography using 3% methanol in dichloromethane as the elution mixture. The fractions with the desired compound, as determined by TLC, were combined and concentrated under reduced pressure to get 1 (3.29 g, 30%). $^1$H NMR (300 MHz, CDCl$_3$) δ 8.20 (d, J=9.1 Hz, 2H), 7.09 (d, J=9.1 Hz, 2H), 5.61 (d, J=8.0 Hz, 1H), 5.56-5.39 (m, 3H), 4.32-4.07 (m, 4H), 2.18 (s, 3H), 2.07 (s, 3H), 2.04 (s, 3H), 1.97 (s, 3H). MS (ESI$^+$) for [M+Na]$^+$; calculated: 491.1, found: 491.2.

N-(5-(N-(3-((4-(((2S,3R,4R,5R,6R)-3-acetamido-4,5-dihydroxy-6-(hydroxymethyl)tetrahydro-2H-pyran-2-yl)oxy)phenyl)amino)-3-oxopropyl)pentanamido)pentyl)benzamide (2)

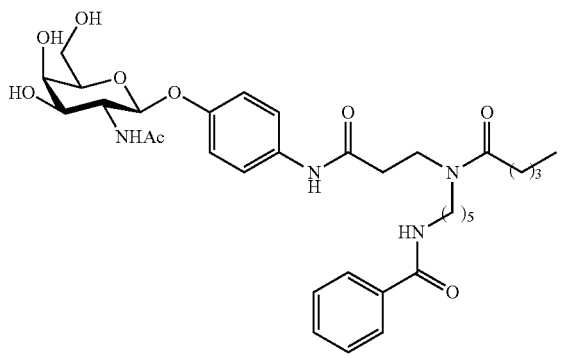

To a solution of 1 (3.5 g, 7.47 mmol) in anhydrous methanol (90 mL), cooled on an ice bath, 0.5 M sodium methoxide solution in methanol (3 mL, 1.50 mmol) was added dropwise and allowed to warm to room temperature. After 2 hours formic acid (0.1 mL) was added to the reaction mixture and concentrated to dryness under reduced pressure. To the resulting residue methanol (135 mL), water (15 mL) and 10% palladium on activated carbon (125 mg) was added and let to stir under a hydrogen atmosphere at room temperature for 16 hours. Water was added dropwise to the reaction mixture till the entire white residue was completely dissolved. The reaction mixture was filtered and the filtrate was cooled on an ice bath. To it pyridine (2 mL) and followed by the dropwise addition of a solution of acryloyl chloride (2.1 g, 23.2 mmol) in dichloromethane (50 mL). The reaction was let to stir on the ice bath for 30 minutes and then warmed to room temperature and continued for 2 hours. Sodium carbonate powder (3.0 g) was added to the reaction mix and let to stir for 15 minutes and filtered. The filtrate was concentrated under reduced pressure and further dried under high vacuum. The residue was dissolved in 2-propanol (50 mL) and water (6.6 mL) mixture and to it N-(5-aminopentyl)benzamide (2.0 g, 9.69 mmol) was added and let to stir for 40 hours at 65° C. The reaction mixture was cooled to room temperature and methanol (25 mL) was added to it. Upon cooling this mixture on an ice bath triethylamine (2.5 mL) was added followed by the dropwise addition of a solution of pentanoyl chloride (2.7 g, 22.4 mmol) in dichloromethane (50 mL). The reaction was left to stir on the ice bath for 30 minutes and then warmed to room temperature and continued for 16 hours. The reaction mixture was concentrated under reduced pressure and subjected to purification by silica flash chromatography using 15% methanol in dichloromethane as the elution mixture to yield 2 (2.96 g, 60%). $^1$H NMR (300 MHz, MeOD) δ 7.84 (d, J=7.1 Hz, 2H), 7.59-7.35 (m, 5H), 7.09-6.91 (m, 2H), 5.00 (d, J=8.4 Hz, 1H), 4.28-4.09 (m, 1H), 3.97-3.55 (m, 7H), 3.46-3.24 (m, 4H), 2.72-2.51 (m, 2H), 2.49-2.28 (d, J=7.3 Hz, 2H), 2.02 (s, 3H), 1.78-1.49 (m, 6H), 1.49-1.22 (m, 4H), 0.94 (t, J=7.1 Hz, 3H). MS (ESI$^+$) for [M+H]$^+$; calculated: 657.3, found: 657.5.

Example 6

Representative Assay using MPS-VI Reagents

In this example, a representative assay using MPS-VI reagents of the invention is described. The results for these reagents is compared to other MPS-VI reagents.

The original MSP-VI reaction is shown below (Duffey, T. A., Sadilek, M., Scott, C. R., Turecek, F., Gelb, M. H. (2010) "Tandem mass spectrometry for the direct assay of lysosomal enzymes in dried blood spots: Application to screening newborns for Mucopolysaccharidosis VI (Maroteaux-Lamy Syndrome)", Anal. Chem., 82:9587-9591.). Note that the S, P and IS have the BOC group and that the P and IS are not chemically identical (the P has 6 CH2 groups in the linker whereas the IS has 5).

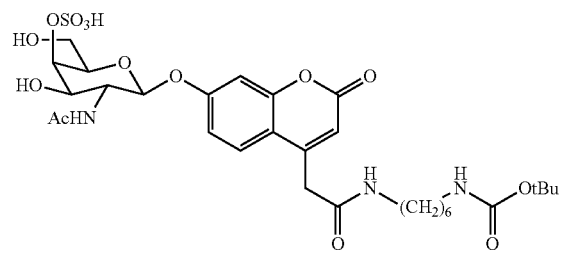

MPS-VI Substrate

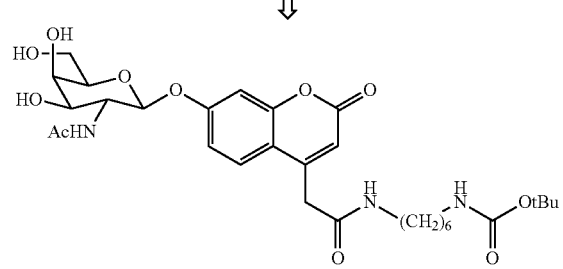

MPS-VI Product

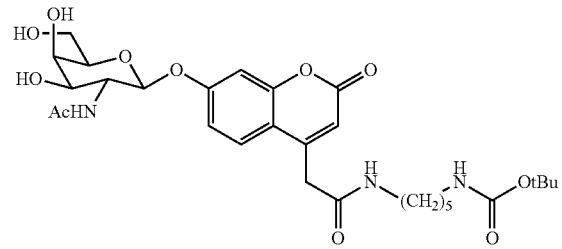

MPS-VI Internal Standard

The alternative MPS-VI reaction is shown below:

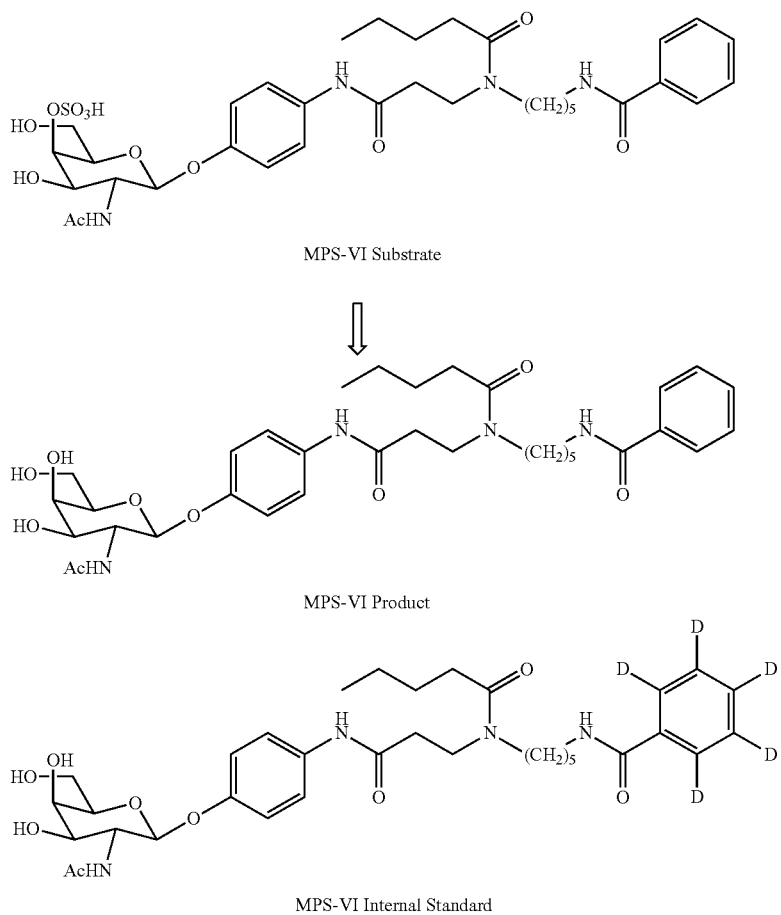

MPS-VI Substrate

MPS-VI Product

MPS-VI Internal Standard

Note the different aglycone that has an N-pentanoyl group, no BOC carbamate group. Note also that the internal standard is chemically identical to the product but has 5 deuteriums in the benzoyl group.

The original and alternative MPS-VI substrates were compared in side-by-side enzyme assays as follows: 1 mM substrate, 10 uM internal standard in 30 uL of buffer (100 mM ammonium formate, pH 4.0, 7.5 mM barium(II) acetate, 5.0 mM cerium(III) acetate). A 3 mm punch of a dried blood spot was added, and the mixtures were incubated with shaking for 16 hours at 37 deg C. The reactions were quenched by addition of an aqueous suspension (1:1) of DEAE cellulose (Whatmann DE52) (100 uL), followed by addition of 400 uL of ethyl acetate. The mixture was mixed by up and down pipetting a few times and then centrifuged (10 min at 3000 rpm) to separate the liquid layers and pellet the DE52. A 300 uL portion of the upper ethyl acetate layer was transferred to a new well, and solvent was removed by evaporation with a stream of oil-free air. The residue was taken up in 100 uL of methanol/5 mM aqueous ammonium formate (80/20, v/v) and infused into the tandem mass spectrometer. The barium and cerium salts are present to precipitate free sulfate and phosphate present in the dried blood spot since these anions cause production inhibition of the MPS-VI enzyme. The DE52 is added to trap remaining substrate so only product and internal standard (which are charge neutral) are extracted into ethyl acetate. A blank assay is also carried out in which a blood-free 3 mm punch of filter paper is substituted for the dried blood spot. The blank is incubated and processed as above.

TABLE 5

Comparative MPS-VI Assay Results.

| Substrate | Enzymatic Activity[1] (umole/hr/ L blood) | Coeff. of Variation on activity[2] | MSMS response of IS and P[3] (ion counts/ pmole) | blood-no blood assay ratio[4] |
|---|---|---|---|---|
| Original MPS-VI | 1.25 | 7.36 | 29.7 | 4.9 |
| Alternative MPS-VI | 1.5 | 3.2 | 290 | 77.9 |

[1]Enzymatic activity is expressed as umoles of product formed per hour per liter of blood.
[2]Coefficient of Variation (CV) is based on 6 runs of the assay each carried out with a different punch from the same dried blood spot.
[3]MSMS response is the amount of ion counts measured in the tandem mass spectrometry channel per pmole of analyte.
[4]Blood-no blood assay ratio is the enzymatic activity measured in an assay with a dried blood spot punch to that measured with a blood-free punch.

It can be seen from the above table that both MPS-VI substrates display similar activity on the MPS-VI enzyme (umoles product produced per hr per liter of blood) but that the alternative substrate gives rise to a product that is about 10-fold more sensitive in MSMS detection (ion counts detected per pmole of analyte). The improvement in blood-no blood assay response is probably due to a lower amount of product as a contaminant in the alternative MPS-VI substrate because the new substrate is easier to produce in product-free form.

Example 7

Representative Sulfatase Assay for MPS-II

In this example, a representative assay of the invention (assay for iduronic acid 2-sulfatase, the enzyme that is deficient in Hunter Syndrome (MPS-II)) is described.

The first step in the reaction is as described above (see also WO 2009/026252 (PCT/US2008/073516), WO 2010/081163 (PCT/US2010/020801), WO 2012/027612 (PCT/US2011/049224), and WO 2013/070953 (PCT/US2012/064205)).

In the assay, a second enzyme, alpha-L-iduronidase (a glycohydrolase) is added to the assay cocktail, which converts Initial MPS-II Product to Final MPS-II Product by removing the iduronic acid residue leaving the aglycone. The iduronidase can be present in the assay cocktail that is incubated with the dried blood spot, or it can be added after the first incubation with the dried blood spot followed by a second incubation period. The amount of iduronidase added is sufficient to convert all Initial MPS-II Product to Final MPS-II Product. The assay cocktail also contains Initial MPS-II Internal Standard (same as Initial MPS-II Product but, for example, with 5 deuteriums in the benzoyl group), which is converted by iduronidase to Final MPS-II Internal Standard. Both Final MPS-II Product and Final MPS-II Internal Standard are detected by tandem mass spectrometry, which enables the amount of Final MPS-II Product to be quantified. Typically the reaction mixture is extracted with an organic solvent to cause Final MPS-II Internal Standard and Final MPS-II Product to partition into the organic solvent phase in a relatively salt-free form. The organic solvent is removed by evaporation, the residue is dissolved in solvent and the solvent is injected into the tandem mass spectrometer. The analytes are detected by multiple reaction monitoring.

Using an assay that does not include the second enzyme (i.e., the glycohydrolase) and using a 3 mm punch of a dried blood spot from a newborn screening card, 10,000-30,000 ion counts are typically observed for Initial MPS-II Product after an incubation time of 12-18 hours. Using the assay of the invention with the iduronidase, 1 million-5 million ion counts are typically observed for Final MPS-II Product. Thus the assay sensitivity has been improved by about 100-fold. A second advantage of the method of the invention is that in the previous assay, remaining MPS-II Substrate that enters the mass spectrometer electrospray ionization source undergoes some degree of desulfation due to heating in the source. This increases the assay background by giving rise to product signal that is independent of the action of iduronic acid 2-sulfatase. With the assay of the invention, this desulfation is of no concern because the product being detected is the aglycone (Final MPS-II Product).

The iduronidase used is the human enzyme that was obtained by overexpression in mammalian cells. Any iduronidase can be used as long as it does not act on MPS-II substrate (i.e., cleaves the glycosidic linkage only after the sulfate has been removed from the iduronic acid).

Example 8

Representative Sulfatase Assay for MPS-VI

A suitable second enzyme for use in a representative assay for MPS-VI is bacterial N-acetylgalactosaminidase and is used to release N-acetyl-galactosamine from its aglycone after the MPS-VI enzyme removes the sulfate from the 4-position of the sugar. This improves assay sensitivity by about 20-fold. Other suitable enzymes include bacterial N-acetyl hexosaminidases.

Example 9

Representative Sulfatase Assay for MPS-IVA

A suitable second enzyme for use in a representative assay for MPS-IVA is *betagalactosidase* from *Aspergillus* species and is used to release galactose from its aglycone after the MPS-IVA enzyme removes the sulfate from the 6-position of the sugar. This improves assay sensitivity by about 20-fold. The *Aspergillus enzyme* is preferred over, for example, the *E. coli* enzyme, because it retains high activity at pH 4-5, the pH of the MPS-IVA assay. Alternatively, one can use the MPS-IVA substrate with N-acetyl-galactosamine-6-sulfate, and the initial MPS-IV product is acted on by the same enzyme used in the MPS-VI assay (see above) to provide the aglycone.

Example 10

Representative Sulfatase Assay for MPS-IIIA

A suitable second enzyme for use in a representative assay for MPS-IIIA is yeast alpha-glucosidase from Bakers yeast, which is used to release glucosamine from its aglycone after the MPS-IIIA enzyme removes the sulfate from the amino group of glucosamine-N-sulfate. Alternatively, acetyl-Co A: glucosamine N-acetyltransferase can be used to acetylate the free amino group after the MPS-IIIA enzyme removes the sulfate. Both mammalian and bacterial acetyltransferases can be used.

Example 11

Representative Assay for MPS-IVA

In this example, a representative assay for MPS-IVA is described using bacterial enzyme, beta-N-acetylgalactosaminidase (beta-NGA), which cleaves beta glycosides to N-acetyl-galactosamine when it is not sulfated on the 6-position, and an inhibitor of human hexosaminidase A, (Z)—O-(2-acetamido-2-deoxy-D-glucopyranosylidene)-amino N-phenylcarbamate (Z-PUG-NAc), to block human hexosamidinase A action on the GALNS substrate.

The GALNS substrate used in the assay has the following structure:

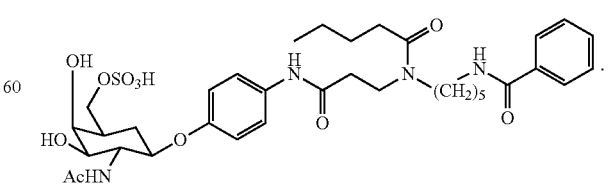

The GALNS internal standard used in the assay has the following structure:

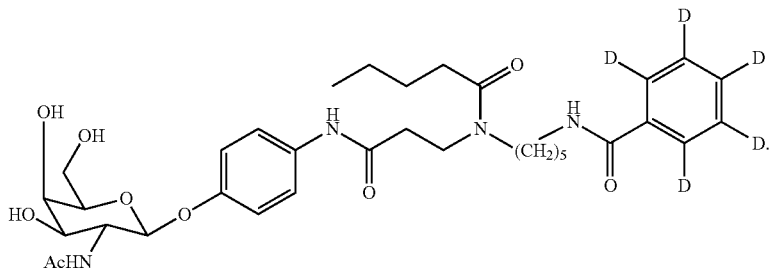

Experiment 1. A 3 mm punch of a dried blood spot from a random newborn is incubated with 0.03 mL of assay cocktail consisting of 1 mM GALNS substrate in 50 mM ammonium formate pH 4.0 containing 7.5 mM barium acetate, 5.0 mM cerium acetate, 1 mM Z-PUG-NAc, and 0.01 mg of bacterial beta-N-acetylgalactosaminidase. The mixture also contains 0.005 mM internal standard. After 16 hrs at 37° C. with shaking, the mixture is quenched with 0.12 mL of acetonitrile and the sample plate is centrifuged to pellet the precipitate. Supernatant (0.12 mL) is transferred to a new plate, and 0.12 mL of water is added. The plate is placed on the autosampler of the UHPLC-MS/MS instrument (Waters Xevo TQ MS/MS with a Waters Acquity UHPLC system). A portion of the sample (0.01 mL) is injected, and the GALNS product (substrate minus sulfate), the internal standard, and the aglycones derived from the GALNS product and internal standard are quantified by multiple reaction monitoring (MS/MS). Note the internal standard added, like the GALNS product, is converted to its aglycone by the addition of bacterial beta-N-acetylgalactosaminidase. Table 1 above shows the MS/MS ion peak areas for each analyte.

Experiment 1 shows the results of the complete assay with a blood containing punch, GALNS substrate, internal standard, 1 mM Z-PUG-NAc, and 0.01 mg beta-NGA in assay buffer. The aglycone signal of 411,000 ion peak area is much larger than the signal for the initially formed GALNS product showing that beta-NGA converts most of the product to the aglycone. Experiment 1 also shows that most of the internal standard is converted to the aglycone. The amount of aglycone and internal standard aglycone is used to determine the amount of GALNS enzymatic activity.

Experiment 2. Experiment 2 is the same as Experiment 1 but uses a punch of filter paper (no blood). Most of the internal standard is converted to the aglycone showing that the added beta-NGA is working. The amount of aglycone is only 42,000, about 10-fold lower than that seen in the presence of blood. This high blood-to-no-blood ratio shows that the GALNS assay is working. Furthermore when a dried blood spot from a confirmed Morquio A patient is used, the amount of aglycone is similar to that seen in the absence of blood (45,000) showing that the assay is working to detect only the GALNS present in blood from a non-affected individual.

Experiment 3. Experiment 3 shows a complete assay but with no beta-NGA. As expected, most of the internal standard is not converted to its aglycone, because is no beta-NAG and any hexosaminidase A coming from the blood is blocked by Z-PUG-NAc. The amount of GALNS product is 121,000 and the amount of aglycone is 42,900.

Experiment 4. Experiment 4 is the same as Experiment 3, but without blood. Experiment 4 shows only 753 for GALNS product. Thus, most of the 121,000 product counts in Experiment 3 is due to GALNS. The product counts in Experiment 3 cannot be due to hexosaminidase A, because only beta-NGA generates the aglycone. The amount of aglycone in Experiments 3 and 4 are similar, and this represents aglycone present in the GALNS substrate as a contaminant.

Experiments 1-4 also show the advantage of converting GALNS product to its aglycone; with blood and beta-NGA the aglycone signal is 411,000, and this is compared to only 121,000 for GALNS product when it was not converted to its aglycone by beta-NGA. Thus, a 4-fold increase in GALNS assay sensitivity is gained.

Experiment 5. Experiment 5 shows the complete assay, but lacks the hexosaminidase A inhibitor Z-PUG-NAc. Most of the internal standard is converted to its aglycone as expected because beta-NGA is present. The signal for aglycone is 1,350,000, much larger than in Experiment 1. This shows that hexosaminidase A, if left non-inhibited, generates a substantial amount of aglycone from the GALNS substrate.

Experiment 6. Experiment 6 contains blood but no beta-NGA and no Z-PUG-NAc. The amount of GALNS product is 110,000 instead of 25,100 as in Experiment 5, which is due to the action of GALNS on the GALNS substrate. Because beta-NGA is absent, only a small amount of GALNS product is converted to aglycone, but the amount of aglycone remains high at 1,110,000. This is because of the action of hexosaminidase A in the blood on GALNS substrate in the absence of Z-PUG-NAc.

Experiments 7 and 8. Experiments 7 and 8 are with filter paper (no blood). Experiment 7 includes beta-NGA, whereas Experiment 8 does not include beta-NGA. As expected, most of the internal standard is converted to aglycone in Experiment 7, but not in Experiment 8. Experiment 8 shows that the GALNS substrate contains small amounts of product (820) and aglycone (14,500) as contaminants. These can be removed by a further round of purification of GALNS substrate.

The results in Table 1 clearly show that the action of non-inhibited human hexosaminidase A endogenously present in dried blood spots generates excessive much aglycone from the GALNS substrate to lead to a useful GALNS assay in the absence of a hexosaminidase A inhibitor. The data also clearly show that beta-NGA has the desired properties: it converts most of the GALNS product and the internal standard to their aglycones even in the presence of sufficient hexosaminidase A inhibitor Z-PUG-NAc to fully block hexosaminidase A.

While the preferred embodiment of the invention has been illustrated and described, it will be appreciated that various changes can be made therein without departing from the spirit and scope of the invention.

The invention claimed is:

1. A method for assaying For an enzyme associated with a lysosomal storage disease, comprising:
   (a) contacting a sample with a first solution to provide a solution comprising one or more lysosomal enzymes;
   (b) contacting the one or more lysosomal enzymes in solution with an enzyme substrate for each lysosomal enzyme to be analyzed and incubating the substrates with the enzymes for a time sufficient to provide a solution comprising an enzyme product for each lysosomal enzyme present in the sample,
   wherein at least one enzyme substrate for each lysosomal enzyme is a compound having a carbohydrate moiety and an aglycone moiety and having the formula:

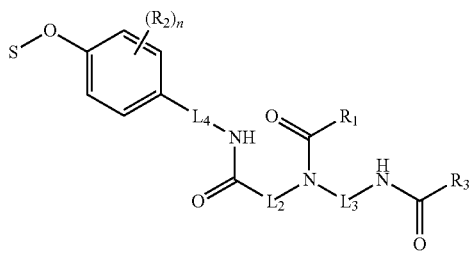

wherein
$L_2$ is a linker comprising 1-20 carbon atoms in which one or more carbon atoms may be replaced with a heteroatom selected from N, O, and S, and/or one or more of carbon atoms may be substituted with a $C_1$-$C_6$ alkyl group or halogen;
$L_3$ is a linker comprising 1-20 carbon atoms in which one or more carbon atoms may be replaced with a heteroatom selected from N, O, or S, and/or one or more of carbon atoms may be substituted with a $C_1$-$C_6$ alkyl group or halogen;
$L_4$ is optional and when present is a linker comprising 1-20 carbon atoms in which one or more carbon atoms may be replaced with a heteroatom selected from N, O, or S), and/or one or more of carbon atoms may be substituted with a $C_1$-$C_6$ alkyl group or halogen;
$R_1$ is a $C_1$-$C_{10}$ alkyl group;
$R_2$ at each occurrence is independently selected from a $C_1$-$C_{10}$ alkyl group, a $C_1$-$C_{10}$ alkoxy group, halogen, nitro, —C(═O)NHR, or —C(═O) OR, where R is $C_1$-$C_8$ alkyl group;
$R_3$ is a $C_1$-$C_{10}$ alkyl group or a substituted or unsubstituted $C_6$-$C_{10}$ aryl group; and n is 0, 1, 2, 3, or 4; and S is

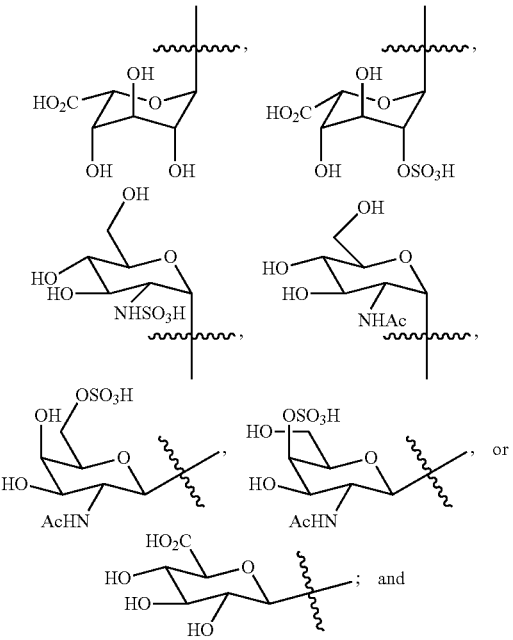

(c) determining the quantities of one or more of the enzyme products: wherein the enzyme associated with a lysosomal storage disease is selected from the group consisting of:
(i) alpha-L-iduronidase:
(ii) iduronate 2-sulfatase;
(iii) heparan N-sulfatase;
(iv) N-acetyl-alpha-D-glurosaminidase;
(v) N-acetylgalactosamine 6-sulfate-sulfatase;
(vi) N-acetylgalactosamine 4-sulfate-sulfatase; and
(vii) beta-glucuronidase.

2. The method of claim 1, wherein determining the quantities of the enzyme products comprises mass spectrometric analysis.

3. The method of claim 1, wherein determining the quantities of the enzyme products comprises conducting the products to a mass spectrometer by liquid chromatography or by flow injection.

4. The method of claim 1 further comprising using the quantities of the enzyme products to determine whether the sample is from a candidate for treatment for a condition associated with one or more lysosomal enzyme deficiencies.

* * * * *